United States Patent
Sakata et al.

[11] Patent Number: 5,851,982
[45] Date of Patent: Dec. 22, 1998

[54] LIQUID SOFTENER COMPOSITIONS AND QUATERNARY AMMONIUM SALT

[75] Inventors: Yuushi Sakata; Junichi Inokoshi; Osamu Tachizawa; Tohru Katoh; Uichiro Nishimoto; Yasuki Ohtawa; Akira Sakaguchi, all of Wakayama; Kohshiroh Sotoya, deceased, late of Wakayama, by Yoko Sotoya, Hidetsugu Sotoya, Shigehiko Sotoya, legal representatives; Noriko Yamaguchi, Wakayama, all of Japan

[73] Assignee: Kao Corporation, Tokyo, Japan

[21] Appl. No.: 619,644

[22] PCT Filed: Jul. 27, 1995

[86] PCT No.: PCT/JP95/01498

§ 371 Date: Jul. 5, 1996

§ 102(e) Date: Jul. 5, 1996

[87] PCT Pub. No.: WO96/03370

PCT Pub. Date: Feb. 8, 1996

[30] Foreign Application Priority Data

Jul. 27, 1994 [JP] Japan ................. 6-175227
Feb. 16, 1995 [JP] Japan ................. 7-28196

[51] Int. Cl.$^6$ ................. D06M 13/46; C07C 211/62
[52] U.S. Cl. ................. 510/515; 510/521; 510/522; 510/526; 510/527; 554/110; 554/114; 564/295; 564/296
[58] Field of Search ................. 510/515, 521, 510/522, 526, 527; 554/110, 114; 564/295, 296

[56] References Cited

U.S. PATENT DOCUMENTS 4,228,042 10/1980 Letton ................. 510/331

OTHER PUBLICATIONS

Derwent WPI, English abstract for JP 3–90677 (Apr. 1991).
Derwent WPI, English abstract for JP 1–162872 (Jun. 1989).
Derwent WPI, English abstract for DE 3,527,974 (Feb. 1987).
Derwent WPI, English abstract for EP 298,065 (Oct. 1989).
Derwent WPI, English abstract for JP 54–130509 (Oct. 1979).

*Primary Examiner*—Anthony Green
*Attorney, Agent, or Firm*—Birch, Stewart, Kolasch & Birch, LLP

[57] ABSTRACT

To provide a liquid softener composition which is satisfactory in respects of softening effect, storage stability and water absorption properties, is excellent in biodegradability and is gentle with the environment. A liquid softener composition comprising 3 to 40% by weight of a quaternary ammonium salt (7-I) and water

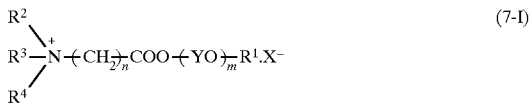

(7-I)

wherein $R^1$ represents $C_{20}$–$C_{44}$ alkyl or alkenyl group; $R^2$, $R^3$, and $R^4$ are the same of different from each other and are $C_1$–$C_5$ alkyl or hydroxyalkyl group; Y represents $C_2$–$C_4$ alkylene group; m is a number of 0 to 20; n is an integer of 1 to 6; and $X^-$ represents an anion group.

35 Claims, No Drawings

LIQUID SOFTENER COMPOSITIONS AND QUATERNARY AMMONIUM SALT

The present invention relates to liquid softeners which can impart excellent softness and elasticity (fluffiness) to various textiles, exhibit excellent storage stability and water absorption properties, and are excellent in biodegradability to be gentle with the environment.

[PRIOR ART]

Most of the commercially available current household softeners are compositions mainly comprising di(hardened tallow alkyl)dimethylammonium chloride, which is because this quaternary ammonium salt exerts an excellent softening effect on various textiles even when used in a small amount.

However, the above quaternary ammonium salt sometimes lowers the elasticity of textile (particularly cotton) to impair the reeling thereof, when applied to the textile in an enhanced concentration for the purpose of attaining higher softness in spite of the excellent softening effect of the salt.

Further, when softener compositions containing the above quaternary ammonium salt are stored for long, they are liable to cause thickening, gelation or phase separation owing to their physicochemical properties. The commercially available softeners mainly comprising the above quaternary ammonium salt are also still insufficient in long-term storage stability, though they are in a state improved in this respect by the addition of a polyoxyethylene-type nonionic surfactant, electrolyte, solvent or other additive.

In order to overcome these disadvantages of the quaternary ammonium salt of the prior art, there have been proposed various softeners characterized by comprising a quaternary nitrogen atom, a long-chain alkyl moiety and an ester group introduced between the nitrogen atom and the alkyl moiety. For example, JP-A-90677/1991 discloses a softener composition containing a quaternary ammonium salt having an ester group which can be well dispersed without gelation, and JP-A-162872/1989 discloses another softener composition containing a quaternary ammonium salt having an ester group which exhibits excellent viscosity stability even when stored at high temperature.

However, these softener compositions characterized by comprising a quaternary ammonium salt having an ester group are still insufficient in softening effect, storage stability and water absorption properties (incidentally, the textile treated with a softener poor in water absorption properties tends to repel water, exhibiting poor feelings in use).

Furthermore, DE-A3527974 discloses $C_{10}$–$C_{30}$ alkyl ester of trimethyl quaternary ammonium carboxylic acid and adducts thereof with ethylene oxide as hair care component. Additionally, EP-A298065 discloses $C_{10}$–$C_{18}$ alkyl ester of trimethyl quaternary ammonium carboxylic acid as a preventive drug for sexual diseases.

[DISCLOSURE OF THE INVENTION]

An object of the present invention is to provide a liquid softener composition which is satisfactory in softening effect, storage stability and water absorption properties and is excellent in biodegradability to be gentle with the environment.

The inventors of the present invention have intensively studied to find that the above object can be attained by a liquid softener composition containing a quaternary ammonium salt having an extremely specific structure. The present invention has been accomplished on the basis of this finding.

The present invention provides a quaternary ammonium salt, processes for the preparation of quaternary ammonium salt and liquid softener compositions containing the salt.

The quaternary ammonium salt of the present invention is represented by the general formula (7-I-2).

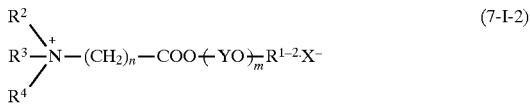

[wherein $R^{1\text{-}2}$: linear or branched $C_{36}$–$C_{44}$ alkyl or alkenyl group, $R^2$, $R^3$, $R^4$: $C_1$–$C_5$ alkyl or hydroxyalkyl group, wherein $R^2$, $R^3$ and $R^4$ may be the same or different from each other, Y: linear or branched $C_2$–$C_4$ alkylene group, m: a number of 0 to 20 corresponding to the average number of alkylene oxide molecules added, n: an integer of 1 to 6, and $X^-$: an anion].

Preferable examples of the quaternary ammonium salt of the present invention include the following (1) and (2):

(1) quaternary ammonium salts represented by the general formula (1-I-2), still preferably those represented by the general formula (1-I-1):

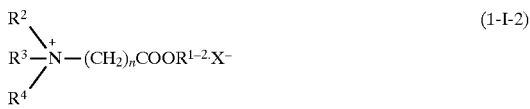

[wherein $R^{1\text{-}2}$: linear or branched $C_{36}$–$C_{44}$ alkyl or alkenyl group, preferably linear or branched $C_{36}$–$C_{44}$ alkyl group, and $R^2$, $R^3$, $R^4$, n, $X^-$: each as defined above].

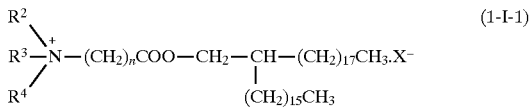

[wherein $R^2$, $R^3$, $R^4$, n, $X^-$: each as defined above], and (2) YO adduct type quaternary ammonium salts represented by the general formula (7-I -2) wherein m is a number of 1 to 20 corresponding to the average number of alkylene oxide molecules added, i.e., quaternary ammonium salts represented by the following general formula (2-I):

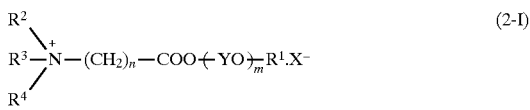

Preferable examples of the adduct type quaternary ammonium salts (2) include those represented by the general formula (7-I-1) wherein m is a number of 1 to 20 corresponding to the average number of alkylene oxide molecules added, and those represented by the following general formula (2-I-1):

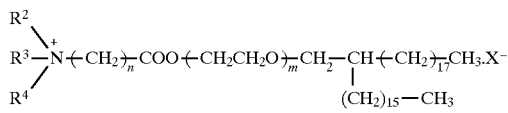  (2-I-1)

[wherein $R^2$, $R^3$, $R^4$, n, m, $X^-$: each as defined above].

A liquid softener composition according to the present invention comprises the following component (7-A) and water, characterized in that the content of the component (7-A) in the composition is 3 to 40% by weight, the component (7-A) being a quaternary ammonium salt represented by the general formula (7-I):

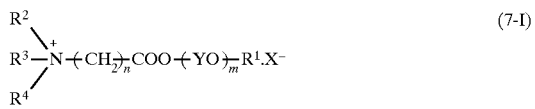  (7-I)

[wherein
$R^1$: linear or branched $C_{20}$–$C_{44}$ alkyl or alkenyl group,
$R^2$, $R^3$, $R^4$: $C_1$–$C_5$ alkyl or hydroxyalkyl group, wherein $R^2$, $R^3$ and $R^4$ may be the same or different from each other,
Y: linear near or branched $C_2$–$C_4$ alkylene group
m: a number of 0 to 20 corresponding to the average number of alkylene oxide molecules added,
n: an integer of 1 to 6, and
$X^-$: an anion].

The softener composition comprising a quaternary ammonium salt belonging to the type (1) and water is one comprising a quaternary ammonium salt represented by the general formula (7-A) wherein m is 0 and $R^1$ is linear or branched $C_{20}$–$C_{44}$ alkyl group(such a salt is hereinafter referred to as "component (1-A)") and water.

It is preferable that the component (1-A) be one represented by the general formula (7-I) wherein m is 0 and $R^1$ is linear or branched $C_{28}$–$C_{44}$ alkyl. It is still preferable that the component (1-A) be one represented by the general formula (1-I-1):

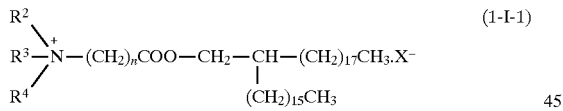  (1-I-1)

[wherein $R^2$, $R^3$, $R^4$, n, $X^-$: each as defined above].

It is preferable that a linear or branched, saturated or unsaturated $C_8$–$C_{44}$ alcohol be further contained as the component (1-B) in an amount or at most 110% by weight based on the component (1-A).

The composition comprising a quaternary ammonium salt (2) and water is one comprising a quaternary ammonium salt represented by the general formula (7-I) wherein m is a number of 1 to 20 corresponding to the average number of alkylene oxide molecules added (such a salt is hereinafter referred to as "component (2-A)") and water.

It is preferable that the component (2-A) be one represented by the general formula (7-I) wherein $R^1$ group is a group represented by the formula:

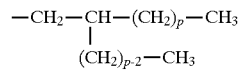

(wherein p is a number of 9 to 21) and Y is ethylene group. It is still preferable that the component (2-A) be one represented by the general formula (2-I-1):

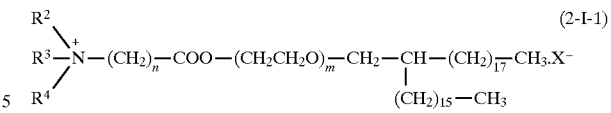  (2-I-1)

[wherein $R^2$, $R^3$, $R^4$, n, m, $X^-$: each as defined above].

It is preferable that a linear or branched, saturated or unsaturated $C_8$–$C_{44}$ alcohol be further contained in the composition as the component (2-B) in an amount of at most 110% by weight based on the component (2-A).

Further, the present invention also provides other compositions, i.e., one comprising the quaternary ammonium salt and adducts of glycerides with alkylene oxide and one comprising the salt and an adduct of a amide compound with alkylene oxide.

That is, another liquid softener composition is one comprising the following components (3-A) and (3-B) at a weight ratio of the component (3-A) to the component (3-B) of 2/1 to 1/9: [component (3-A)]

a mixture comprising a compound represented by the following general formula (3-I) (hereinafter referred to as "compound (3-I)"), a compound represented by the following general formula (3-II) (hereinafter referred to as "compound (3-II)"), a compound represented by the following general formula (3-III) (hereinafter referred to as "compound (3-Ill)"), and a compound represented by the following general formula (3-IV) (hereinafter referred to as "compound (3-IV)"), with the provisos that the mixing ratio by weight or the compounds (3-I), (3II), (3-III) and (3-IV) must satisfy the following relationships:

[compound (3-I)]/[ the sum total of the compounds (3-I), (3-II), (3-III) and (3-IV)]=0.040 to 0.527,

[compound (3-II)]/[the sum total of the compounds (3-I), (3-II), (3-III) and (3-IV)]=0.133 to 0.469,

[compound (3-III)]/[the sum total of the compounds (3-I), (3-II), (3-III) and (3-IV)]=0.013 to 0.661, and

[compound (3-IV)]/[the sum total of the compounds (3-I), (3-II), (3-III) and (3-IV)]=0.001 to 0.417 and that the mixture comprising the compounds (3-I), (3-II), (3-III) and (3-IV) has a Griffin's HLB value of 5 to 15:

  (3-I)

[wherein
$A^1$, $A^2$, $A^3$: RCO group or H atom, wherein R group represents linear or branched $C_7$–$C_{23}$ alkyl or alkenyl group, with the proviso that one of $A^1$, $A^2$ and $A^3$ group is RCO group and the others thereof are hydrogen atom,
Q: $C_2$–$C_3$ alkylene group or a mixture of $C_2$ alkylene group) With $C_3$ alkylene group, and
a, b, c: a number of 0 or above, with the proviso that the sum of a, b and c is 1 to 50 on an average],

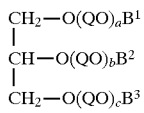 (3-II)

[wherein
B¹, B2, B³: RCO group or H atom, wherein R is as defined above, with the proviso that two of B¹, B2 and B³ are RCO group and the other thereof is H atom, and
Q, a, b, c: each as defined above],

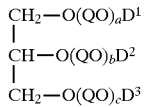 (3-III)

[wherein
D¹, D², D³: RCO group, wherein R group is as defined above, and
Q, a, b, c: each as defined above], and

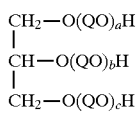 (3-IV)

[wherein Q, a, b, c: each as defined above], and

[component (3-B)]

a quaternary ammonium salt represented by the following general formula (3-V):

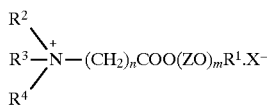 (3-V)

[wherein
$R^1$: linear or branched $C_{20}$–$C_{44}$ alkyl or alkenyl group,
$R^2$, $R^3$, $R^4$: $C_1$–$C_5$ alkyl or hydroxyalkyl group, wherein $R^2$, $R^3$ and $R^4$ may be the same or different from each other,
Z: $C_2$–$C_3$ alkylene group or a mixture of $C_2$ alkylene group with $C_3$ alkylene group,
m: a number of 0 to 20,
n: a number of 1 to 6, and
$X^-$: an anion].

It is preferable that R in the general formulae (3-I) to (3-III) be at least one member selected from the group consisting of alkyl group resulting from coconut oil fatty acid, alkyl group resulting from palm kernel oil fatty acid, alkyl group resulting from palm oil fatty acid, alkyl group resulting from palm stearic acid, alkyl group resulting from hardened palm stearic acid, alkyl group resulting from tallow fatty acid, and alkyl group resulting from hardened tallow fatty acid. Further, it is still preferable that R group in the general formulae (3-I) to (3-III) be at one member selected from the group consisting of alkyl group resulting from tallow fatty acid, alkyl group resulting from hardened tallow fatty acid, alkyl group resulting from palm stearic acid, and alkyl group resulting from hardened palm stearic acid.

It is preferable that the component (3-B) be a quaternary ammonium salt represented by the general formula (3-V-1):

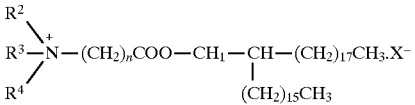 (3-V-1)

[wherein $R^2$, $R^3$, $R^4$, n, $X^-$: each as defined above].

Further, the total amount of the components (3-A) and (3-B) is preferably 3 to 40% by weight based on the composition. Furthermore, the liquid softener composition may contain a linear or branched, saturated or unsaturated $C_8$–$C_{44}$ alcohol as component (3-C) in an amount of at most 110% by weight based on the component (3-B).

The other liquid softener composition according to the present invention is one comprising the following components (4-A) and (4-B) at a weight ratio of the component (4-A) to the component (4-B) or 2/1 to 1/9:

[component (4-A)]

a compound represented by the following general formula (4-I):

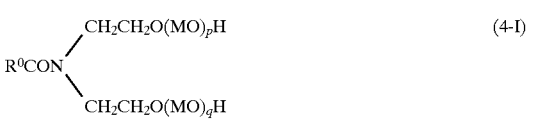 (4-I)

[wherein
$R^0$: linear or branched $C_7$–$C_{23}$ alkyl or alkenyl group,
M: $C_2$–$C_3$ alkylene group or a mixture of $C_2$ alkylene group with $C_3$ alkylene group, and
p, q: a number of 0 or above, with the proviso that the sum of p and q is 0 to 4 on an average] and

[component (4-B)]

a quaternary ammonium salt represented by the following general formula (4-II):

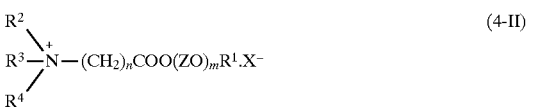 (4-II)

[wherein
$R^1$: linear or branched $C_{20}$–$C_{44}$ alkyl or alkenyl group,
$R^2$, $R^3$, $R^4$: $C_1$–$C_5$ alkyl or hydroxyalkyl group, wherein $R^2$, $R^3$ and $R^3$ may be the same or different from each other,
Z: $C_2$–$C_3$ alkylene group or a mixture of $C_2$ alkylene group with $C_3$ alkylene group,
m: number of 0 to 20,
n: a number of 1 to 6, and
$X^-$: an anion].

It is preferable that the component (4-A) be one represented by the general formula (4-I) wherein p and q are 0. It is also preferable that $R^0$ group in the general formula (4-I) be at least one member selected from the group consisting of alkyl resulting from coconut oil fatty acid, alkyl resulting from palm kernel oil fatty acid, alkyl resulting from palm oil fatty acid, alkyl resulting from palm stearic acid, alkyl resulting from hardened palm stearic acid, alkyl resulting from tallow fatty acid, and alkyl resulting from hardened tallow fatty acid.

It is preferable that the component (4-B) be a quaternary ammonium salt represented by the general formula (4-II-1):

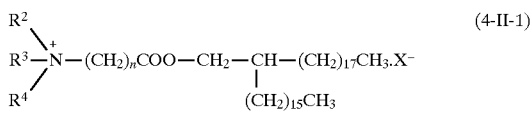

(4-II-1)

[wherein $R^2$, $R^3$, $R^4$, n, $X^-$: each as defined above].

Further, the total amount of the components (4-A) and (4-B) is preferably 3 to 40% by weight based on the composition. Furthermore, the liquid softener composition may contain a linear or branched, saturated or unsaturated $C_8$–$C_{44}$ alcohol as component (4-C) in an amount of at most 110% by weight based on the component (4-B)

The present invention also provides processes (5) and (6) for the preparation of a quaternary ammonium salt.

The process (5) is one of preparing a quaternary ammonium salt represented by the general formula (5-I):

(5-I)

(wherein $R^1$ represents linear or branched $C_{20}$–$C_{44}$ alkyl or alkenyl; $R^2$, $R^3$ and $R^4$ represent the same or different from each other $C_1$–$C_5$ alkyl or hydroxyalkyl group; a is a number of 1 to 6; and $X^-$ represents an anion) by reaction of a corresponding tertiary amine with a quaternizing agent, characterized by conducting the reaction in the presence of a polyhydric alcohol ester represented by the general formula (5-II):

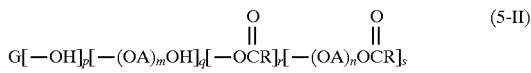

(5-II)

[wherein

G group: a residue obtained by freeing a starting polyhydric alcohol completely from alcoholic hydroxyl groups, [—OH] group, [—(OA)$_m$OH] group,

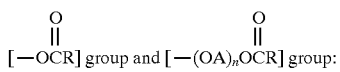

[—OCR] group and [—(OA)$_n$OCR] group:

each bonded to G group at the carbon atom to which an alcoholic hydroxyl group used to be bonded, wherein A group represents $C_2$–$C_4$ alkylene group, R group represents linear or branched $C_7$–$C_{23}$ alkyl or alkenyl group, and m and n are each a number of 0 to 100 corresponding to the average number of alkylene oxide molecules added, a number of m plus n of A's being the same or different from each other, and p, q, r and s: each a number of 0 or above, with the provisos that the sum of p, q, r and s corresponds to the number of alcoholic hydroxyl groups of the starting polyhydric alcohol and that neither the sum of p and q nor that of r and s is 0.

It is preferable that the polyhydric alcohol ester represented by the general formula (5-II) be at least one member selected from the group consisting of the following compounds (a), (b) and (c):

(a) fatty acid esters of pentaerythritol (with the proviso that it has at least one hydroxyl group) and adducts thereof with alkylene oxide (with the proviso that the alkylene group has 2 or 3 carbon atoms), (b) fatty acid esters of glycerol (with the proviso that it has at least one hydroxyl group) and adducts thereof with alkylene oxide (with the proviso that the alkylene group has 2 or 3 carbon atoms), and (c) fatty acid esters of sorbitan (with the proviso that it has at least one hydroxyl group) and adducts thereof with alkylene oxide (with the proviso that the alkylene group has 2 or 3 carbon atoms).

It is preferable that the polyhydric alcohol ester represented by the general formula (5-II) be used in an amount of 1 to 50% by weight based on the total weight of the reactants.

The process (6) is one of preparing a quaternary ammonium salt represented by the general formula (6-I):

(6-I)

(wherein $R^1$ represents linear or branched $C_{20}$–$C_{44}$ alkyl or alkenyl group; $R^2$, $R^3$ and $R^4$ represent the same or different from each other $C_1$–$C_5$ alkyl or hydroxyalkyl group); a is a number of 1 to 6; and $X^-$ represents an anion) by reaction of a corresponding tertiary amine with a quaternizing agent, characterized by conducting the reaction in the presence of a compound represented by the general formula (6-II):

(6-II)

(wherein $R^5$ represents linear or branched $C_7$–$C_{35}$ alkyl or alkenyl group; $A^1$ and $A^2$ represent the same or different from each other $C_2$–$C_4$ alkylene group; and n and m may be the same or different from each other and each represent the average number of alkylene oxide molecules added, with the sum of n and m being 0 to 4, wherein a number "n" of $A^1$'s and a number "m" of $A^2$'s may be the same or different from each other).

It is preferable that the compound to be made coexistent be one represented by the general formula (6-II) wherein $R^5CO$— group is a fatty acid residue resulting from a natural fat or oil and n and m are 0. Further, it is also preferable that the compound represented by the general formula (6-II) be used in an amount of 1 to 50% by weight based on the total weight of the reactants.

[DETAILED DESCRIPTION OF THE INVENTION]

The embodiments of inventions (1) to (6) will now be described successively.

The invention (1) provides a liquid softener composition comprising the following component (1-A) and water, characterized in that the content of the component (1-A) in the composition is 3 to 40% by weight:

component (1-A): a quaternary ammonium salt represented by the general formula (1-I):

(1-I)

[wherein $R^1$ : linear or branched $C_{20}$–$C_{44}$ alkyl or alkenyl group, $R^2$, $R^3$, $R^4$: $C_1$–$C_5$ alkyl or hydroxyalkyl group, wherein $R^2$, $R^3$ and $R^4$ may be the same or different from each other, n: a number of 1 to 6, and X⁻: an anion].

The invention will now be described in detail.

[Component (A)]

In the invention, a quaternary ammonium salt represented by the general formula (1-I) (hereinafter referred to as "quaternary ammonium salt (1-I)") is used as the component (1-A). In the general formula (1-I), X⁻ group represents an anion group and examples thereof include halide anion group (such as Cl⁻ and Br⁻) and $C_1$–$C_5$ alkylsulfate anion group (such as $CH_3SO_4$—, $C_2H_5SO_4$— and $C_3H_7SO_4^-$). Examples of the quaternary ammonium salt (1-I) are as follows:

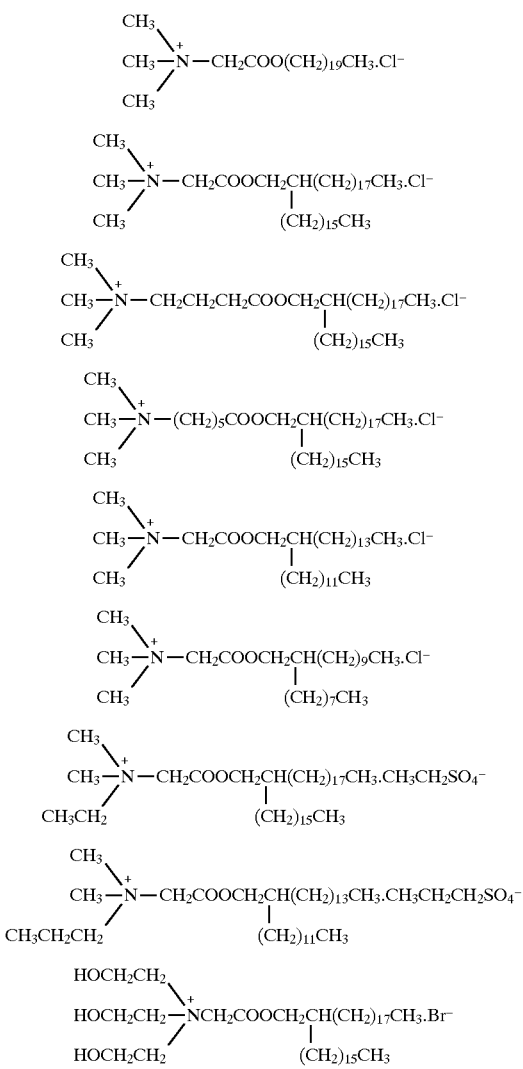

From the standpoint of imparting softness, it is preferable that the quaternary ammonium salt (1-I) be one represented by the general formula (1-I) wherein $R^1$ group is linear or branched $C_{28}$–$C_4$ alkyl group, still preferably linear or branched $C_{36}$–$C_{44}$ alkyl group.

The quaternary ammonium salt (1-I) is particularly preferably one represented by the following general formula (1-I-1)

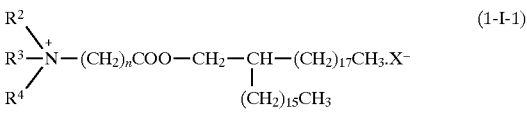

[wherein $R^2$, $R^3$, $R^4$, n, X⁻: each as defined above].

A specific example of the salt represented by the general formula (1-I-1) is one represented by the following formula:

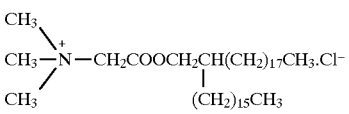

among the quaternary ammonium salts (1-I), salts represented by the following general formula (1-I-2) and those represented by the above general formula (1-I -1) are novel compounds:

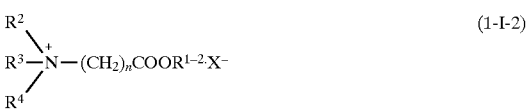

[wherein
$R^{1-2}$: linear or branched $C_{36}$–$C_{44}$ alkyl or alkenyl group
$R^2$, $R^3$, $R^4$, n, X⁻: each as defined above]

In particular, salts of alkyl trimethylglycine quaternary ammonium are preferable.

The quaternary ammonium salt (1-I) can be prepared by, e.g., the following processes 1-1 and 1-2, though the process for preparing the salt (1-I) is not limited to them.

<Preparation process 1- 1>

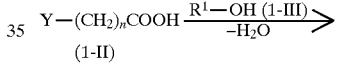

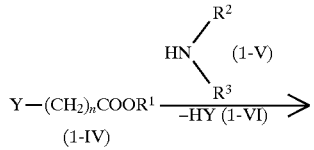

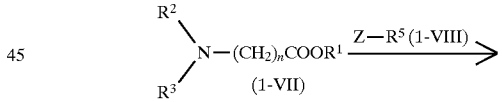

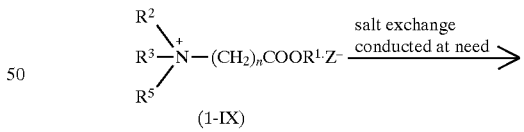

quaternary ammonium salt (1-I)

[wherein
$R^1$, $R^2$, $R^3$, n: each as defined above,
$R^5$: $C_1$–$C_5$ alkyl group
Y: halogen atom, and
Z: a halide anion or a group represented by $R^5SO_4^-$, wherein $R^5$ is as defined above].

Specifically, a halocarboxylic acid (1-II) is first reacted with a higher alcohol (1-III) to form a halocarboxylate ester (1-IV). Examples of the halocarboxylic acid (1-II) to be used in this case include those represented by the following formulae, with monochloroacetic acid being preferable:
$ClCH_2COOH$, $ClCH_2CH_2CH_2COOH$, $Cl(CH_2)_5COOH$, $BrCH_2COOH$ On the other, examples of the higher alcohol (1-III) include those represented by the following formulae, which may be used alone or as a mixture of two or more of them. 2-hexadecyleicosyl alcohol is preferable.

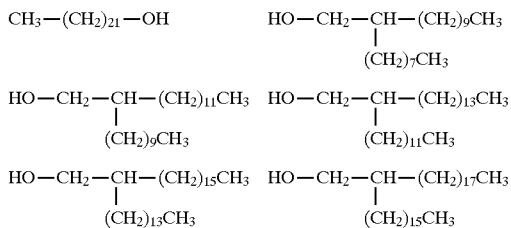

It is preferable that the halocarboxylic acid (1-II) and the higher alcohol (1-III) be charged at a molar ratio of (1-II)/(1-III) of 0.8 to 1.5. The reaction temperature is preferably 120° to 160° C. and the reaction time is preferably 2 to 10 hours.

Then, the halocarboxylate ester (1-IV) thus prepared is reacted with a secondary amine (1-V). Examples of the secondary amine (1-V) include dimethylamine, diethylamine, diethanolamine, methylethanolamine, dipropylamine, di (isopropyl) amine and dibutylamine, among which dimethylamine and diethylamine are preferable.

In this reaction, it is preferable that the halocarboxylate ester (1-IV) and the secondary amine (1-V) be charged at a molar ratio of (1-V) to (1-IV) of 0.8 to 3.0. The reaction temperature is preferably 30° to 80° C. and the reaction time is preferably 3 to 15 hours.

The ester amine (1-VII) thus prepared is then reacted with a quaternizing agent (1-VIII). Examples of the quaternizing agent include alkyl halides (such as methyl chloride and methyl bromide) and dialkyl sulfates (wherein the alkyl group has 1 to 5 carbon atoms), among which methyl chloride and dimethyl sulfate are preferable.

The reaction of the ester amine (1-VII) with a quaternizing agent (1-VIII) is conducted in the presence of a solvent such as isopropanol, ethanol or acetone. It is preferable that the ester amine (1-VII) and the quaternizing agent (1-VIII) be charged at a molar ratio of (1-VII)/(1-VIII) of 0.8 to 1.5. The reaction temperature is preferably 80° to 120° C.

The quaternary ammonium salt (IX) thus prepared is subjected to replacement of counter anion at need to give a quaternary ammonium salt (1-I) according to the invention.
<Preparation process 1-2>

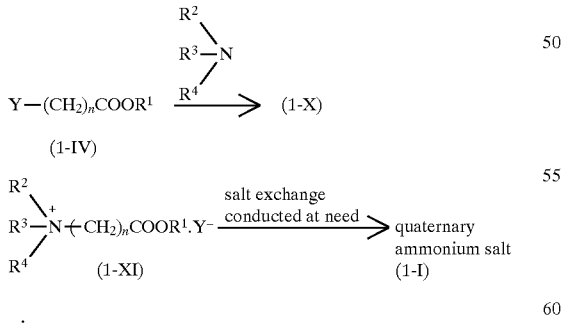

[wherein
R$^1$, R$^2$, R$^3$, R$^4$, n, Y: each as defined above, and
Y$^{31}$ : an halide ion].
Specifically, a halocarboxylate ester (I-IV) is reacted with a tertiary amine (1-X). This reaction may be conducted without any solvent or in the presence of a solvent such as isopropanol, ethanol or acetone. It is preferable that the halocarboxylate ester (1-IV) and the tertiary amine (1-X) be charged at a molar ratio of (1-X)/(1-IV) of 0.8 to 2.5. The reaction temperature is preferably 80° to 160° C.

The quaternary ammonium salt (1-XI) thus prepare is subjected to replacement of counter anion at need to give a quaternary ammonium salt (1I) according to the invention (1).

The invention (2) provides another liquid softener composition comprising the following component (2-A) and water, characterized in that the content of the component (2-A) in the composition is 3 to 40% by weight:

component (2-A): a quaternary ammonium salt represented by the general formula (2-I):

[wherein
R$^1$: linear or branched C$_{20}$–C$_{44}$ alkyl or alkenyl group,
R$^2$, R$^3$, R$^4$: C$_1$–C$_5$ alkyl or hydroxyalkyl group, wherein R$^2$, R$^3$ and R$^4$ may be the same or different from each other,
Y: linear or branched C$_2$–C$_4$ alkylene group
m: a number of 1 to 20 corresponding to the average number of alkylene oxide molecules added,
n: an integer of 1 to 6, and
X$^-$: an anion group].

The invention (2) will now be described in detail.
[component (2-A)]

In the invention, a quaternary ammonium salt represented by the general formula (2-I) (hereinafter referred to as "quaternary ammonium salt (2-I)") is used as the component (2-A). In the general formula (2-I), X$^-$ group represents an anion group and examples thereof include halide anion group (such as Cl$^-$ and Br$^-$) and C$^1$–C$_5$ alkylsulfate anion group (such as CH$_3$SO$_4^-$, C$_2$H$_5$SO$_4^-$ and C$_3$H$_7$SO$_4^-$). Examples of the quaternary ammonium salt (2-I) are as follows:

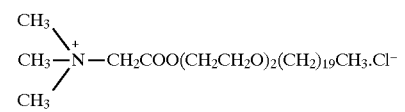

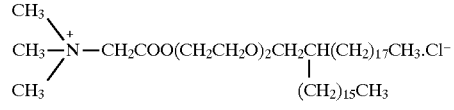

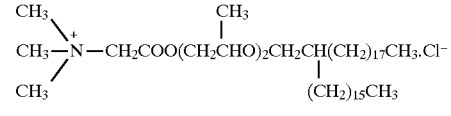

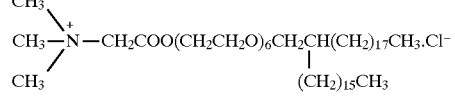

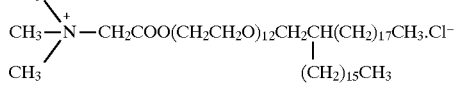

-continued $$CH_3\underset{CH_3}{\overset{CH_3}{\diagdown}}\overset{+}{N}-(CH_2)_3COO(CH_2CH_2O)_2CH_2\underset{|}{CH}(CH_2)_{17}CH_3.Cl^-$$
$$(CH_2)_{15}CH_3$$

$$CH_3\underset{CH_3}{\overset{CH_3}{\diagdown}}\overset{+}{N}-(CH_2)_5COO(CH_2CH_2O)_2CH_2\underset{|}{CH}(CH_2)_{17}CH_3.Cl^-$$
$$(CH_2)_{15}CH_3$$

$$CH_3\underset{CH_3}{\overset{CH_3}{\diagdown}}\overset{+}{N}-CH_2COO(CH_2CH_2O)_5CH_2\underset{|}{CH}(CH_2)_{13}CH_3.Cl^-$$
$$(CH_2)_{11}CH_3$$

$$CH_3\underset{HOCH_2}{\overset{CH_3}{\diagdown}}\overset{+}{N}-CH_2COO(CH_2CH_2O)_2CH_2\underset{|}{CH}(CH_2)_{17}CH_3.CH_3CH_2SO_4^-$$
$$(CH_2)_{15}CH_3$$

$$CH_3\underset{CH_3CH_2}{\overset{CH_3}{\diagdown}}\overset{+}{N}-CH_2COO(CH_2CH_2O)_2CH_2\underset{|}{CH}(CH_2)_{15}CH_3.CH_3CH_2SO_4^-$$
$$(CH_2)_{13}CH_3$$

$$HOCH_2CH_2\underset{HOCH_2CH_2}{\overset{HOCH_2CH_2}{\diagdown}}\overset{+}{N}-CH_2COO(CH_2CH_2O)_2CH_2\underset{|}{CH}(CH_2)_{17}CH_3.Br^-$$
$$(CH_2)_{15}CH_3$$

Among the quaternary ammonium salts (2-I), those wherein $R^1$ group is linear or branched $C_{28}$–$C_{44}$ alkyl or alkenyl group and Y is ethylene group are preferable from the standpoint of imparting softness, with those represented thereby wherein $R^1$ group is a group represented by the formula:

$$-CH_2-\underset{|}{CH}-(CH_2)_p-CH_3$$
$$(CH_2)_{p-2}-CH_3$$

(wherein p is a number of 9 to 21) and Y is ethylene group being still preferable.

In the general formula (2-I), $R^2$, $R^3$ and $R^4$ are preferably methyl group; n is preferably 1; and m is preferably 1 to 8, still preferably 2 to 5.

The quaternary ammonium salt (2-I) is particularly preferably one represented by the following general formula (2-I-1):

$$R^3\underset{R^4}{\overset{R^2}{\diagdown}}\overset{+}{N}-(CH_2)_n-COO-(CH_2CH_2O)_m-CH_2-\underset{|}{CH}-(CH_2)_{17}-CH_3.X^- \quad (2\text{-}I\text{-}1)$$
$$(CH_2)_{15}-CH_3$$

[wherein $R^2$, $R^3$, $R^4$, n, m, $X^-$: each as defined above].

A specific example of the salt represented by the general formula (2-I-1) is one represented by tire following formula:

$$CH_3\underset{CH_3}{\overset{CH_3}{\diagdown}}\overset{+}{N}-CH_2COO(CH_2CH_2O)_2CH_2\underset{|}{CH}(CH_2)_{17}CH_3.Cl^-$$
$$(CH_2)_{15}CH_3$$

Among the quaternary ammonium salts (2-I), salt represented by the following general formula (2-I-2) and those represented by the above general formula (2-I-1) are novel compounds:

$$R^3\underset{R^4}{\overset{R^2}{\diagdown}}\overset{+}{N}-(CH_2)_n-COO+YO)_m R^{1\text{-}2}.X^- \quad (2\text{-}I\text{-}2)$$

[wherein $R^{1\text{-}2}$: linear or branched $C_{36}$–$C_{44}$ alkyl or alkenyl group, and $R^2$, $R^3$, $R^4$, Y, n, m, $X^-$: each as defined above]

The quaternary ammonium salt (2-I) can be prepared by, e.g., the following processes 2-1 and 2-2, though the process for preparing the salt (2-I) is not limited to them.

<Preparation process 2-1>

$$Z-(CH_2)_n-COOH\xrightarrow{R^1+OY)_m OH \quad (2\text{-}III)}_{-H_2O}$$
(2-II)

$$Z-(CH_2)_nCOO+YO)_m R^1 \xrightarrow{HN\underset{R^3}{\overset{R^2}{\diagdown}} \quad (2\text{-}V)}_{-HZ \quad (2\text{-}VI)}$$
(2-IV)

$$R^3\underset{}{\overset{R^2}{\diagdown}}N-(CH_2)_n-COO+YO)_m R^1 \xrightarrow{W-R^5 \quad (2\text{-}VIII)}$$
(2-VII)

$$R^3\underset{R^5}{\overset{R^2}{\diagdown}}\overset{+}{N}-(CH_2)_n-COO+YO)_m R^1.W^- \xrightarrow{\text{salt exchange conducted at need}}$$
(2-IX)

quaternary ammonium salt (2-I)

[wherein $R^1$, $R^2$, $R^3$, Y, n, m: each as defined above, $R^5$: $C_1$–$C_5$ alkyl group, Z: halogen atom, and $W^-$: a halide anion or a group represented by $R^5SO_4^-$ wherein $R^5$ is as defined above].

Specifically, a halocarboxylic acid (2-II) is first reacted with an adduct (2-III) of higher alcohol with alkylene oxide to form a halocarboxylate ester (2-IV). Examples of the halocarboxylic acid (2-II) to be used in this case include those represented by the following formulae, with monochloroacetic acid being preferable:

$ClCH_2COOH$, $ClCH_2CH_2CH_2COOH$  $Cl(CH_2)_5COOH$, $BrCH_2COOH$

On the other hand, examples of the adduct (2-III) of higher alcohol with alkylene oxide include those represented by the following formulae, which may be used alone or as a mixture of two or more of them. Adducts or 2-hexadecyleicosyl alcohol with alkylene oxide (particularly ethylene oxide) are preferable.

$$CH_3(CH_2)_{21}(OCH_2CH_2)_2OH$$

$$CH_3(CH_2)_9\underset{|}{CH}CH_2(OCH_2CH_2)_{12}OH$$
$$(CH_2)_7CH_3$$

$$CH_3(CH_2)_{11}\underset{|}{CH}CH_2(OCH_2CH_2)_{12}OH$$
$$(CH_2)_9CH_3$$

$$CH_3(CH_2)_{13}\underset{|}{CH}CH_2(OCH_2CH_2)_6OH$$
$$(CH_2)_{11}CH_3$$

$CH_3(CH_2)_{15}\underset{|}{C}HCH_2(OCH_2CH_2)_6OH$
$(CH_2)_{13}CH_3$ $CH_3(CH_2)_{17}\underset{|}{C}HCH_2(OCH_2CH_2)_2OH$
$(CH_2)_{15}CH_3$ $CH_3(CH_2)_{17}\underset{|}{C}HCH_2(OC\underset{|}{H_2}\overset{CH_3}{C}H)_2OH$
$(CH_2)_{15}CH_3$ $CH_3(CH_2)_{17}\underset{|}{C}HCH_2(OCH_2CH_2)_5OH.$
$(CH_2)_{15}CH_3$ It is preferable that the halocarboxylic acid (2-II) and the adduct (2-III) be charged at a molar ratio of (2-II)/(2-III) of 0.8 to 1.5. The reaction temperature is preferably 120° to 160° C. and the reaction time is preferably 2 to 10 hours.

Then, the halocarboxylate ester (2-IV) thus prepared is reacted with a secondary amine (2-V). Examples of the secondary amine (2-V) include dimethylamine, diethylamine, diethanolamine, methylethanolamine, dipropylamine, di (isopropyl) amine and dibutylamine, among which dimethylamine and diethylamine are preferable.

In this reaction, it is preferable that the halocarboxylate ester (2-IV) and the secondary amine (2-V) be charged at a molar ratio of (2-V)/(2-IV) of 0.8 to 3.0. The reaction temperature is preferably 30 to 80° C. and the reaction time is preferably 3 to 15 hours.

The ester amine (2-VII) thus prepared is then reacted with a quaternizing agent (2-VIII). Examples of the quaternizing agent include alkyl halides (such as methyl chloride and methyl bromide) and dialkyl sulfates (wherein the alkyl group has 1 to 5 carbon atoms), among which methyl chloride and dimethyl sulfate are preferable.

The reaction of the ester amine (2-VII) with the quaternizing agent (2-VIII) is conducted in the presence of a solvent such as isopropanol, ethanol or acetone. It is preferable that the ester amine (2-VII) and the quaternizing agent (2-VIII) be charged at a molar ratio of (2-VII)/(2-VIII) of 0.8 to 1.5. The reaction temperature is preferably 80° to 120° C.

The quaternary ammonium salt (2-IX) thus prepared is subjected to replacement of counter ion at need to give a quaternary ammonium salt (2-I) according to the invention (2).

<Preparation process 2-2>

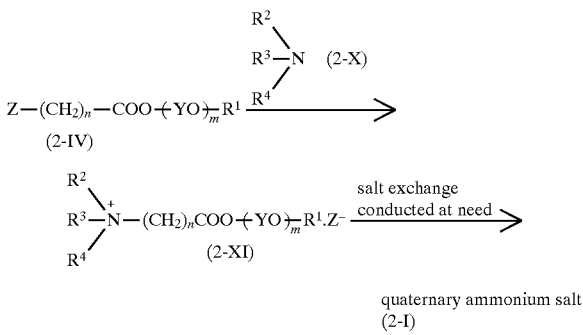

[wherein
R$^1$, R$^2$, R$^3$, R$^4$, Y, n, m, Z: each as defined above, and
Z$^-$: a halide ion]

Specifically, a halocarboxylate ester (2-IV) is reacted with a tertiary amine (2-X). This reaction may be conducted without any solvent or in the presence of a solvent such as isopropanol, ethanol or acetone, if necessary. It is preferable that the halocarboxylate ester (2-IV) and the tertiary amine (2-X) be charged at a molar ratio of (2-X)/(2-IV) of 0.8 to 2.5. The reaction temperature is preferably 40° to 120° C. still preferably 50° to 800° C.

The quaternary ammonium salt (2-XT) thus prepared is subjected to replacement of counter ion at need to give a quaternary ammonium salt (2-I) according to the invention (2)

[Softener composition]

The softener composition (1) according to the present invention comprises 3 to 40% by weight, preferably 5 to 30% by weight, still preferably 10 to 30% by weight of the component (1-A) and the balance of water.

When the amount of the quaternary ammonium salt (1-I) is less than 3% by weight, the desirable softening effect according to the present invention will not be attained, while when it exceeds 40% by weight, the resulting composition will be poor in handleability because of its too high viscosity.

The composition (1) may further contain a linear or branched, saturated or unsaturated $C_8$–$C_{44}$ alcohol as component (1-B) to improve the softening effect and storage stability of the composition. The amount of the component (1-B) added is at most 110% by weight, preferably 1 to 100% by weight based on the component (1-A).

Example of the linear or branched, saturated or unsaturated $C^8$–$C_{44}$ alcohol to be added as the component (1-B) include the following:

$CH_3(CH_2)_{21}OH$  $HOCH_2\underset{|}{C}H(CH_2)_9CH_3$
$(CH_2)_7CH_3$ $HOCH_2\underset{|}{C}H(CH_2)_{11}CH_3$  $HOCH_2\underset{|}{C}H(CH_2)_{13}CH_3$
$(CH_2)_9CH_3$ $(CH_2)_{11}CH_3$ $HOCH_2\underset{|}{C}H(CH_2)_{15}CH_3$  $HOCH_2\underset{|}{C}H(CH_2)_{17}CH_3$
$(CH_2)_{13}CH_3$ $(CH_2)_{15}CH_3$ $CH_3(CH_2)_7CH=CH(CH_2)_8OH$ Further, the softener composition (1) according to the invention may further contain a linear or branched, saturated or unsaturated $C_8$–$C_{36}$ fatty acid as component (1-C) to improve the softening effect and storage stability of the composition. The amount of the component (1-C) added is at most 100% by weight, preferably 0.5 to 50% by weight based on the component (1-A).

Examples of the fatty acid to be used as the component (1-C) include stearic acid, palmitic acid, myristic acid, lauric acid, caprinic acid, caprylic acid, oleic acid, isostearic acid and fatty acids having alkyl composition resulting from natural fats and oils such as coconut oil, palm oil, tallow, rape seed oil and fish oil.

The composition (1) according to the present invention may contain a $C_1$–$C_4$ monohydric alcohol as component (1-D) for the purpose of controlling the viscosity of the composition and improving the storage stability thereof (i.e., protecting the composition from gelation). The amount of the component (1-D) in the composition (1) according to the invention to be added is at most 60% by weight, preferably 5 to 50% by weight, still preferably 10 to 45% by weight based on the component (1-A).

Examples of the $C_1$–$C_4$ monohydric alcohol usable as the component (1-D) include methyl alcohol, ethyl alcohol, propyl alcohol, isopropyl-alcohol and butyl alcohol.

The composition (1) according to the present invention may contain one or more members selected from among conventional cation compounds (such as quaternary ammonium salts and imidazolinium salts), esters and amides as softener base material. Examples of the compound to be used in this case include quaternary ammonium salts represented by the following general formula (1-XXI) and compounds represented by the following general formulae (1-XXII-1) to (1-XXII-8):

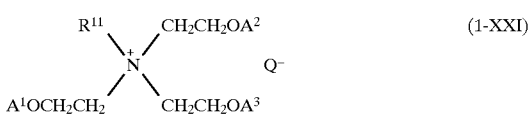

[wherein
$R^{11}$: $C_1$–$C_4$ alkyl or hydroxyalkyl group, $A^1$, $A^2$, $A^3$: H atom or $R^{12}CO$— (wherein $R^{12}$ represents linear or branched $C_7$–$C_{35}$ alkyl or alkenyl group), with the proviso that at least one of $A^1$, $A^2$ and $A^3$ is a group represented by $R^{12}CO$— (wherein $R^{12}$ is as defined above), though $A^1$, $A^2$ and $A^3$ may be the same or different from each other, and $Q^-$: an anion]

The anion as defined with respect to $Q^-$ includes halide anions such as $Cl^-$ and $Br^-$ and $C_1$–$C_5$ alkylsulfate group.

With respect to the composition (1) according to the present invention, the anion $Q^-$ constituting the quaternary ammonium salt represented by the general formula (1-XXI) may be the same as or different from the anion $X^-$ constituting the quaternary ammonium salt (1-I) used simultaneously therewith.

Among the compositions (1) according to the present invention, one containing the component (1-A) in a higher concentration tends to thicken during storage. In order to inhibit this thickening it is preferable to add, as component (1-E), a polyether compound prepared by addition reaction of a compound having at least three active hydrogen atoms with ethylene oxide and, if necessary, propylene oxide and/or trimethylene oxide which has a weight-average molecular weight of 5,000 to 2,000,000 and in which the total amount of oxyethylene chain moieties accounts for at least 55% by weight of the molecular weight, or a derivative of the polyether compound.

Examples of the compound having at least three active hydrogen atoms to be used in the preparation of the component (1-E) as starting material include polyhydric alcohols such as trimethylolpropane, diethanolamine, triethanolamine, glycerol, pentaerythritol, sorbitol, sucrose, polyglycerol, polyvinyl alcohol and partially saponified polyvinyl acetate; polyhydric phenols such as phenolic resin and alkylphenol-formalin condensate; polyamines such as ethylenediamine and diethylenetriamine; and polyethyleneimines such as triethylenetetramine, tetraethylenepentamine and pentaethylenehexamine. Further, partial amidation products of these polyamines and N-alkylation products thereof which are derivatives of the polyamine compounds can be used in the preparation of the component (1-E), as far as they each have at least three active hydrogen atoms.

The component (1-E) can be prepared by conventional addition reaction of a compound having at least three active hydrogen atoms with ethylene oxide and, if necessary, propylene oxide and/or trimethylene oxide. The component (1-E) is preferably an adduct or such a compound with ethylene oxide alone, a block adduct thereof with ethylene oxide and propylene oxide or a partial block adduct thereof with ethylene oxide and propylene oxide. In preparing an adduct of a compound having at least three active hydrogen atoms with two or more alkylene oxides, it is preferable in order to prepare a composition (1) which contains the component (1-A) in an enhanced concentration and is prevented from thickening in storage that the addition of the compound with propylene oxide (hereinafter abbreviated at "PO") be first conducted, followed by the addition with ethylene oxide (hereinafter abbreviated at "EO") though the addition with either of PO and EO may be conducted antecedently.

The molecular weight of the component (1-E) ranges from 5,000 to 2,000,000, preferably 10,000 to 100,000. Further, the total amount of oxyethylene (EO) chain moieties accounts for at least 55% by weight, preferably at least 80% by weight of the molecular weight.

When the molecular weight of the component (1-E) is less than 5,000, the resulting softener composition will little be inhibited from thickening during storage, while when it exceeds 2,000,000, the resulting softener composition will have too high a viscosity to be easily taken out of a bottle unfavorably.

When the ratio of the total weight of the oxyethylene chain moieties to the molecular weight of component (1-E) is less than 55% by weight, the resulting softener composition will little be inhibited from thickening in storage.

The above polyether compound derivative to be used as the component (1-E) includes products of crosslinking of the above polyether compounds with compounds having isocyanate group; wherein terminal hydroxyl group is sulfated, phosphated, carboxyalkylated and fatty acid-esterified derivatives of the above polyether compounds; and products of partial N-cationization of the above polyether compounds, among which fatty acid-esterified derivatives of the polyether compounds and products of partial N-cationization thereof are preferable.

The fatty acid to be used in the preparation of the fatty acid-esterified derivatives is preferably one having 7 to 23 carbon atoms, and the number of double bonds or the presence of branch has little influence on the performance of the resulting softener composition.

The products of partial N-cationization of the polyether compounds include compounds prepared by partially cationizing the nitrogen of the polyether compounds with dialkyl sulfates and alkyl halides, and cation compounds prepared by neutralizing the compounds obtained by the above partial N-cationization with acetic acid and alkylbenzene sulfonic acids.

The softener composition (1) according to the present invention may contain the component (3-E) in an amount of 0.5 to 5% by weight, preferably 1 to 3% by weight based on the composition. The weight ratio of the component (1-E) to the component (1-A) ranges from 1/100 to 1/2.5, preferably 1./50 to 1/5. The total amount of the components (1-A) and (1-E) is 4 to 45% by weight, preferably 11 to 39% by weight, still preferably 14 to 32% by weight based on the composition (1). When the amount of the component (1-E) lies within the above range, the softener composition (1) according to the present invention exhibits a desirable softening effect and is inhibited from thickening during storage.

The composition (1) according to the present invention may further contain an inorganic electrolyte such as NaCl, $CaCl_2$ or $MgCl_2$ to control the viscosity thereof. The amount of the inorganic electrolyte to be added in this case is 0 to 2% by weight, preferably 0.01 to 1% by weight based on the composition.

The softener composition (1) according to the present invention may further contain an acidic or alkaline substance to adjust its pH. It is desirable in respects of the viscosity and storage stability of the composition that an acidic or alkaline substance is added in such a way that the pH of the composition falls in the range of 1.5 to 6.5.

Although the softener composition (1) of the present invention is excellent in long-term storage stability, it may further contain a nonionic surfactant such as polyoxyethylene(P=5 to 50) alkyl or alkenyl($C_{12}$–$C_{24}$) ether or polyoxyethylene(p=5 to 50) alkyl or alkenyl ($C_{12}$–$C_{24}$) amine or a hydrotrope agent such as ethylene glycol, propylene glycol or urea in order to improve the storage stability thereof under severer conditions.

The composition (1) according to the present invention may further contain a pigment or dye for the purpose of improving its appearance, a silicone for the purpose of inhibiting the composition from foaming in rinsing, and/or a perfume for the purpose of improving the comfortableness of the composition in use and the confortableness of the textile treated with the composition.

A process for preparing the softener composition (1) according to the present invention will now be described, though the process for the preparation thereof is not limited to this process.

The component (1-A) alone or a mixture of the component (1-A) with the other components (except the component (1-E)) is molten and the obtained melt is gradually dropped into deionized water kept at 60° C. under stirring to form an emulsion. Thereafter, the component (1-E) is added to the emulsion at need. An aqueous solution of a nonionic surfactant may be used instead of the deionized water, and an inorganic salt may be added after the completion of the addition of the components (1-A) to (1-E) for the purpose of controlling the viscosity of the composition.

The softener composition (1) according to the present invention can impart sufficient softness and antistatic properties and excellent elasticity to various textiles, exhibits excellent storage stability (i.e., little causes gelation or thickening during storage and little suffers from hydrolysis of the softener base material ever after storage) and is extremely excellent in water absorption properties.

The softener composition (2) according to the present invention comprises 3 to 40% by weight, preferably 5 to 30% by weight, still preferably 10 to 30% by weight of the quaternary ammonium salt (2-I) as the component (2-A) and the balance of water.

When the amount of the quaternary ammonium salt (2-I) is less than 3% by weight, the desirable softening effect according to the present invention will not be attained, while when it exceeds 40% by weight, the resulting composition will be poor in handleability because of its too high viscosity.

The composition(2) may further contain a linear or branched, saturated or unsaturated $C_8$–$C_{44}$ alcohol, preferably Guerbet alcohol represented by the formula:

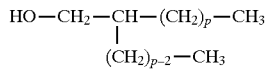

(wherein p is as defined above) as component (2-B) to improve the softening effect and storage stability of the composition. The amount of the component (2-B) added is at most 110% by weight, preferably 1 to 100% by weight based on the component (2-A).

Examples of the linear or branched, saturated or unsaturated $C_8$–$C_{44}$ alcohol to be used as the component (2-B) include the following:

$CH_2(CH_2)_{21}OH$  $HOCH_2CH(CH_2)_9CH_3$  $HOCH_2CH(CH_2)_{11}CH_3$
                    |                       |
                    $(CH_2)_7CH_3$          $(CH_2)_9CH_3$

-continued $HOCH_2CH(CH_2)_{13}CH_3$  $HOCH_2CH(CH_2)_{15}CH_3$  $HOCH_2CH(CH_2)_{17}CH_3$
|                          |                          |
$(CH_2)_{11}CH_3$          $(CH_2)_{13}CH_3$          $(CH_2)_{15}CH_3$ $CH_3(CH_2)_7CH=CH(CH_2)_8OH$ Further, the softener composition (2) may further contain a linear or branched, saturated or unsaturated fatty acid having 8 to 36, preferably 12 to 20, still preferably 14 to 18 carbon atoms as component (2-C) to improve the softening effect and storage stability of the composition. The amount of the component (2-C) added is at most 100% by weight, preferably 0.5 to 50% by weight based on the component (2-A).

Examples of the fatty acid to be used as the component (2-C) include stearic acid, palmitic acid, myristic acid, lauric acid, caprinic acid, caprylic acid, oleic acid, isostearic acid, and fatty acids resulting from natural fats and oils such as coconut oil, palm oil, tallow, rape seed oil and fish oil, among which hardened tallow fatty acid, stearic acid and palmitic acid are preferable.

The composition (2) according to the present invention may contain a $C_1$–$C_4$ monohydric alcohol as component (2-D) for the purpose of controlling the viscosity of the composition and improving the storage stability thereof (i.e., inhibiting the composition from gelation). The amount of the component (2-D) to be added is at most 60% by weight, preferably 5 to 50% by weight, still preferably 10 to 45% by weight based on the component (2-A).

Examples of the $C_1$–$C_4$ monohydric alcohol to be used as the component (2-D) include methyl alcohol, ethyl alcohol, propyl alcohol, isopropyl alcohol and butyl alcohol, among which $C_2$–$C_3$ monohydric alcohols are preferable.

The invention (3) provides a liquid softener composition comprising the following components (3-A) and (3-B) at a weight ratio of (3-A)/(3-B) of 2/1 to 1/9:

[component (3-A)]

a mixture comprising a compound represented by the following general formula (3-I) (hereinafter referred to as "compound (3-I)"), a compound represented by the following general formula (3-II) (hereinafter referred to as "compound (3-II)"), a compound represented by the following general formula (3-III) (hereinafter referred to as "compound (3-III)"), and a compound represented by the following general formula (3-IV) (hereinafter referred to as "compound (3-IV)"), with the provisos that the mixing ratio by weight of the compounds (3-I), (3-II), (3-III) and (3-IV) must satisfy the following relationships:

[compound (3-I)]/[the sum total of the compounds (3-I), (3-II), (3-III) and (3-IV)]=0.040 to 0.527,

[compound (3-II)]/[the sum total of the compounds (3-I) (3-II) (3-III) and (3-IV)]=0.133 to 0.469,

[compound (3-III)]/[the sum total of the compounds (3-I), (3-II), (3-III) and (3-IV)]=0.013 to 0.661, and

[compound (3-IV)]/[the sum total of the compounds (3-I) (3-II), (3-III) and (3-IV)]=0.001 to 0.417, and that the mixture comprising the compounds (3-I), (3-II), (3-III) and (3-IV) has a Griffin's HLB value of 5 to 5:

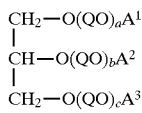
(3-I)

[wherein
$A^1, A^2, A^3$: RCO group or H atom, wherein R group represents linear or branched $C_7$–$C_{23}$ alkyl or alkenyl group, with little proviso that one of $A^1, A^2$ and $A^3$ is RCO group and the others thereof are H atom,
Q: $C_2$–$C_3$ alkylene group or a mixture of $C_2$ alkylene group with $C_3$ alkylene group, and
a, b, c: a number of 0 or above, with the proviso that the sum of a, b and c is 1 to 50 on an average],

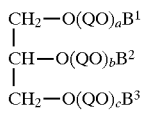
(3-II)

[wherein
$B^1, B^2, B^3$: RCO group or H atom, wherein R group is as defined above, with the proviso that two of $B^1, B^2$ and $B^3$ are ROC group and the other thereof is H atom, and
Q, a, b, c: each as defined above],

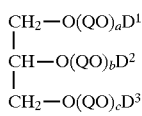
(3-III)

[wherein
$D^1, D^2, D^3$: RCO group wherein R group is as defined above, and
Q, a, b, c: each as defined above], and

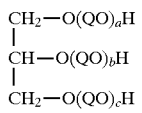
(3-IV)

[wherein Q, a, b, c: each as defined above], and
[component (3-B)]
a quaternary ammonium salt represented by the following general formula (3-V):

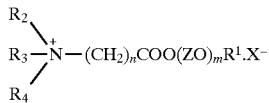
(3-V)

[wherein
$R^1$: linear or branched $C_{20}$–$C_{44}$ alkyl or alkenyl group,
$R^2, R^3, R^4$: $C_1$–$C_5$ alkyl or hydroxyalkyl group, wherein $R^2, R^3$ and $R^4$ may be the same or different from each other,
Z: $C_2$–$C_3$ alkylene group or a mixture of $C_2$ alkylene group with $C_3$ alkylene group,
m: a number of 0 to 20,
n: a number of 1 to 6, and
$X^-$: an anion group].

The invention (3) will now be described in detail.
[Component (3-A)]

The mixing ratio of the compounds (3-I), (3-II), (3-III) and (3-IV) constituting the component (3-A) must satisfy the following relationships: the weight ratio of the compound (3-I) to the sum total of the compounds (3-I), (3-II), (3-III) and (3-IV) is 0.040 to 0.527, preferably 0.040 to 0.346, still preferably 0.040 to 0.327; that of the compound (3-II) to the sum total of the compounds (3-I), (3-II), (3-III) and (3-IV) is 0.133 to 0.469, preferably 0.298 to 0.469; that of the compound (3-III) to the sum total of the compounds (3-I), (3-II), (3-III) and (3-IV) is 0.013 to 0.661, preferably 0.154 to 0.661, still preferably 0.173 to 0.661; and that of the compound (3-IV) to the sum total of the compounds (3-I), (3-II), (3-III) and (3-IV) is 0.001 to 0.417, preferably 0.001 to 0.096, still preferably 0.001 to 0.077.

When the mixing ratio is outside the widest range defined above, the resulting softener composition will be poor in stability. The reason for this phenomenon is presumed to be as follows: a mixture comprising the compounds (3-I), (3-II), (3-III) and (3-IV) at a ratio falling within the above range has a lowered crystallinity of the component (3-A) so that a softener composition containing the mixture is inhibited from the precipitation of the component (3-A) to cause neither thickening nor gelation nor appearance change, though the reason is not always apparent.

In the general formulae (3-I), (3-II), (3-III) and (3-IV), the sum of a, b and c is 1 to 50, preferably 4 to 18 on an average. When the sum is less than 1 on an average, no stable softener composition will be obtained, while when it exceeds 50, the desirable softening effect according to the present invention will not be attained.

It is important that the Griffin's HLB value of the component (3-A) is 5 to 15, preferably 5.6 to 12. When the Griffin's HLB value is less than 5, no stable softener composition will be obtained, while when it exceeds 15, no satisfactory softening effect will be attained.

The Griffin's HLB value of a fatty acid ester of polyhydric alcohol is calculated by the following formula:

$$\text{Griffin's HLB} = 20 \times (1 - S/A)$$

[wherein
S: saponification value (mg KOH/G) of the fatty acid ester of polyhydric alcohol, and
A: acid value (mg KOH/G) of the fatty acid constituting the fatty acid ester of polyhydric alcohol]

In the general formulae (3-I) to (3-III), R group is preferably at least one member selected from the group consisting of alkyl group resulting from coconut oil fatty acid, alkyl group resulting from palm kernel oil fatty acid, alkyl group resulting from palm oil fatty acid, alkyl group resulting from palm stearic acid, alkyl group resulting from hardened palm stearic acid, alkyl group resulting from tallow fatty acid, and alkyl group resulting from hardened tallow fatty acid, preferably at least one member selected from the group consisting of alkyl group resulting from tallow fatty acid, alkyl group resulting from hardened tallow fatty acid, alkyl group resulting from palm stearic acid, and alkyl group resulting from hardened palm stearic acid.

The component (3-A) can be prepared by, e.g., the following synthesis processes (3-i) to (3-iv).

Synthesis process (3-i)

The component (3-A) can be prepared by esterifying glycerol with a fatty acid and conducting the addition reaction of the obtained ester with ethylene oxide and/or propylene oxide. When the addition reaction of the ester with both ethylene oxide and propylene oxide is conducted, it is preferable that the addition reaction with propylene oxide be conducted antecedently, followed by the addition reaction with ethylene oxide, though the addition reaction with either of ethylene oxide arid propylene oxide may be conducted antecedently or the addition reaction with ethylene oxide may be conducted simultaneously with that with propylene oxide. Further, it is preferable that the number of propylene oxide molecules added be at most 3 moles per each glycerol skeleton.

In the synthesis process (3-i), the esterification may be conducted without any catalyst or in the presence of an acid catalyst such as sulfuric acid, hydrochloric acid or p-toluenesulfonic acid. The fatty acid to be used in the esterification include caprinic acid, lauric acid, myristic acid, palmitic acid, oleic acid, stearic acid, isostearic acid, arachidic acid, behenic acid and fatty acids resulting from coconut oil, palm kernel oil, unhardened and hardened tallow, lard, palm oil, rape seed oil, fish oil, palm stearin and hardened palm stearin, which may be used alone or as a mixture of two or more of them. Among these fatty acids, it is preferable to use one or more members selected from among coconut oil fatty acid, palm kernel oil fatty acid, palm oil fatty acid, unhardened and hardened tallow fatty acids, and unhardened and hardened palm stearic acids.

The addition reaction of the obtained ester with alkylene oxide is conducted in the presence of a catalyst such as NaOH, KOH, NaOCH$_3$, KOCH$_3$ or alkali metal salt of fatty acid. It is preferable that such a catalyst be added in an amount exceeding the amount necessary for the addition reaction by that required for the neutralization of the acid catalyst used for the above esterification.

Synthesis process (3-ii)

The component (3-A) can be prepared by transesterifying a fatty acid ester with glycerol and conducting the addition reaction of the obtained ester with an alkylene oxide.

The catalyst to be used in the transesterification includes NaOH, KOH, NaOCH$_3$, KOCH$_3$ and so forth.

The fatty acid ester to be used in the process (3-ii) includes esters of the fatty acids described in the section "Synthesis process (3-i)" with methanol, ethanol, propanol, butanol, ethylene glycol, glycerol, erythritol, pentaerythritol, xylitol, sorbitol and sorbitan.

Among these esters, the following are preferable:

R—COOCH$_3$, R—COOCH$_2$CH$_3$,

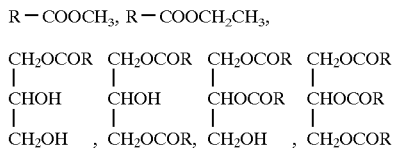

[wherein R is as defined above]

The addition reaction with alkylene oxide in the synthesis process (3-ii) is conducted by the use of a catalyst such as NaOH, KOH, NaOCH$_3$, KOCH$_3$ or alkali metal salt of fatty acid. The catalyst used in the preceding transesterification may be used as such successively. The kind of alkylene oxide and the order of addition thereof may be the same as described in the section "Synthesis process (3-i)".

Synthesis process (3-iii)

The component (3-A) can be prepared by conducting the addition reaction of glycerol with an alkylene oxide and esterifying the obtained adduct with a fatty acid.

In this process (3-iii), the addition reaction with an alkylene oxide and the esterification may be conducted under the same conditions as those of Synthesis process (3-i).

Further, the fatty acid to be used in the esterification of this process may be the same as described in the section "Synthesis process (i)".

Synthesis process (3-iv)

The component (3-A) can be prepared by conducting the addition reaction of glycerol with an alkylene oxide and transesterifying the obtained adduct with a fatty acid ester.

In this process (3-iv) the addition reaction with an alkylene oxide and the transesterification may be conducted under the same conditions as those of Synthesis process (3-ii).

The fatty acid ester to be used in the transesterification in Synthesis process (3-iv) includes the following:

R—COOCH$_3$, R—COOCH$_2$CH$_3$

[wherein R is as defined above]

Specific examples of the component (3-A) include adducts of mixtures comprising glycerides of tallow fatty acid and glycerol with alkylene oxides, adducts of mixtures comprising glycerides of mixtures comprising partially hardened tallow fatty acid and glycerol with alkylene oxides, adducts of mixtures comprising glycerides of palm stearic acid and glycerol with alkylene oxides, adducts of mixtures comprising glycerides of hardened palm stearic acid and glycerol with alkylene oxides, adducts of mixtures comprising glycerides of lauric acid and glycerol with alkylene oxides, adducts of mixtures comprising glycerides of palm kernel oil fatty acid and glycerol with alkylene oxides, adducts of mixtures comprising glycerides of coconut oil fatty acid and glycerol with alkylene oxides and adducts of mixtures comprising glycerides of palm oil fatty acid and glycerol with alkylene oxides. It is preferable the alkylene oxide be ethylene oxide.

[Component (3-B)]

In the invention (3), a quaternary ammonium salt represented by the above general formula (3-V) (hereinafter referred to as quaternary ammonium salt (3-V)) is used as component (3-B). In the general formula (3-V), X$^-$ group represents an anion group and examples thereof include halide anion groups (such as Cl$^-$ and Br$^-$) and C$^1$–C$_5$ alkylsulfate anion groups (such as CH$_3$SO$_4^-$, C$_2$H$_5$SO$_4^-$ and C$_3$H$_7$SO$_4^-$).

Examples of the quaternary ammonium salt (3-V) to be used in the invention (3) are as follows:

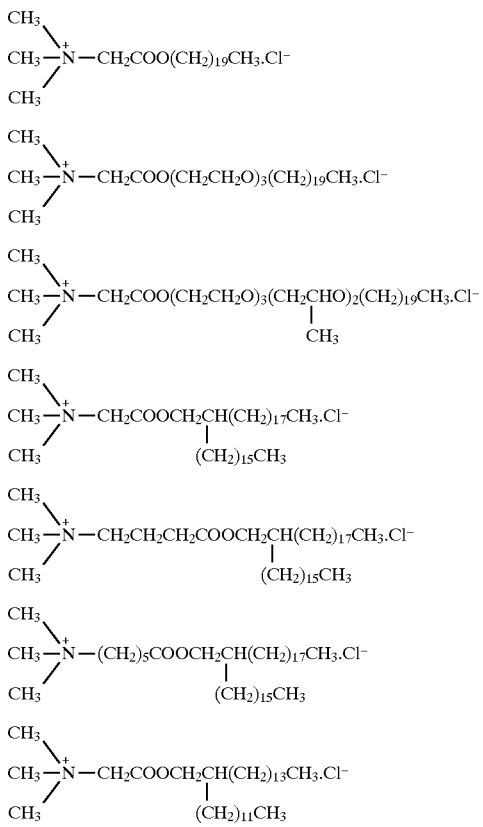

-continued

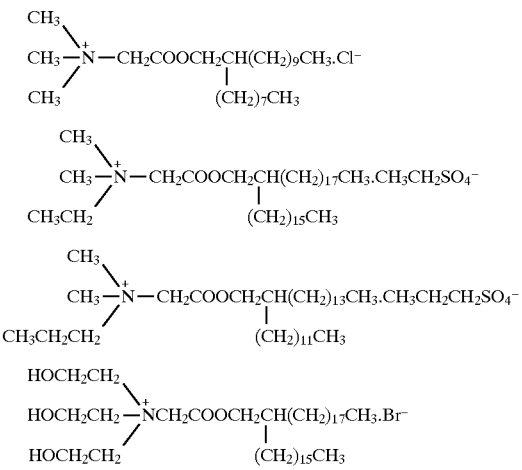

Among these salts, it is preferable from the standpoint of imparting softness to use a quaternary ammonium salt represented by the general formula (3-V) wherein $R^1$ group is a linear or branched alkyl or alkenyl group having 28 to 44, still preferably 36 to 44 carbon atoms.

Particularly preferable examples of the quaternary ammonium salt (3-V) include those represented by the following general formula (3-V-1):

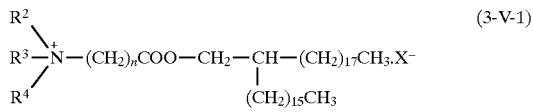

[wherein $R^2$, $R^3$, $R^4$, n, $X^-$: each as defined above].

A specific example of the salt represented by the general formula (3-V-1) is one represented by the following formula:

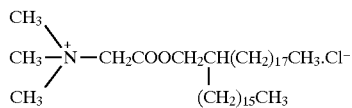

[Softener composition]

composition (3) according to the invention will now be described.

The composition (3) comprises the above components (3-A) and (3-B) and water.

The weight ratio of the component (3-A) to the component (3-B) is 2/1 to 1/9, preferably 1/1 to 1/9, still preferably 1/2 to 1/9. When the weight ratio falls in the above range, an excellent softening effect can be attained.

The total amount of the softener bases, i.e., the components (3-A) and (3-B) is 3 to 400% by weight, preferably 5 to 30% by weight, still preferably 5 to 25% by weight based on the composition. When the total amount is less than 3% by weight, the desirable softening effect according to the present invention will not be attained, while when it exceeds 40% by weight, the resulting composition will have too high a viscosity to be easily taken out of a bottle unfavorably.

For the purpose of further improving the softening effect and storage stability of the composition (3), a linear or branched, saturated or unsaturated $C_8$–$C_{44}$ alcohol may be further added as component (3-C). The amount of the component (3-C) to be added is at most 110% by weight, preferably 1 to 100% by weight based on the component (3-B).

Examples of the linear or branched, saturated or unsaturated $C_8$–$C_{44}$ alcohol to be used as the component (3-C) include the following:

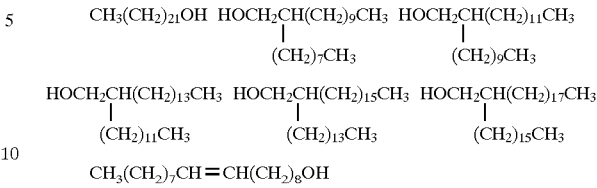

Further, the softener composition (3) according to the present invention may further contain a linear or branched, saturated or unsaturated $C_8$–$C_{36}$ fatty acid as component (3-D) to improve the softening effect and storage stability of the composition. The amount of the component (3-D) added is at most 100% by weight, preferably 0.5 to 50% by weight based on the component (3-B).

Examples of the fatty acid to be used as the component (3-D) include stearic acid, palmitic acid, myristic acid, Laurie acid, caprinic acid, caprylic acid, oleic acid, isostearic acid, and fatty acids resulting from natural fats and oils such as coconut oil, palm oil, tallow, rape seed oil and fish oil.

The composition (3) according to the present invention may contain a $C_1$–$C_4$ monohydric alcohol as component (3-E) for the purpose of controlling the viscosity of the composition and improving the storage stability thereof (i.e., inhibiting the composition from gelation). The amount of the component (3-E) to be added is at most 60% by weight, preferably 5 to 50% by weight, still preferably 10 to 45% by weight based on the component (3-B).

Examples of the $C_1$–$C_4$ monohydric alcohol to be used as the component (3-E) include methyl alcohol, ethyl alcohol, propyl alcohol, isopropyl alcohol and butyl alcohol.

The composition (3) according to the present invention may contain one or more members selected from among conventional cation compounds (such as quaternary ammonium salts and imidazolinium salts), esters and amides as softener base material. Examples of the compound to be used in this case include quaternary ammonium salts represented by the following general formula (3-XXVI):

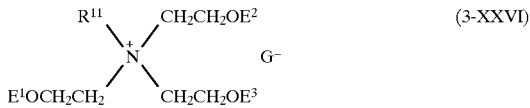

[wherein
$R^{11}$: $C_1$–$C_4$ alkyl or hydroxyalkyl group,
$E^1$, $E^2$, $E^3$: H atom or a group represented by $R^{12}CO$— (wherein $R^{12}$ represents linear or branched $C_7$–$C_{35}$ alkyl or alkenyl group), with the proviso that at least one of $E^1$, $E^2$ and $E^3$ is a group represented by $R^{12}CO$— (wherein $R^{12}$ is as defined above), though $E^1$, $E^2$ and $E^3$ may be the same or different from each other, and
G—: an anion group]

The anion as defined with respect to $G^-$ includes halide ions such as $Cl^-$ and $Br^-$ and $C_1$–$C_5$ alkylsulfate anions.

Among the softener compositions (3) according to the present invention, one containing the component (3-B) in a higher concentration tends to thicken during storage. In order to inhibit this thickening, it is preferable to add, as component (3-F), a polyether compound prepared by addition reaction of a compound having at least three active hydrogen atoms with ethylene oxide and, if necessary, propylene oxide and/or trimethylene oxide which has a weight-average molecular weight of 5000 to 2,000,000 and in which the total amount of oxyethylene chain moieties accounts for at least 55% by weight of the molecular weight, or a derivative of the polyether compound.

Examples of the compound having at least three active hydrogen atoms to be used in the preparation of the component (3-F) as starting material include polyhydric alcohols such as trimethylolpropane, diethanolamine, triethanolamine, glycerol, pentaerythritol, sorbitol, sucrose, polyglycerol, polyvinyl alcohol and partially saponified polyvinyl acetate; polyhydric phenols such as phenolic resin and alkylphenol-formalin condensate: polyamines such as ethylenediamine and polyethyleneimines (such as diethylenetriamine, triethylenetetramine, tetraethylenepentamine and pentaethylenehexamine). Further, partial amidation products of these polyamines and N-alkylation products thereof which are derivatives of the polyamines can be used in the preparation of the component (3-F), as far as they each have at least three active hydrogen atoms.

The component (3-F) can be prepared by conventional addition reaction of a compound having at least three active hydrogen atoms with ethylene oxide and, if necessary, propylene oxide and/or trimethylene oxide. The component (3-F) is preferably an adduct of such a compound with ethylene oxide alone, a block adduct thereof with ethylene oxide and propylene oxide or a partial block adduct thereof with ethylene oxide and propylene oxide. In preparing an adduct of a compound having at least three active hydrogen atoms with two or more alkylene oxides, it is preferable from the standpoint of inhibiting a composition (1) having a higher content of the component (3-B) from thickening in storage that the addition of the compound with propylene oxide (hereinafter abbreviated to "PO") be first conducted, followed by the addition with ethylene oxide (hereinafter abbreviated to "EO"), though the addition with either of PO and EO may be conducted antecedently.

The molecular weight of the component (3-F) ranges from 5,000 to 2,000,000, preferably 10,000 to 100,000. Further, the total amount of the oxyethylene (EO) chain moieties accounts for at least 55% by weight, preferably at least 80% by weight of the molecular weight.

When the molecular weight of the component (3-F) is less than 5,000, the resulting softener composition will little be inhibited from thickening during storage, while when it exceeds 2,000,000, the resulting softener composition will have too high a viscosity to be easily taken out of a bottle unfavorably.

When the ratio of the total weight of the oxyethylene chain moieties to the molecular weight of component (3-F) is less than 55% by weight, the resulting softener composition will little be inhibited from thickening in storage.

The polyether derivative to be used as the component (3-F) includes products of crosslinking of the above polyether compounds with compounds having isocyanate group; wherein terminal hydroxyl group is sulfated, phosphated, carboxyalkylated and fatty acid-esterified derivatives of the above polyether compounds; and products of partial N-cationization of the polyether compounds, among which fatty acid-esterified derivatives of the polyether compounds and products of partial N-cationization thereof are preferable.

The fatty acid to be used in the preparation of the fatty acid-esterified derivatives is preferably one having 7 to 23 carbon atoms, while the number of double bonds of the fatty acid or the presence of branch in the fatty acid has little influence on the performance of the softener composition.

The products of partial N-cationization of the polyether compounds include compounds prepared by partially cationizing the nitrogen of the polyester compounds with dialkyl sulfates and alkyl halides, and cation compounds prepared by neutralizing the compounds obtained by the above partial cationization with acetic acid, alkylbenzenesulfonic acids and so forth.

The softener composition (3) according to the present invention may contain the component (3-F) in an amount of 0.5 to 5% by weight, preferably 1 to 3% by weight based on the composition. The weight ratio of the component (3-F) to the component (3-B) ranges from 1/100 to 1/2.5, preferably 1/50 to 1/5. The total amount of the components (3-B) and (3-F) is 4 to 45% by weight, preferably 11 to 39% by weight, still preferably 14 to 32% by weight based on the composition (3). When the amount of the component (3-F) lies within the above range, the softener composition (3) according to the present invention exhibits a desirable softening effect and is inhibited from thickening during storage.

The composition (3) according to the present invention may further contain an inorganic electrolyte such as NaCl, $CaCl_2$ or $MgCl_2$ to control the viscosity thereof. The amount of the inorganic electrolyte to be added in this case is 0 to 2% by weight, preferably 0.01 to 1% by weight based on the composition.

The softener composition (3) according to the present invention may further contain an acidic or alkaline substance to adjust its pH. It is desirable in respects of the viscosity and storage stability of the composition that such a substance is added in such a way that the pH of the composition falls in the range of 1.5 to 6.5.

Although the softener composition (3) of the present invention is excellent in long-term storage stability, it may further contain a nonionic surfactant such as polyoxyethylene(p=5 to 50) alkyl or alkenyl($C_{12}$–$C_{24}$) ether or polyoxyethylene (p=5 to 50) alkyl or alkenyl($C_{12}$–$C_{24}$) amine or a hydrotrope such as ethylene glycol, propylene glycol or urea in order to improve the storage stability thereof under severer conditions.

The composition (3) according to the present invention may further contain a pigment or dye for the purpose of improving its appearance, a silicone for the purpose of inhibiting the composition from foaming in rinsing, and/or a perfume for the purpose of improving the comfortableness of the composition in use and the comfortableness of the textile treated with the composition.

In addition to the above essential and optional components, the softener composition (3) according to the present invention contains the balance of water.

A process for preparing the softener composition (3) according to the present invention will now be described, though the process for the preparation thereof is not limited to this process.

A mixture of the components (3-A) and (3-B) or a mixture comprising the components (3-A) and (3-B) and the other components (except the component (3-F)) is molten and the obtained melt is gradually dropped into deionized water kept at 60° C under stirring to form an emulsion. Thereafter, the component (3-F) may be added to the emulsion at need. An aqueous solution of a nonionic surfactant may be used instead of the deionized water, and an inorganic salt may be added after the completion of the addition of the components (3-A) to (3-F) for the purpose of controlling the viscosity of the composition.

The softener composition (3) according to the present invention can impart sufficient softness and excellent elasticity to various textiles, exhibits excellent storage stability (i.e., little causes gelation or thickening during storage and little suffers from hydrolysis of the softener base materials even after storage), and is extremely excellent in water absorption properties.

The invention (4) provides a liquid softener composition comprising the following components (4-A) and (4-B) at a weight ratio of (4-A)/(4-B) of 2/1 to 1/9. The description given above for the invention (3) can apply also to the invention (4).

[Component (4-A)]

a compound represented by the following general formula (4-I):

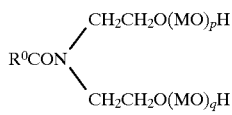
(4-I)

[wherein
$R^O$: linear or branched $C_7$–$C_{23}$ alkyl or alkenyl group,
M: $C_2$–$C_3$ alkylene group or a mixture of $C_2$ alkylene group with $C_3$ alkylene group, and
p, q: a number of 0 or above, with the proviso that the sum of p and q is 0 to 4 on an average], and

[Component (4-B)]

a quaternary ammonium salt represented by the following general formula (4-II):

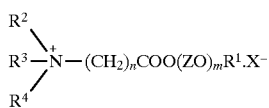
(4-II)

[wherein
$R^1$ : linear or branched $C_{20}$–$C_{44}$ alkyl or alkenyl group,
$R^2$, $R^3$, $R^4$: $C_{1-C5}$ alkyl or hydroxyalkyl group, wherein $R^2$, $R^3$ and $R^4$ may be the same or different from each other,
Z: $C_2$–$C_3$ alkylene group or a mixture of $C_2$ alkylene group with $C_3$ alkylene group,
m: a number of 0 to 20,
n: a number of 1 to 6, and
$X^-$: an anion group]

The invention will now be described in detail.

[Component (4-A)]

In the invention (4), a compound represented by the above general formula (4-I) is used as component (4-A).

In the general formula (4-I), the sum of p and q is 0 to 4 on an average. When the sum exceeds 4, no satisfactory softening effect will be attained. It is particularly preferable that both p and q be 0.

Further, the replacement of the component (4-A) by a fatty acid monoethanolamide or an adduct thereof with ethylene oxide which has a similar chemical structure to that of the component (4-A) fails in giving a composition excellent in storage stability.

In the general formula (4-I), $R^O$ is at least one member selected from the group consisting of alkyl group resulting from coconut oil fatty acid, alkyl resulting from palm kernel oil fatty acid, alkyl group resulting from palm oil fatty acid, alkyl group resulting from palm stearic acid, alkyl group resulting from hardened palm stearic acid, alkyl group resulting from tallow fatty acid, alkyl group resulting from hardened tallow fatty acid, and so forth.

Examples of the component (4-A) are as follows:

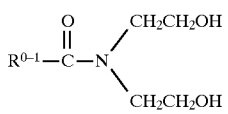

[wherein $R^{0-1}$: alkyl group resulting from tallow fatty acid]

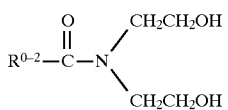

[wherein $R^{0-2}$: alkyl group resulting from hardened tallow fatty acid]

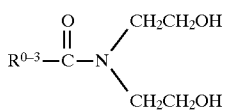

[wherein $R^{0-3}$: alkyl group resulting from palm stearic acid]

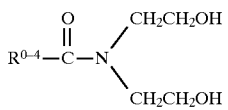

[wherein $R^{0-4}$: alkyl group resulting from hardened palm stearic acid]

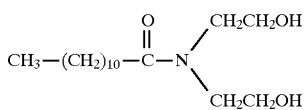

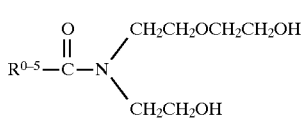

[wherein $R^{0-5}$: alkyl group resulting from coconut oil fatty acid]

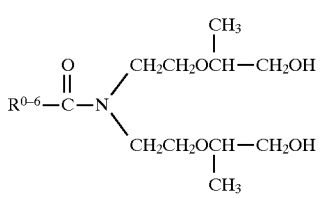

[wherein $R^{0-6}$: alkyl group resulting from palm kernel oil fatty acid]

The softener composition (4) according to the present invention may further contain a softener base material represented by the following general formula (4-XIII-1) to (4-XIII-3) in an amount of 0 to 15% by weight based on the composition:

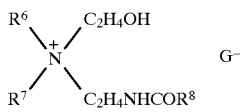
(4-XIII-1)

[wherein
$R^6$, $R^7$: $C_1$–$C_4$ alkyl group, $R^8$: linear or branched $C_7$–$C_{23}$ alkyl or alkenyl group, and $G^-$: a halide ion or $R^9SO_4^-$ group (wherein $R^9$ represents $C_1$–$C_4$ alkyl group), wherein $G^-$ and $X^-$ may be the same or different from each other],

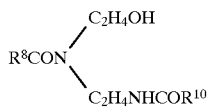
(4-XIII-2)

[wherein
$R^8$: as defined above, and
$R^{10}$: linear or branched $C_7$–$C_{23}$ alkyl or alkenyl group],
and

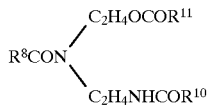
(4-XIII-3)

[wherein
$R^8$, $R^{10}$: each as defined above, and
$R^{11}$: linear or branched $C_7$–$C_{23}$ alkyl or alkenyl group]

The composition (4) according to the present invention may further contain a conventional softener base material, as far as the object of the present invention is not marred.

A process for preparing the softener composition (4) will now be described, though the process for the preparation thereof is not limited to this process. A mixture of the components (4-A) and (4-B) or a mixture comprising the components (4-A) and (4-B) and the other components (except the component (4-F)) is molten and the obtained melt is gradually dropped into deionized water kept at 60° C. under stirring, to form an emulsion. Thereafter, the component (4-F) may be added to the emulsion at need. A nonionic surfactant may be preliminarily added to the deionized water, and an inorganic salt may be added after the completion of the addition of the components (4-A) and (4-B) and the other components in order to control the viscosity of the composition.

The invention (5) provides a process of preparing a quaternary ammonium salt represented by the above general formula (5-I) by reaction of a corresponding tertiary amine with a quaternizing agent, characterized by conducting the reaction in the presence of a polyhydric alcohol ester represented by the general formula (5-II):

$$G[-OH]_p[-(OA)_mOH]_q[-OCR]_r[-(OA)_nOCR]_s \quad (5\text{-}II)$$

[wherein
G group: a residue obtained by freeing a starting polyhydric alcohol completely from alcoholic hydroxyl groups, [—OH] group, [—(OA)$_m$OH] group,

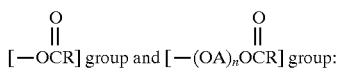

each bonded to G at the carbon atom to which an alcoholic hydroxyl group used to be bonded, wherein A group represents $C_2$–$C_4$ alkylene group, R group represents linear or branched $C_7$–$C_{23}$ alkyl or alkenyl group, and m and n are each a number of 0 to 100 corresponding to the average number of alkylene oxide molecules added, a number of m plus n of A's being the same or different from each other, and p, q, r and s: each a number of 0 or above, with the provisos that the sum of p, q, r and s corresponds to the number of alcoholic hydroxyl groups of the starting polyhydric alcohol and that neither the Sum of p and q nor that of r and s is 0.]

It is preferable that the polyhydric alcohol ester represented by the above general formula (5-II) used in invention (5) be at least one member selected from the group consisting of the following compounds (5-a), (5-b) and (5-c):

(5-a) fatty acid esters of pentaerythritol (characterized by having at least one hydroxyl group) and adducts thereof with alkylene oxide (wherein the alkylene oxide has 2 or 3 carbon atoms), (5-b) fatty acid esters of glycerol (characterized by having at least one hydroxyl group) and adducts thereof with alkylene oxide (wherein the alkylene oxide has 2 or 3 carbon atoms), and (5-c) fatty acid esters of sorbitan (characterized by having at least one hydroxyl group) and adducts thereof with alkylene oxide (wherein the alkylene oxide has 2 or 3 carbon atoms).

Among these polyhydric alcohol esters, it is preferable to use a fatty acid ester of glycerol (having at least one hydroxyl group) or an adduct thereof with alkylene oxide (wherein the alkylene group has 2 or 3 carbon atoms), still preferably one prepared by reacting a natural fat or oil with glycerol and an alkylene oxide at a molar ratio of the fat or oil to glycerol to the alkylene oxide of 1 (0.1 to 5) to (2 to 100).

The polyhydric alcohol ester represented by the above general formula (5-II) can be prepared by, e.g., the following known synthesis processes (5-i) to (5-vi)

Synthesis process (5-i)

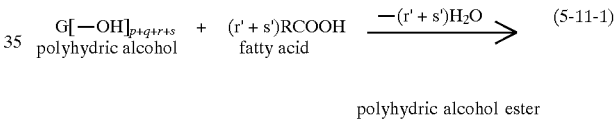

polyhydric alcohol ester

[wherein
G, R, p, q, r and s: each as defined above, and r', s': numbers satisfying the relationship:

$$0 < (r' + s') < (p + q + r + s)]$$

According to the synthesis process (5-i), a polyhydric alcohol is esterified with a fatty acid. In this esterification, the molar ratio of the polyhydric alcohol to the fatty acid is selected within such a range that the formed polyhydric alcohol ester (5-II-1) has at least one hydroxyl group remaining free.

The esterification may be conducted without any catalyst or in the presence of an acid catalyst such as sulfuric acid, hydrochloric acid or p-toluenesulfonic acid.

Examples of the polyhydric alcohol to be used in this process include glycerol, erythritol, pentaerythritol, sorbitol and sorbitan, which may be used alone or as a mixture of two or more of them. The use of glycerol is preferable.

Examples of the fatty acid to be used in this process include caprinic acid, lauric acid, myristic acid, palmitic acid, oleic acid, stearic acid, isostearic acid, arachidic acid, behenic acid, and fatty acids resulting from unhardened and hardened animal fats (such as tallow and lard), palm oil, palm kernel oil, coconut oil, rape seed oil and fish oil, which may be used alone or as a mixture of two or more of them. It is preferable to use a fatty acid resulting from tallow, palm oil, palm kernel oil or coconut oil.

Synthesis process (5-ii)

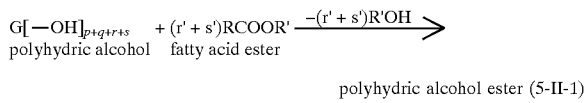

polyhydric alcohol ester (5-II-1)

[wherein

G, R, p, q, r, s, r' and s': each as defined above, and

R': a residue obtained by freeing a monohydric or polyhydric alcohol from hydroxyl group(s)]

According to the synthesis process (5-ii), a fatty acid ester is transesterified with a polyhydric alcohol. In this synthesis process (5-ii), NaOH, KOH, NaOCH$_3$ or KOCH$_3$ is used as catalyst.

Examples of the fatty acid ester to be used in the synthesis process (5-ii) include esters of the fatty acids described in the section "Synthesis process (5-i)" with methanol, ethanol, propanol, butanol, ethylene glycol, glycerol, erythritol, pentaerythritol, xylitol, sorbitol and sorbitan; and natural fats and oils. The use of a natural fat or oil is preferable for industrial production and specific examples thereof include tallow, palm oil, palm kernel oil and coconut oil.

Synthesis process (5-iii)

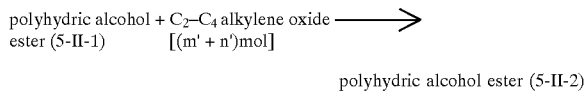

polyhydric alcohol ester (5-II-2)

[wherein polyhydric alcohol ester (5-II-1):
a polyhydric alcohol ester prepared by the synthesis process (5-i) or (5-ii), and m', n': each a number of 0 to 100, with the proviso that the case wherein both m' and n' are 0 is excepted].

According to the synthesis process (5-iii), the polyhydric alcohol ester (5-II-2) can be prepared by conducting the addition reaction of the polyhydric alcohol ester (5-II-1) prepared by the process (5-i) or (5-ii) with C$_2$–C$_4$ alkylene oxide. The catalyst to be used in the addition reaction includes NaOH, KOH, NaOCH$_3$, KOCH$_3$ and alkali metal salts of fatty acids.

In the addition reaction, the molar ratio of the alkylene oxide to the polyhydric alcohol ester (II-1) is preferably 1/1 to 100/1, still preferably 1/1 to 50/1.

Synthesis process (5-iv)

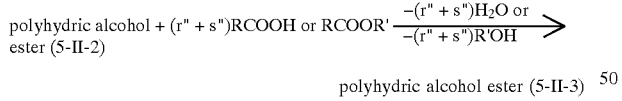

polyhydric alcohol ester (5-II-3)

[wherein

R, R': each as defined above, polyhydric alcohol ester (5-II-2): a polyhydric alcohol ester prepared by the synthesis process (5-iii), and r'', s'': numbers satisfying the relationship:

$$0<(r'+s'+r''+s'')<(p+q+r+s)$$

wherein r', s', p, q, r and s are each as defined above]

According to the synthesis process (5-iv), a polyhydric alcohol ester (5-II-2) prepared by the synthesis process (5-iii) is reacted with a fatty acid or ester thereof used in the synthesis process (5-i) or (5-ii) under the same conditions as described for the synthesis process (5-i) or (5-ii).

Although the polyhydric alcohol ester (5-II-3) prepared by this process is contaminated with unreacted polyhydric alcohol ester or fatty acid, such contamination is not problematic, so far as it does not mar the effects of the present invention.

Synthesis process (5-v)

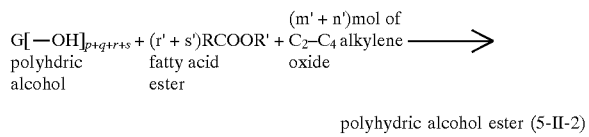

polyhydric alcohol ester (5-II-2)

[wherein G, R, R', p, q, r, s, r', s', m' and n' are each as defined above]

In the process (5-v), the molar ratio of the polyhydric alcohol to the fatty acid ester is selected within such a range that the formed polyhydric alcohol ester (5-II-2) has a hydroxyl group remaining free. Further, it is preferable that the molar ratio of the alkylene oxide to the polyhydric alcohol range from 1/1 to 100/1, still preferably 5/1 to 50/1.

The catalyst to be used in this synthesis process (5-v) may be the same as described for the synthesis process (5-iii).

Synthesis process (5-vi)

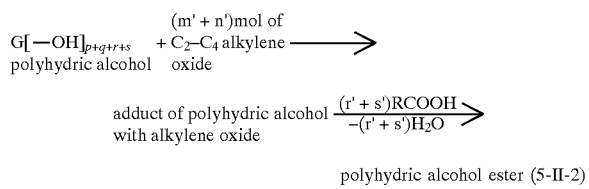

polyhydric alcohol ester (5-II-2)

[wherein G, R, p, q, r, s, r', s', m' and n' are each as defined above]

According to the process (5-vi), the addition reaction of a polyhydric alcohol with an alkylene oxide is conducted under the same conditions as described in the section "Synthesis process (5-iii)" and thereafter the obtained adduct is esterified with a fatty acid under the same conditions as described in the section "Synthesis process (5-i)".

Among the above synthesis processes (5-i) to (5-vi), the process (5-iii) is preferable.

Examples of the polyhydric alcohol ester (5-II) prepared by the above synthesis processes (5-i) to (5-vi) include the following, which may be used alone or as a mixture of two or more of them:

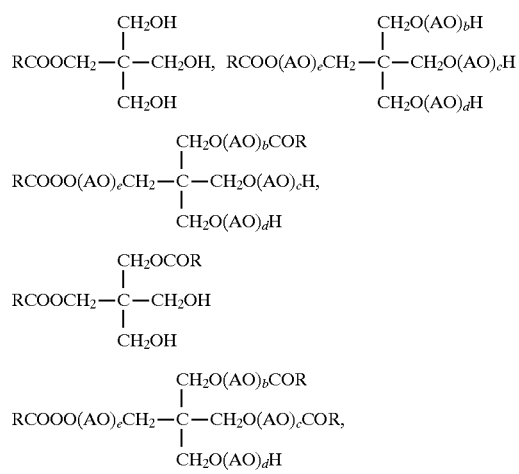

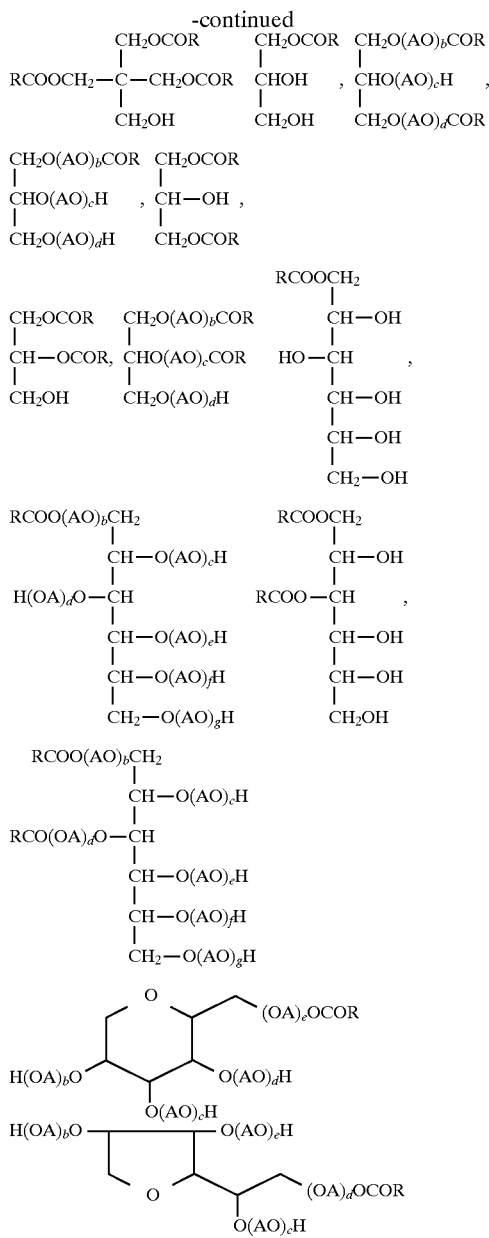

[wherein
R, A: each as defined above, and
b, c, d, e, f, g: each an average number of $C_2$–$C_4$ alkylene oxide molecules added]

Among the polyhydric alcohol esters represented by the above general formula (5-II), it is particularly preferable to use a product obtained by reacting a natural fat or oil with glycerol and an alkylene oxide at a molar ratio of the fat or oil to glycerol to the alkylene oxide of 1: (0.1 to 5) : (2 to 100). Specifically, this product can be prepared, e.g., as follows.

Namely, the product can be prepared by mixing a natural fat or oil with glycerol, adding a basic catalyst to the mixture, and gradually adding an alkylene oxide to the resulting mixture to conduct a reaction.

The natural fat or oil to be used in the case includes tallow, palm oil, palm kernel oil, products of partial and complete hardening of them, and mixtures of two or more of them. The alkylene oxide to be used therein includes ethylene oxide, propylene oxide and butylene oxide, among which ethylene oxide, propylene oxide and mixtures of both are preferable. When an alkylene oxide mixture is used, the constituent alkylene oxides may be simultaneously or successively reacted with the other reactants. The basic catalyst usable therein includes potassium hydroxide, sodium hydroxide and sodium methylate. The reaction temperature is 100° to 200° C., preferably 140° to 170° C.

In the above preparation, it is preferable that a natural fat or oil, glycerol and the alkylene oxide be used at a molar ratio of 1 : (0.1 to 5) : (2 to 100), still preferably 1 : (1 to 5) : (10 to 100).

Further, the above product may be replaced by one prepared by the following process:

namely, glycerol may be mixed with a fatty acid corresponding to a natural fat or oil to conduct esterification, followed by the addition of the obtained ester with alkylene oxide. Alternatively, the addition of glycerol with alkylene oxide may be first conducted, followed by the esterification of the obtained adduct with a fatty acid corresponding to a natural fat or oil.

The quaternary ammonium salt represented by the above general formula (5-I) which is the objective product of the process of the invention (5) may be any one, as far as it can be prepared from a corresponding tertiary amine and a quaternizing agent.

In the general formula (5-I), $R^1$ represents linear or branched $C_{20}$–$C_{44}$ alkyl or alkenyl group, preferably a group represented by the formula:

(wherein $R^5$ represents linear $C_8$–$C_{20}$ alkyl group) which is derived from an alcohol called "Guerbet alcohol".

It has been well known that when a primary alcohol is condensed through dehydration either in the presence of an alkaline substance or in the presence of an alkaline substance and a dehydrogenation catalyst, one branched dimeric alcohol molecule and one water molecule are formed from two primary alcohol molecules. Such a reaction is called "Guerbet reaction" and is represented by the following reaction formula:

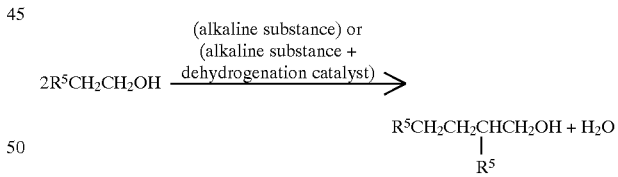

(wherein $R^5$ is as defined above)

The branched dimeric alcohol prepared by the Guerbet reaction is called "Guerbet alcohol".

The group derived from Guerbet alcohol is preferably one represented by the above formula wherein $R^5$ is linear $C_{12}$–$C_{16}$ alkyl group, still preferably linear $C_{16}$ alkyl group.

In the above general formula (5-I), $R^2$, $R^3$ and $R^4$ represent the same or different from each other $C_1$–$C_5$ alkyl group or hydroxyalkyl, preferably methyl group, ethyl or hydroxyethyl, still preferably methyl group; a is a number of 1 to 6, preferably 1; and $X^-$ represents an anion, desirably a halide ion or a $C_{1-C4}$ alkylsulfate ion, more desirably $Cl^-$, $Br^-$ or $CH_3SO_4^-$, most desirably $Cl^-$.

According to the process of the invention (5), the quaternary ammonium salt represented by the above general formula (5-I) can be prepared as follows: namely, a polyhydric alcohol ester represented by the general formula (5-II) is added into a reactor in an amount of 1 to 50% by weight, preferably 5 to 30% by weight based on the total amount of the whole reactants to be charged, and in the resulting reactor the reaction of a corresponding tertiary amine with a quaternizing agent is conducted. If necessary, an alcoholic solvent such as isopropyl alcohol or ethanol may be added in an amount of at most 20% by weight based on the whole reactants, though the addition thereof in an amount exceeding to this upper limit is undesirable from the standpoint of the object of the invention (5). The reaction temperature is 30° to 140° C., preferably 50° to 100° C.

The corresponding tertiary amine to the quaternary ammonium salt represented by the above general formula (5-I) which is the objective product; of the process of the invention (5) includes those represented by the general formula (5-III):

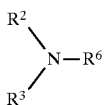　(5-III)

(wherein $R^2$ and $R^3$ are each as defined above; and $R^6$ represents $C_1$–$C_5$ alkyl or hydroxyalkyl group or a group represented by the formula: —$(CH_2)_a COOR^1$ (wherein $R^1$ and a are each as defined above). On the other hand, the quaternizing agent includes compounds represented by the general formula (5-IV):

$$X—R^7 \qquad (5\text{-}IV)$$

(wherein $R^7$ represents $C_1$–$C_5$ alkyl or hydroxyalkyl group or a group represented by the formula: —$(CH_2)_a COOR^1$ (wherein $R^1$ and a are each as defined above); and X represents halogen or $C_1$–$C_4$ alkyl sulfate). Specific examples of the quaternizing agent include chloromethane, dimethyl sulfate and compounds represented by the formula:

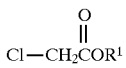

(wherein $R^1$ is as defined above).

The quaternary ammonium salt represented by the above general formula (5-I) which is prepared from the above tertiary amine and quaternizing agent includes the following compounds:

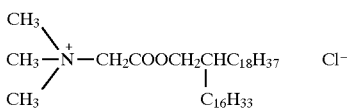

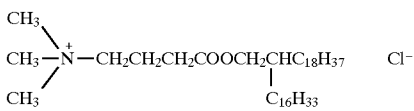

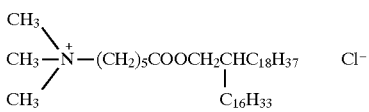

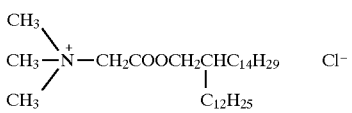

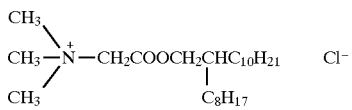

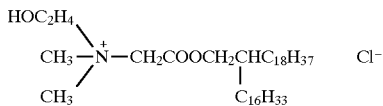

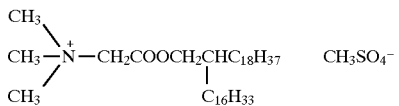

The quaternary ammonium salt represented by the general formula (5-I) which is prepared by the process of the invention (5) exhibits excellent softening effect and smell even when used in an unpurified state (i.e., in the form of the reaction mixture as such) as softener base material, being extremely useful as softener base material.

Although the reaction mixture obtained by the process of the invention (5) as such can be used as softener base material, a softener composition may be prepared by adding a higher alcohol or higher fatty acid for improving the softening effect and storage stability, a lower alcohol for controlling the viscosity and improving the storage stability, conventional cationic or nonionic surfactant, inorganic salt, pH regulator, hydrotrope agent, perfume, antifoaming agent and/or pigment to the reaction mixture to form an emulsion.

The invention (6) provides a process of preparing a quaternary ammonium salt represented by the above general formula (6-I) by reaction of a corresponding tertiary amine with a quaternizing agent, characterized by conducting the reaction in the presence of a compound represented by the general formula (6-II):

　(6-II)

(wherein $R^5$ represent linear or branched $C_7$–$C_{35}$ alkyl or alkenyl group; $A^1$ and $A^2$ represent the same or different from each other $C_2$–$C_4$ alkylene; and n and m may be the same or different from each other and each represent the average number of alkylene oxide molecules added, with sum of n and m being 0 to 4, wherein a number "n" of $A^1$'s and a number "m" of $A^2$'s may be the same or different from each other.)

The compound to be used in the invention (6) is particularly preferably a compound represented by the general formula (6-II) wherein $R^5$CO— group is a fatty acid residue resulting from a natural fat or oil and n and m is 0.

The compound to be used in the invention (6) represented by the general formula (6-II) can be prepared, e.g., as follows.

Namely, the compound can be prepared by reacting a natural fat or oil with diethanolamine in the presence of a basic catalyst to form an amide and, if necessary, gradually adding an alkylene oxide to the resulting mixture to conduct an addition reaction. A lower alcohol ester of fatty acid may be used instead of the natural fat or oil. Although the reaction product obtained by the use of a natural fat or oil contains glycerol or adducts thereof with alkylene oxide formed as a by-product in addition to the compound represented by the general formula (6-II), it can be used as such without purification in the invention (6).

The natural fat or oil usable in the above preparation includes tallow, palm oil, palm stearin oil, palm kernel oil, coconut oil, products of partial and complete hardening of them and mixtures of two or more of them, among which tallow, palm stearin oil, palm kernel oil and products of partial and complete hardening of them are preferable. On the other hand, the lower alcohol ester of fatty acid usable therein includes methyl and ethyl esters of $C_8$–$C_{36}$ fatty acids such as octanoic acid, lauric acid, myristic acid, palmitic acid, stearic acid and oleic acid, among which methyl and ethyl esters of $C_{12}$–$C_{18}$ fatty acids are preferable.

The alkylene oxide usable in the above preparation includes ethylene oxide, propylene oxide, butylene oxide and mixtures of two or more of them, among which ethylene oxide is preferable. When a mixture of two or more alkylene oxides is used, these alkylene oxides may be made to react simultaneously or successively. The basic catalyst usable therein includes potassium hydroxide, sodium hydroxide and sodium methylate.

The amidation of a natural fat or oil or a lower alcohol ester of fatty acid with diethanolamine is conducted at 60° to 200° C., preferably 80° to 150° C., while the addition reaction with an alkylene oxide is conducted at 100° to 200° C., preferably 140° to 170° C.

In the above preparation, it is preferable that diethanolamine be used in an amount of 0.8 to 1.2 mol, preferably 0.9 to 1.1 mol per mol of the ester group of the natural fat or oil or lower alcohol ester of fatty acid used. The number of alkylene oxide molecules added is 0 to 4 mole, preferably 0 to 3 mole per molecule of the diethanolamide.

The quaternary ammonium salt represented by the above general formula (6-I) which is the objective product of the process of the invention (6) may be any one, as far as it can be prepared from a corresponding tertiary amine and a quaternizing agent.

In the general formula (6-I), $R^1$ represents linear or branched $C_{20}$–$C_{44}$ alkyl or alkenyl group, preferably a group represented by the formula:

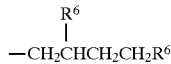

(wherein $R^6$ represents linear $C_8$–$C_{20}$ alkyl group) which is derived from an alcohol called "Guerbet alcohol".

It has been well known that when a primary alcohol is condensed through dehydration either in the presence of an alkaline substance or in the presence of an alkaline substance and a dehydrogenation catalyst, one branched dimeric alcohol molecule and one water molecule are formed from two primary alcohol molecules. Such a reaction is called "Guerbet reaction" and is represented by the following reaction formula:

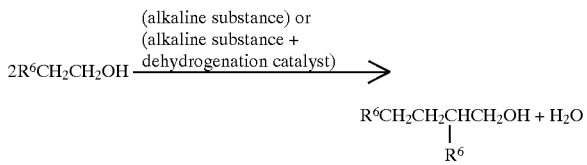

(wherein $R^6$ is as defined above)

The branched dimeric alcohol prepared by the Guerbet reaction is called "Guerbet alcohol".

The group derived from Guerbet alcohol is preferably one represented by the above formula wherein $R^6$ is linear ($C_{12}$–$C_6$ alkyl group, still preferably linear $C_6$ alkyl group.

In the above general formula (6-I), $R^2$, $R^3$ and $R^4$ represent the same or different from each other $C_1$–$C_5$ alkyl or hydroxyalkyl group, preferably methyl, ethyl or hydroxyethyl group, still preferably methyl group; a is a number of 1 to 6, preferably 1; and $X^-$ represents an anion, desirably a halide ion or a $C_1$–$C_4$ alkylsulfate ion, more desirably $Cl^-$, $B^-$ or $CH_3SO_4^-$, most desirably $Cl^-$.

According to the process of the invention, the quaternary ammonium salt represented by the above general formula (6-I) can be prepared as follows: namely, a compound represented by the general formula (6-II) is added into a reactor in an amount of 1 to 50% by weight, preferably 5 to 30% by weight based on the total amount of the whole reactants to be charged, and in the resulting reactor, the reaction of a corresponding tertiary amine with a quaternizing agent is conducted. If necessary, an alcoholic solvent such as isopropyl alcohol or ethanol may be added in an amount of at most 20% by weight based on the whole reactants, though the addition thereof in an amount exceeding this upper limit is undesirable from the standpoint of the object of the invention. The reaction temperature is 30° to 1400° C., preferably 50 to 100° C.

The tertiary amine corresponding to the quaternary ammonium represented by the above general formula (6-I) which is the objective product of the process of the invention (6) includes those represented by the general formula (6-III):

(wherein $R^2$ and $R^3$ are each as defined above; and $R^7$ represents $C_1$–$C_5$ alkyl or hydroxyalkyl group or a group represented by the formula:

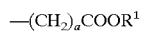

(wherein $R^1$ and a are each as defined above)).

On the other hand, the quaternizing agent includes compounds represented by the general formula (6-IV):

$$X\text{—}R^8 \qquad (6\text{-}IV)$$

(wherein $R^8$ represents $C_1$–$C_5$ alkyl or hydroxyalkyl group or a group represented by the formula: —$(CH_2)_a COOR^1$ (wherein $R^1$ and a are each as defined above); and X represents halogen or $C_1$–$C_4$ alkylsulfate).

Specific examples of the quaternizing agent include chloromethane, dimethyl sulfate and compounds represented by the formula:

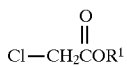

(wherein $R^1$ is as defined above).

The quaternary ammonium salt represented by the above general formula (6-I) which is prepared from the above tertiary amine and quaternizing agent includes the following compounds:

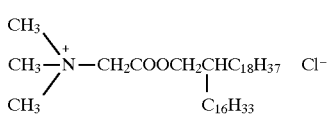

-continued

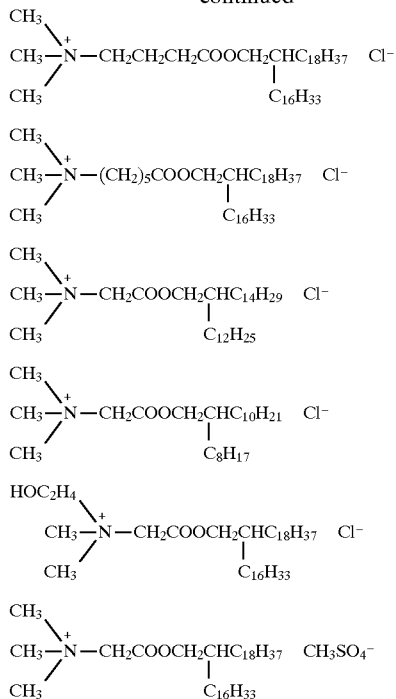

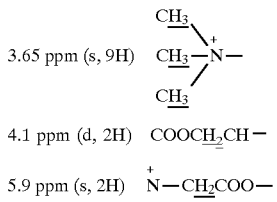

NMR spectrum (CDCl$_3$, internal standard: TMS)

3.65 ppm (s, 9H)  CH$_3$—N$^+$— (CH$_3$, CH$_3$)

4.1 ppm (d, 2H)   COOC$\underline{H}_2$CH—

5.9 ppm (s, 2H)   $\overset{+}{N}$—C$\underline{H}_2$COO—

IR spectrum (KBr tablet) 1746 cm$^{-1}$, 1206 cm$^{-1}$

Example 1-2

Chlorobutyric acid (44 g) and 2-hexadecyleicosyl alcohol (156 g) were put in a four-necked flask fitted with a stirrer, a thermometer and a condenser. The contents were heated to 140° C. While formed water was distilled away, the contents were reacted at that temperature for 7 hours. The obtained reaction mixture was washed with water to remove excess chlorobutyric acid. Thus, 185 g of a chlorobutylate ester was obtained. A 50% aqueous solution (64 g) of dimethylamine and water (100 g) were added to the chlorobutyrate ester. The obtained mixture was heated to 55° C. and reacted at that temperature for 10 hours. After the completion of the reaction, the obtained reaction mixture was freed from excess dimethylamine by washing with water, giving 185 g of a 4-amino-butyrate ester.

[EXAMPLE]

Examples of novel quaternary ammonium salts (1-I-1) of the present invention, Synthesis Examples of quaternary ammonium salts (1-I) according to the present invention and Examples of liquid softener compositions of the present invention will now be described to illustrate the present invention in more detail, though the present invention is not limited by them.

The above 4-aminobutyrate ester (95 g), methyl chloride (15 g) and isopropyl alcohol (70 g) were charged into an autoclave fitted with a stirrer and a thermometer. The resulting mixture was reacted at 90° C. for 6 hours. After the completion of the reaction, the reaction mixture was subjected to crystallization with acetone and the obtained solid was dried to give 90 g of an objective product as a white powder.

Example 1-1

Chloroacetic acid (34 g) and 2-hexadecyleicosyl alcohol (156 g) were put in a four-necked flask fitted with a stirrer, a thermometer and a condenser. The contents were heated to 140° C. While formed water was distilled away, the contents were reacted at that temperature for 7 hours. The obtained reaction mixture was washed with water to remove excess chloroacetic acid. Thus, 175 g of a chloroacetate ester was obtained. A 50% aqueous solution (64 g) of dimethylamine and water (100 g) were added to the chloroacetate ester. The obtained mixture was heated to 55° C. and reacted at that temperature for 10 hours. After the completion of the reaction, the obtained reaction mixture was freed from excess dimethylamine by washing with water, giving 170 g of a glycinate ester.

It was confirmed by NMR and IR spectroscopic analyses that this product had the following structure:

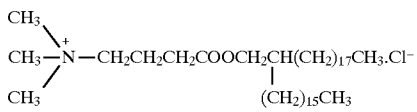

NMR spectrum (CDCl$_3$, internal standard: TMS)

2.1 ppm (m, 2H)   $\overset{+}{N}$—CH$_2$C$\underline{H}_2$CH$_2$—

2.5 ppm (t, 2H)   —CH$_2$C$\underline{H}_2$COO—

3.48 ppm (s, 9H)  CH$_3$—N$^+$— (CH$_3$, CH$_3$)

3.7 ppm (m, 2H)   $\overset{+}{N}$—C$\underline{H}_2$CH$_2$—

3.95 ppm (d, 2H)  —COOC$\underline{H}_2$—

The above glycinate ester (90 g), methyl chloride (15 g) and acetone (70 g) were charged into an autoclave fitted with a stirrer and a thermometer. The resulting mixture was reacted at 90° C. for 6 hours. After the completion of the reaction, the reaction mixture was subjected to crystallization with acetone and the obtained solid was dried to give 85 g of an objective product as a white powder.

It was confirmed by NMR and IR spectroscopic analyses that this product had the following structure:

IR spectrum (KBr tablet) 1731 cm$^{-1}$, 1182 cm$^{-1}$

Example 1-3

Chlorohexanoic acid (45 g) and 2-hexadecyleicosyl alcohol (156 g) were put in a four-necked flask fitted with a stirrer, a thermometer and a condenser. The contents were heated to 140° C. While formed water was distilled away, the contents were reacted at that temperature for 10 hours. Thus, 195 g of a chlorohexanoate ester was obtained. A 50% aqueous solution (64 g) of dimethylamine and water (100 g) were added to the chlorohexanoate ester. The obtained mixture was heated to 60° C. and reacted at that temperature for 10 hours. After the completion of the reaction, the obtained reaction mixture was freed from excess dimethylamine by washing with water, giving 195 g of a 6-aminohexanoate ester.

The above 6-aminohexanoate ester (100 g), methyl chloride (15 g) and isopropyl alcohol (80 g) were charged into an autoclave fitted with a stirrer and a thermometer. The resulting mixture was reacted at 90° C. for 8 hours. After the completion of the reaction, the reaction mixture was subjected to crystallization with acetone and the obtained solid was dried to give 1030 g of an objective product as a white powder.

It was confirmed by NMR and IR spectroscopic analyses that this product had the following structure:

$$\begin{array}{c}CH_3\\ \quad \diagdown{}^+\\ CH_3-N-(CH_2)_5COOCH_2CH(CH_2)_{17}CH_3.Cl^-\\ \quad \diagup \quad\quad\quad\quad\quad\quad |\\ CH_3 \quad\quad\quad\quad\quad (CH_2)_{15}CH_3\end{array}$$

NMR spectrum (CDCl$_3$, internal standard: TMS)

| | |
|---|---|
| 2.45 ppm (t, 2H) | —CH$_2$C$\underline{H_2}$COO— |
| 3.43 ppm (s, 9H) | 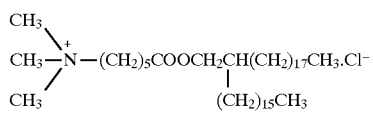 |
| 3.67 ppm (m, 2H) | $\overset{+}{N}$—C$\underline{H_2}$CH$_2$— |
| 3.9 ppm (d, 2H) | —COOC$\underline{H_2}$— |

IR spectrum (KBr tablet) 1730 cm$^{-1}$, 1185 cm$^{-1}$

Synthesis Example 1-1

Chloroacetic acid (34 g) and 2-dodecylhexadecyl alcohol (123 g) were put in a four-necked flask fitted with a stirrer, a thermometer and a condenser. The contents were heated to 140° C. While formed water was distilled away, the contents were reacted at that temperature for 5 hours. The obtained reaction mixture was washed with water to remove excess chloroacetic acid. Thus, 145 g of a chloroacetate ester was obtained. A 50% aqueous solution (64 g) or dimethyl amine and water (100 g) were added to the chloroacetate ester. The obtained mixture was heated to 550° C. and reacted at that temperature for 10 hours. After the completion of the reaction, the obtained reaction mixture was freed from excess dimethylamine by washing with water, giving 145 g of a glycinate ester.

The above glycinate ester (75 g), methyl chloride (15 g) and acetone (50 g) were charged into an autoclave fitted with a stirrer and a thermometer. The resulting mixture was reacted at 900° C. for 6 hours. After the completion of the reaction, the reaction mixture was subjected to crystallization with acetone and the obtained solid was dried to give 70 g of an objective product as a white powder.

It was confirmed by NMR and IR spectroscopic analyses that this product had the following structure:

$$\begin{array}{c}CH_3\\ \quad \diagdown{}^+\\ CH_3-N-CH_2COOCH_2CH(CH_2)_{13}CH_3.Cl^-\\ \quad \diagup \quad\quad\quad\quad\quad\quad |\\ CH_3 \quad\quad\quad\quad\quad (CH_2)_{11}CH_3\end{array}$$

NMR spectrum (CDCl$_3$, internal standard: TMS)

| | |
|---|---|
| 3.65 ppm (s, 9H) | 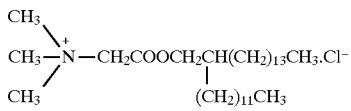 |
| 4.05 ppm (d, 2H) | COOC$\underline{H_2}$CH— |
| 4.9 ppm (s, 2H) | $\overset{+}{N}$—C$\underline{H_2}$COO— |

IR spectrum (KBr tablet) 1748 cm$^{-1}$, 1205 cm$^{-1}$

Synthesis Example 1-2

Chloroacetic acid (34 g) and 2-octyldodecyl alcohol (90 g) were put in a four-necked flask fitted with a stirrer, a thermometer and a condenser. The contents were heated to 140° C. While formed water was distilled away, the contents were reacted at that temperature for 5 hours. The obtained reaction mixture was washed with water to remove excess chloroacetic acid. Thus, 110 g of a chloroacetate ester was obtained. A 50% aqueous solution (64 g) of dimethylamine and water (100 g) were added to the chloroacetate ester. The obtained mixture was heated to 55° C. and reacted at that temperature for 10 hours. After the completion of the reaction, the obtained reaction mixture was freed from excess dimethylamine by washing with water, giving 113 g of a glycinate ester.

The above glycinate ester (57 g), methyl chloride (15 g) and acetone (400 g) were charged into an autoclave fitted with a stirrer and a thermometer. The resulting mixture was reacted at 90° C. for 6 hours.

After the completion of the reaction, the reaction mixture was subjected to crystallization with acetone and the obtained solid was dried to give 60 g of an objective product as a white powder.

It was confirmed by NMR and IR spectroscopic analyses that this product had the following structure:

$$\begin{array}{c}CH_3\\ \quad \diagdown{}^+\\ CH_3-N-CH_2COOCH_2CH(CH_2)_9CH_3.Cl^-\\ \quad \diagup \quad\quad\quad\quad\quad\quad |\\ CH_3 \quad\quad\quad\quad\quad (CH_2)_7CH_3\end{array}$$

NMR spectrum (CDCl$_3$, internal standard: TMS)

| | |
|---|---|
| 3.68 ppm (s, 9H) | 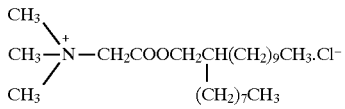 |

4.1 ppm (d, 2H)   COOC$\underline{H_2}$CH—

4.95 ppm (s, 2H)   $\overset{+}{N}$—C$\underline{H_2}$COO—

IR spectrum (KBr tablet) 1746 cm$^{-1}$, 1205 cm$^{-1}$

The quaternary ammonium salts prepared in Examples 1-1 to 1-3 and Synthesis Examples 1-1 and 1-2 are listed in Table 1-1.

TABLE 1-1

Structural formula of component (1-A) (quaternary ammonium salt (1-I))

Ex. 1-1

$$CH_3\diagdown\overset{+}{N}\diagup CH_3 —CH_2COOCH_2CH(CH_2)_{17}CH_3 \cdot Cl^-$$
$$|\ (CH_2)_{15}CH_3$$
(1-A-1)

Ex. 1-2

$$CH_3\diagdown\overset{+}{N}\diagup CH_3 —CH_2CH_2CH_2COOCH_2CH(CH_2)_{17}CH_3 \cdot Cl^-$$
$$|\ (CH_2)_{15}CH_3$$
(1-A-2)

Ex. 1-3

$$CH_3\diagdown\overset{+}{N}\diagup CH_3 —(CH_2)_5COOCH_2CH(CH_2)_{17}CH_3 \cdot Cl^-$$
$$|\ (CH_2)_{15}CH_3$$
(1-A-3)

Synth. Ex. 1-1

$$CH_3\diagdown\overset{+}{N}\diagup CH_3 —CH_2COOCH_2CH(CH_2)_{13}CH_3 \cdot Cl^-$$
$$|\ (CH_2)_{11}CH_3$$
(1-A-4)

Synth. Ex. 1-2

$$CH_3\diagdown\overset{+}{N}\diagup CH_3 —CH_2COOCH_2CH(CH_2)_9CH_3 \cdot Cl^-$$
$$|\ (CH_2)_7CH_3$$
(1-A-5)

Examples 1-4 to 1-23 and Comparative Examples 1-1 to 1-6

Softener compositions (adjusted to pH3) were prepared, which each comprised a quaternary ammonium salt (1-I) (component (1-A)) listed in Table 1-1, a higher alcohol (component (1-B)) listed in Table 1-2, a fatty acid (component (1-C))) listed in Table 1-3, a lower alcohol (component (1-D)), a polyalkylene oxide compound (component (1-E)) listed in Table 1-4 and so forth in amounts specified in Table 1-5 or 1-6. The storage stability of these softener compositions and the softness, elasticity and water absorption properties of textiles treated with these softener compositions were evaluated by the methods which will be described below. The results are given in Tables 1-7 and 1-8.

In Comparative Examples, the following compounds (1-S) to (1-U) were used, wherein $R^{23}$ and $R^{33}$ represent alkyl group obtained by replacing the carboxyl group of hardened tallow fatty acid by methylene group; and $R^{24}$ and $R^{34}$ represent alkyl group obtained by freeing hardened tallow fatty acid from carboxyl group:

compound (1-S)

$$CH_3\diagdown\overset{+}{N}\diagup R^{23} \quad Cl^-$$
$$CH_3\diagup\diagdown R^{33}$$

compound (1-T)

$$CH_3\diagdown\overset{+}{N}\diagup C_2H_4OCOR^{24} \quad Cl^-$$
$$CH_3\diagup\diagdown C_2H_4OCOR^{34}$$

compound (1-U)

$$CH_3—\overset{|CH_3}{\underset{|CH_3}{N^+}}—CH_2CHCH_2OCOR^{24} \quad Cl^-$$
$$\qquad\qquad\quad |\ OCOR^{34}$$

TABLE 1-2

| Structural formula of component (1-B) | |
|---|---|
| HO—CH$_2$—CH((CH$_2$)$_{15}$CH$_3$)—(CH$_2$)$_{17}$CH$_3$ | (1-B-1) |
| HO—CH$_2$—CH((CH$_2$)$_{11}$CH$_3$)—(CH$_2$)$_{13}$CH$_3$ | (1-B-2) |
| HO—CH$_2$—CH((CH$_2$)$_9$CH$_3$)—(CH$_2$)$_{11}$CH$_3$ | (1-B-3) |
| HO—CH$_2$—CH((CH$_2$)$_7$CH$_3$)—(CH$_2$)$_9$CH$_3$ | (1-B-4) |

TABLE 1-3

| Component (1-C) | |
|---|---|
| hardened tallow fatty acid | (1-C-1) |
| stearic acid | (1-C-2) |
| palmitic acid | (1-C-3) |

TABLE 1-4

| Component (1-E) | | |
|---|---|---|
| adduct of glycerol with EO | (MW 8,900) | (1-E-1) |
| adduct of glycerol with PO/EO (15:85) | (MW 10,000) | (1-E-2) |
| adduct of sorbitol with PO/EO (10:90) | (MW 15,000) | (1-E-3) |
| adduct of tetraethylenepentamine with PO/EO (2:98) | (MW 20,000) | (1-E-4) |
| adduct of polyethyleneimine (MW 3,000) with PO/EO (5:95) | (MW 300,000) | (1-E-5) |

(1) Evaluation method of storage stability

The softener compositions listed in Tables 1-5 and 1-6 were each stored in a hermetically sealed state at 5° C., 25° C. and 50° C. for 20 days and thereafter examined for appearance and fluidity under hermetically sealed conditions.

(2) Evaluation method of softness and elasticity (a) method of treatment

Commercially available cotton towel (1.5 kg) and acrylic jersey (0.5 kg) were washed five times with hard water of 3.5° DH and commercially available detergent "Attack" (a product of Kao Corporation, registered trademark) by the use of a 30 l washing machine to free them from textile treatment agent. A softener composition (6 ml) listed in Table 1-5 or 1-6 was thrown into the washing machine tub and the above towel and jersey were treated in the resulting bath at 25° C. under agitation for one minute.
(b) method of evaluation The cloths treated above were dried with air and allowed to stand in an air conditioned room of 25° C. and 60% RH for 24 hours. The resulting cloths were evaluated for softness and elasticity. This evaluation was conducted by comparing the cloths with a cloth treated with 10 cc of a softener composition containing 15% by weight of di(hardened tallow alkyl)-dimethylammonium chloride as control according to the following criteria:

+2: softer or more elastic than the control
+1: somewhat softer or somewhat more elastic than the control
0: equivalent to the control in softness or elasticity (3) Evaluation method of water absorption properties [Byreck's method]

The cloths treated in the same treatment manner as that employed in the evaluation of softness and elasticity were allowed to stand in an air conditioned room of 25° C. and 65% RH for 24 hours. Among the resulting cloths, the cotton towel was evaluated for water absorption properties.

The non-piled area of the cotton towel was cut into a rectangular piece (25 cm×2 cm). Water of 25° C. was provided to the air conditioned room. The piece was soaked in the water up to 2 cm from its lower end in a vertically hung state to make it absorb water. After 15 minutes, the ascent (height) of water was determined.

TABLE 1-5

| | No. | component (1-A) | component (1-B) | component (1-C) | component (1-D) | component (1-1-E) | other component |
|---|---|---|---|---|---|---|---|
| Ex. | 1-4 | 1-A-1 [25] | — | — | isopropanol [3.0] | — | — |
| | 1-5 | 1-A-2 [25] | — | — | isopropanol [3.0] | — | — |
| | 1-6 | 1-A-3 [25[ | — | — | isopropanol [3.0] | — | — |
| | 1-7 | 1-A-4 [25] | — | — | isopropanol [3.0] | — | — |
| | 1-8 | 1-A-5 [25] | — | — | isopropanol [3.0] | — | — |
| | 1-9 | 1-A-1 [23[ | 1-B-1 [2] | — | ethanol [4.0] | — | polyoxyethylene (p = 20) lauryl ether [2.5] |
| | 1-10 | 1-A-2 [23] | 1-B-2 [2] | — | ethanol [4.0] | — | polyoxyethylene (p = 20) lauryl ether [2.5] |
| | 1-11 | 1-A-3 [23] | 1-B-3 [2] | — | ethanol [4.0] | — | polyoxyethylene (p = 20) lauryl ether [2.5] |
| | 1-12 | 1-A-4 [23] | 1-B-2 [2] | — | ethanol [4.0] | — | polyoxyethylene (p = 20) lauryl ether [2.5] |
| | 1-13 | 1-A-5 [23] | 1-B-4 [2] | — | ethanol [4.0] | — | polyoxyethylene (p = 20) lauryl ether [2.5] |
| | 1-14 | 1-A-1 [25] | — | 1-C-1 [2] | isopropanol [3.0] | — | — |
| | 1-15 | 1-A-1 [25] | — | 1-C-2 [2] | isopropanol [3.0] | — | — |
| | 1-16 | 1-A-1 [25] | — | 1-C-3 [2] | isopropanol [3.0] | — | — |
| | 1-17 | 1-A-1 [25[ | — | — | isopropanol [3.0[ | 1-E-1 [2] | — |
| | 1-18 | 1-A-1 [25] | — | — | isopropanol [3.0] | 1-E-2 [2] | — |

TABLE 1-6

| | No. | component (1-A) | component (1-B) | component (1-C) | component (1-D) | component (1-1-E) | other component |
|---|---|---|---|---|---|---|---|
| Ex. | 1-19 | 1-A-1 [25] | — | — | isopropanol [3.0] | 1-E-3 [2] | — |
| | 1-20 | 1-A-1 [25] | — | — | isopropanol [3.0] | 1-E-4 [2] | — |
| | 1-21 | 1-A-1 [25] | — | — | isopropanol [3.0] | 1-E-5 [2] | — |
| | 1-22 | 1-A-1 [25] | — | — | — | — | — |
| | 1-23 | 1-A-2 [25] | — | — | — | — | — |
| Comp. | 1-1 | — | — | — | — | — | compd.(1-S) [25] |
| Ex. | 1-2 | — | 1-B-3 [2] | — | isopropanol [3.0] | — | compd.(1-S) [23] |
| | 1-3 | — | — | — | — | — | compd.(1-T) [25] |
| | 1-4 | — | 1-B-3 [2] | — | isopropanol [3.0] | — | compd.(1-T) [23] |
| | 1-5 | — | — | — | — | — | compd.(1-U) [25] |
| | 1-6 | — | 1-B-3 [2] | — | isopropanol [3.0] | — | compd.(1-U) [23] |

TABLE 1-7

| | No. | Performance | | Storage stability | | | Water absorption properties |
| | | soft-ness | elas-ticity | 5° C. | 25° C. | 50° C. | [cm] |
|---|---|---|---|---|---|---|---|
| Ex. | 1-4 | +1 | +1 | good | good | good | 9.5 |
| | 1-5 | +1 | +1 | good | good | good | 9.5 |
| | 1-6 | +1 | +1 | good | good | good | 9.8 |
| | 1-7 | +1 | +1 | good | good | good | 10.0 |
| | 1-8 | +0 | +1 | good | good | good | 10.0 |
| | 1-9 | +1 | +1 | good | good | good | 9.0 |
| | 1-10 | +1 | +2 | good | good | good | 9.0 |
| | 1-11 | +1 | +2 | good | good | good | 9.0 |
| | 1-12 | +1 | +2 | good | good | good | 9.5 |
| | 1-13 | +1 | +2 | good | good | good | 10.0 |
| | 1-14 | +1 | +2 | good | good | good | 10.0 |
| | 1-15 | +1 | +2 | good | good | good | 10.0 |
| | 1-16 | +1 | +2 | good | good | good | 10.0 |
| | 1-17 | +1 | +2 | good | good | good | 10.2 |
| | 1-18 | +1 | +2 | good | good | good | 10.2 |

TABLE 1-8

| | No. | Performance | | Storage stability | | | Water absorption properties |
| | | soft-ness | elas-ticity | 5° C. | 25° C. | 50° C. | [cm] |
|---|---|---|---|---|---|---|---|
| Ex. | 1-19 | +1 | +2 | good | good | good | 10.2 |
| | 1-20 | +1 | +2 | good | good | good | 10.2 |
| | 1-21 | +1 | +2 | good | good | good | 10.2 |
| | 1-22 | +1 | 0 | good | good | good | 10.5 |
| | 1-23 | +1 | 0 | good | good | good | 10.5 |
| Comp. Ex. | 1-1 | 0 | 0 | thickening | good | thickening | 7.0 |
| | 1-2 | 0 | 0 | gelation | good | thickening | 7.0 |
| | 1-3 | 0 | 0 | thickening | good | thickening | 7.2 |
| | 1-4 | 0 | 0 | thickening | good | thickening | 7.2 |
| | 1-5 | 0 | 0 | thickening | good | thickening | 6.8 |
| | 1-6 | 0 | 0 | thickening | good | thickening | 6.8 |

As apparent from the results given in Tables 1-7 and 1-8, all of the softener compositions according to the invention (1) caused little change in appearance or fluidity even after the lapse of time, being excellent in storage stability. Further, the cloths treated them were equivalent or superior to the controls in softness, elasticity and water absorption properties.

Example 2-1

Chloroacetic acid (24 g) and adduct (120 g) of 2-hexadecyleicosyl alcohol with 2 EO molecules were put in a four-necked flask fitted with a stirrer, a thermometer and a condenser. The contents were heated to 140° C. While formed water was distilled away, the contents were reacted at that temperature for 7 hours. The obtained reaction mixture was washed with water to remove excess chloroacetic acid. Thus, 131 g of a chloroacetate ester was obtained. A 50% aqueous solution (34 g) of dimethylamine and water (54 g) were added to the chloroacetate ester. The obtained mixture was heated to 55° C. and reacted at that temperature for 10 hours. After the completion of the reaction, the obtained reaction mixture was freed from excess dimethylamine by washing with water to give 125 g of a glycinate ester.

The glycinate ester (100 g), methyl chloride (8.4 g) and acetone (40 g) were charged into an autoclave fitted with a stirrer and a thermometer. The resulting mixture was reacted at 90° C. for 6 hours. After the completion of the reaction, the reaction mixture was subjected to crystallization with acetone and the obtained solid was dried to give 89 g of an objective product as a white powder.

It was confirmed by NMR and IR spectroscopic analyses that this product had the following structure:

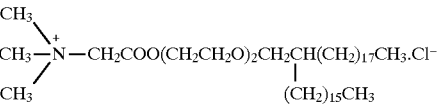

NMR spectrum (CDCl$_3$, internal standard: TMS)

3.66 ppm (s, 9H)  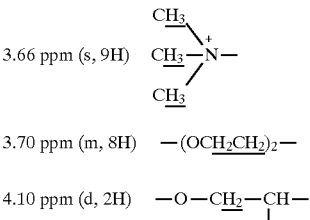

3.70 ppm (m, 8H)  —(OC$\underline{H}_2$C$\underline{H}_2$)$_2$—

4.10 ppm (d, 2H)  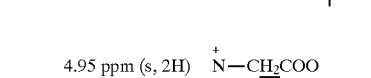

4.95 ppm (s, 2H)  $\overset{+}{N}$—C$\underline{H}_2$COO

IR spectrum (KBr tablet) 1746 cm$^{-1}$, 1470 cm$^{-1}$, 1206 cm$^{-1}$, 1106 cm$^{-1}$ Example 2-2

Chlorohexanoic acid (45 g) and adduct (206 g) of 2-hexadecyloicosyl alcohol with 2 EO molecules were put in a four-necked flask fitted with a stirrer, a thermometer and a condenser. The contents were heated to 140° C. While formed water was distilled away, the contents were reacted at that temperature for 10 hours. Thus, 243 g of a chlorohexanoate ester was obtained. A 50% aqueous solution (68 g) of dimethylamine and water (106 g) were added to the chlorohexanoate ester. The obtained mixture was heated to 60° C. and reacted at that temperature for 15 hours. After the completion of the reaction, the obtained reaction mixture was freed from excess dimethylamine by washing with water to give 239 g of a 6-aminohexanoate ester.

The 6-aminohexanoate ester (100 g), methyl chloride (7.8 g) and isopropyl alcohol (45 g) were charged into an autoclave fitted with a stirrer and a thermometer. The resulting mixture was reacted at 90° C. for 8 hours. After the completion of the reaction, the reaction mixture was subjected to crystallization with acetone and the obtained solid was dried to give 95 g of an objective product as a white powder.

It was confirmed by NMR and IR spectroscopic analyses that this product had the following structure:

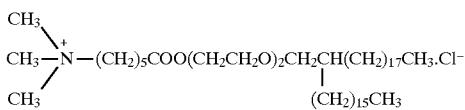

NMR spectrum (CDCl₃, internal standard: TMS)

2.43 ppm (t, 2H)  —CH₂C$\underline{H_2}$COO—

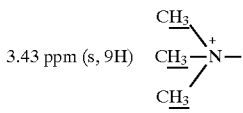

3.43 ppm (s, 9H)

3.90 ppm (d, 2H)  —COOC$\underline{H_2}$—

IR spectrum (KBr tablet) 1728 cm⁻¹, 1460 cm⁻¹, 1180 cm⁻¹, 1110 cm⁻¹

Example 2-3

Chloroacetic acid (19.5 g) and adduct (120 g) of 2-hexadecyleicosyl alcohol with 6 EO molecules were put in a four-necked flask fitted with a stirrer, a thermometer and a condenser. The contents were heated to 140° C. While formed water was distilled away, the contents were reacted at that temperature for 7 hours. After the completion of the reaction, the obtained reaction mixture was washed with water to remove excess chloroacetic acid. Thus, 132 g of a chloroacetate ester was obtained.

The chloroacetate ester (109 g), trimethylamine (8.9 g) and isopropyl alcohol (29 g) were charged into an autoclave fitted with a stirrer and a thermometer. The resulting mixture was reacted at 60° C. for 4 hours. After the completion of the reaction, the obtained reaction mixture was distilled to remove the isopropyl alcohol. Thus, 110 g of an objective product was obtained as a white solid.

It was confirmed by NMR and IR spectroscopic analyses that this product had the following structure:

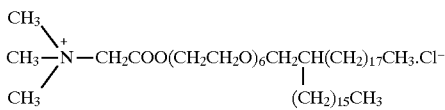

NMR spectrum (CDCl₃, internal standard: TMS)

3.65 ppm (bs)  O—(C$\underline{H_2}$C$\underline{H_2}$)₆—,

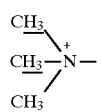

4.10 ppm (d)   —O—C$\underline{H_2}$—CH—

4.95 ppm (s)   $\overset{+}{N}$—C$\underline{H_2}$COO

IR spectrum (KBr tablet) 1740 cm⁻¹, 1462 cm⁻¹, 1208 cm⁻¹, 1118 cm¹

Example 2-4

Chloroacetic acid (16.6 g) and adduct (140 g) of 2-hexadecyleicosyl alcohol with 12 EO molecules were put in a four-necked flask fitted with a stirrer, a thermometer and a condenser. The contents were heated to 140° C. While formed water was distilled away, the contents were reacted at that temperature for 3 hours. The obtained reaction mixture was washed with water to remove excess chloroacetic acid. Thus, 142 g of a chloroacetate ester was obtained.

The chloroacetate ester (125 g), trimethylamine (6.9 g) and isopropyl alcohol (33 g) were charged into an autoclave fitted with a stirrer and a thermometer. The resulting mixture was reacted at 60° C. for 4 hours. After the completion of the reaction, the obtained reaction mixture was distilled to remove the isopropyl alcohol. Thus, 129 g of an objective product was obtained as a white solid.

It was confirmed by NMR and IR spectroscopic analyses that this product had the following structure:

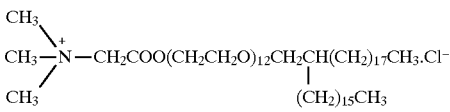

NMR spectrum (CDCl₃, internal standard: TMS)

3.67 ppm (bs)  —(C$\underline{H_2}$C$\underline{H_2}$O)₁₂—,

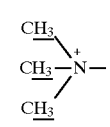

4.10 ppm (d)   —O—C$\underline{H_2}$—CH—

4.92 ppm (s)   $\overset{+}{N}$—C$\underline{H_2}$COO

IR spectrum (KBr tablet) 1748 cm⁻¹, 1466 cm⁻¹, 1206 cm⁻¹, 1118 cm⁻¹

Synthesis Example 2-1

Chloroacetic acid (34 g) and adduct (163 g) of 2-dodecylhexadecyl alcohol with 2 EO molecules were put in a four-necked flask fitted with a stirrer, a thermometer and a condenser. The contents were heated to 140° C. While formed water was distilled away, the contents were reacted at that temperature for 5 hours. After the completion of the reaction, the obtained reaction mixture was washed with water to remove excess chloroacetic acid. Thus, 178 g of a chloroacetate ester was obtained.

The chloroacetate ester (105 g), trimethylamine (11.8 g) and isopropyl alcohol (29 g) were charged into an autoclave fitted with a stirrer and a thermometer. The resulting mixture was reacted at 60° C. for 4 hours. After the completion of the reaction, the obtained reaction mixture was subjected to crystallization with acetone and the obtained solid was dried. Thus, 98 g of an objective product was obtained as a white powder.

It was confirmed by NMR and IR spectroscopic analyses that this product had the following structure:

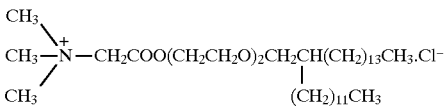

NMR spectrum (CDCl$_3$, internal standard: TMS)

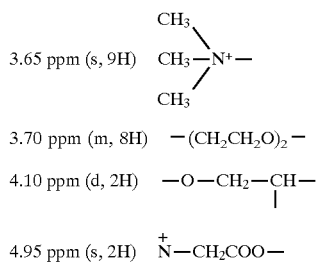

3.65 ppm (s, 9H)  CH$_3$—N$^+$— (with CH$_3$ groups)

3.70 ppm (m, 8H)  —(CH$_2$CH$_2$O)$_2$—

4.10 ppm (d, 2H)  —O—CH$_2$—CH—

4.95 ppm (s, 2H)  $\overset{+}{\text{N}}$—CH$_2$COO—

IR spectrum (KBr tablet) 1746 cm$^{-1}$, 1470 cm$^{-1}$, 1206 cm$^{-1}$, 1106 cm$^{-1}$

Synthesis Example 2-2

Chloroacetic acid (34 g) and adduct (127 g) of 2-octyldodecyl alcohol with 2 EO molecules were put in a flask fitted with a stirrer, a thermometer and a condenser. The contents were heated to 140° C. While formed water was distilled away, the contents were reacted at that temperature for 5 hours. The obtained reaction mixture was washed with water to remove excess chloroacetic acid. Thus, 135 g of a chloroacetate ester was obtained.

The chloroacetate ester (100 g), trimethylamine (14.0 g) and isopropyl alcohol (28 g) were charged into an autoclave fitted with a stirrer and a thermometer. The resulting mixture was reacted at 60° C. for 4 hours. After the completion of the reaction, the reaction mixture was subjected crystallization with acetone and the obtained solid was dried. Thus, 95 g of an objective product was obtained as a white powder.

It was confirmed by NMR and IR spectroscopic analyses that this product had the following structure:

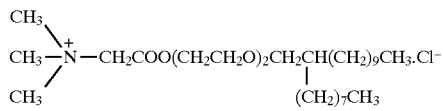

CH$_3$—N$^+$(CH$_3$)(CH$_3$)—CH$_2$COO(CH$_2$CH$_2$O)$_2$CH$_2$CH(CH$_2$)$_9$CH$_3$·Cl$^-$ with (CH$_2$)$_7$CH$_3$ branch NMR spectrum (CDCl$_3$, internal standard:TMS)

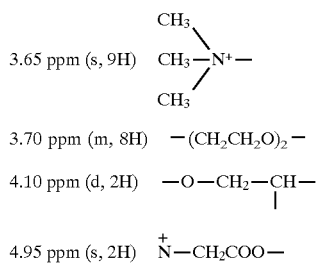

3.65 ppm (s, 9H)  CH$_3$—N$^+$—

3.70 ppm (m, 8H)  —(CH$_2$CH$_2$O)$_2$—

4.10 ppm (d, 2H)  —O—CH$_2$—CH—

4.95 ppm (s, 2H)  $\overset{+}{\text{N}}$—CH$_2$COO—

IR spectrum (KBr tablet) 1744 cm$^{-1}$, 1470 cm$^{-1}$, 1206 cm$^{-1}$, 1110 cm$^{-1}$ The quaternary ammonium salts prepared in Examples 2-1 to 2-4 and Synthesis Examples 2-1 and 2-2 are listed in Table 2-1.

TABLE 2-1

| | Structural formula of component (2-A) (quaternary ammonium salt (2-I)) |
|---|---|
| Ex. 2-1 | (CH$_3$)$_3$N$^+$—CH$_2$COO(CH$_2$CH$_2$O)$_2$CH$_2$CH((CH$_2$)$_{15}$CH$_3$)(CH$_2$)$_{17}$CH$_3$·Cl$^-$ (2-A-1) |
| Ex. 2-2 | (CH$_3$)$_3$N$^+$—(CH$_2$)$_5$COO(CH$_2$CH$_2$O)$_2$CH$_2$CH((CH$_2$)$_{15}$CH$_3$)(CH$_2$)$_{17}$CH$_3$·Cl$^-$ (2-A-2) |
| Ex. 2-3 | (CH$_3$)$_3$N$^+$—CH$_2$COO(CH$_2$CH$_2$O)$_6$CH$_2$CH((CH$_2$)$_{15}$CH$_3$)(CH$_2$)$_{17}$CH$_3$·Cl$^-$ (2-A-3) |
| Ex. 2-4 | (CH$_3$)$_3$N$^+$—CH$_2$COO(CH$_2$CH$_2$O)$_{12}$CH$_2$CH((CH$_2$)$_{15}$CH$_3$)(CH$_2$)$_{17}$CH$_3$·Cl$^-$ (2-A-4) |
| Synth. Ex. 2-1 | (CH$_3$)$_3$N$^+$—CH$_2$COO(CH$_2$CH$_2$O)$_2$CH$_2$CH((CH$_2$)$_{11}$CH$_3$)(CH$_2$)$_{13}$CH$_3$·Cl$^-$ (2-A-5) |
| Synth. Ex. 2-2 | (CH$_3$)$_3$N$^+$—CH$_2$COO(CH$_2$CH$_2$O)$_2$CH$_2$CH((CH$_2$)$_7$CH$_3$)(CH$_2$)$_9$CH$_3$·Cl$^-$ (2-A-6) |

Examples 2-5 to 2-26 and Comparative Examples 2-1 to 2-6

Softener compositions (adjusted to pH3) were prepared, which each comprised a quaternary ammonium salt (2-I) (component (2-A)) listed in Table 2-1, a higher alcohol (component (2-B)) listed in Table 2-2, a fatty acid (component (2-C)) listed in Table 2-3, a lower alcohol (component (2-D)), a polyalkylene oxide compound (component (2-E)) listed in Table 2-4 and so forth in amounts specified in Table 2-5 or 2-6. The storage stability of these softener compositions and the softness, elasticity and water absorption properties of textiles treated with these softener compositions were evaluated by the methods which will be described below. The results are given in Tables 2-7 and 2-8.

In Comparative Examples, the following compounds (2-S) to (2-U) were used, wherein R$^{23}$ and R$^{33}$ represent alkyl group obtained by replacing the carboxyl group of hardened tallow fatty acid by methylene group; and R$^{24}$ and R$^{34}$ represent alkyl group obtained by freeing hardened tallow fatty acid from carboxyl group:

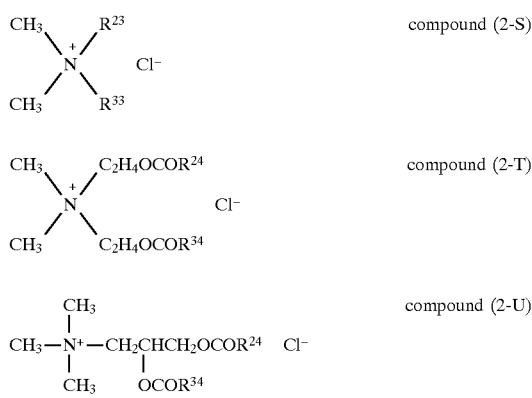

compound (2-S)

compound (2-T)

CH₃—N⁺—CH₂CHCH₂OCOR²⁴   Cl⁻
   |         |
   CH₃     OCOR³⁴ compound (2-U)

TABLE 2-2

| Structural formula of component (2-B) | |
|---|---|
| HO—CH₂—CH—(CH₂)₁₇CH₃<br>　　　　　\|<br>　　　　(CH₂)₁₅CH₃ | (2-B-1) |
| HO—CH₂—CH—(CH₂)₁₃CH₃<br>　　　　　\|<br>　　　　(CH₂)₁₁CH₃ | (2-B-2) |
| HO—CH₂—CH—(CH₂)₁₁CH₃<br>　　　　　\|<br>　　　　(CH₂)₉CH₃ | (2-B-3) |
| HO—CH₂—CH—(CH₂)₉CH₃<br>　　　　　\|<br>　　　　(CH₂)₇CH₃ | (2-B-34) |

TABLE 2-3

| Component (2-C) | |
|---|---|
| hardened tallow fatty acid | (2-C-1) |
| stearic acid | (2-C-2) |
| palmitic acid | (2-C-3) |

TABLE 2-4

| Component (2-E) | | |
|---|---|---|
| adduct of glycerol with EO | (MW 8,900) | (2-E-1) |
| adduct of glycerol with PO/EO (15:85) | (MW 10,000) | (2-E-2) |
| adduct of sorbitol with PO/EO (10:90) | (MW 15,000) | (2-E-3) |
| adduct of tetraethylenepentamine with PO/EO (2:98) | (MW 20,000) | (2-E-4) |
| adduct of polyethyleneimine (MW 3,000) with PO/EO (5:95) | (MW 300,000) | (2-E-5) |

(1) Evaluation method of storage stability

The softener compositions listed in Tables 2-5 and 2-6 were each stored in a hermetically sealed state at 5° C., 25° C. and 50° C. for 20 days and thereafter examined for appearance and fluidity under hermetically sealed conditions.

(2) Evaluation method of softness and elasticity (a) method of treatment

Commercially available cotton towel (1.5 kg) and acrylic jersey (0.5 kg) were washed five times with hard water of 3.5° DH and a commercially available detergent "Attack" (a product of Kao Corporation, registered trademark) by the use of a 30 l washing machine to free them from textile treating agent. A softener composition (6 ml) listed in Table 5 or 6 was thrown into the washing machine tub and the above towel and jersey were treated in the resulting bath at 25° C. under agitation for one minute.

(b) method of evaluation

The cloths treated above were dried with air and allowed to stand in an air conditioned room of 25° C. and 60% RH for 24 hours. The resulting cloths were evaluated for softness and elasticity. This evaluation was conducted by comparing them with those treated with 10 cc of a softener composition containing 15% by weight of di(hardened tallow alkyl)dimethylammonium chloride as control according to the following criteria:

+2: softer or more elastic than the control

+1: somewhat softer or somewhat more elastic than the the control

0: equivalent to the control in softness or elasticity (3) Evaluation method of water absorption properties [13Byreck's method]

The cloths treated in the same treatment manner as that employed in the evaluation of softness and elasticity were allowed to stand in an air conditioned room of 25° C. and 65% RH for 24 hours. Among the resulting cloths, the cotton towel was evaluated for water absorption properties.

The non-piled area of the cotton towel was cut into a rectangular piece (25 cm×2 cm). Water of 25° C. was provided to the air conditioned room. The piece was soaked in the water up to 2 cm from its lower end in a vertically hung state to make it absorb water. After 15 minutes, the ascent (height) of water was determined.

TABLE 2-5

| | | Softener compn.* | | | | |
|---|---|---|---|---|---|---|
| No. | component (2-A) | component (2-B) | component (2-C) | component (2-D) | component (2-E) | other component |
| Ex. 2-5 | 2-A-1 [20] | — | — | isopropanol [5] | — | — |
| 2-6 | 2-A-2 [20] | — | — | isopropanol [5] | — | — |
| 2-7 | 2-A-3 [20] | — | — | isopropanol [5] | — | — |
| 2-8 | 2-A-4 [20] | — | — | isopropanol [5] | — | — |
| 2-9 | 2-A-5 [20] | — | — | isopropanol [5] | — | — |
| 2-10 | 2-A-6 [20] | — | — | isopropanol [5] | — | — |
| 2-11 | 2-A-1 [20] | 2-B-1 [2] | — | isopropanol [5] | — | polyoxyethylene (p = 20) lauryl ether [2] |
| 2-12 | 2-A-2 [20] | 2-B-2 [2] | — | isopropanol [5] | — | polyoxyethylene (p = 20) lauryl ether [2] |
| 2-13 | 2-A-3 [20] | 2-B-2 [2] | — | ethanol [5] | — | polyoxyethylene (p = 20) lauryl ether [2] |
| 2-14 | 2-A-4 [20] | 2-B-3 [2] | — | ethanol [5] | — | polyoxyethylene (p = 20) lauryl ether [2] |
| 2-15 | 2-A-5 [20] | 2-B-4 [2] | — | ethanol [5] | — | polyoxyethylene (p = 20) lauryl ether [2] |
| 2-16 | 2-A-6 [20] | 2-B-4 [2] | — | ethanol [5] | — | polyoxyethylene (p = 20) lauryl ether [2] |
| 2-17 | 2-A-1 [20] | — | 2-C-1 [2] | isopropanol [5] | 2-E-1 [2] | — |
| 2-18 | 2-A-1 [20] | — | 2-C-3 [2] | isopropanol [5] | 2-E-2 [2] | polyoxyethylene (p = 20) lauryl ether [2] |

TABLE 2-6

| | | Softener compn.* | | | | |
|---|---|---|---|---|---|---|
| No. | component (2-A) | component (2-B) | component (2-C) | component (2-D) | component (2-E) | other component |
| Ex. 2-19 | 2-A-1 [20] | — | — | ethanol [5] | 2-E-3 [2] | — |
| 2-20 | 2-A-1 [20] | — | 2-C-1 [2] | ethanol [5] | 2-E-4 [2] | — |
| 2-21 | 2-A-1 [20] | — | 2-C-1 [2] | ethanol [5] | 2-E-5 [2] | — |
| 2-22 | 2-A-2 [20] | — | 2-C-1 [2] | isopropanol [5] | 2-E-1 [2] | — |
| 2-23 | 2-A-2 [20] | — | — | isopropanol [5] | 2-E-2 [2] | polyoxyethylene (p = 20) lauryl ether [2] |
| 2-24 | 2-A-2 [20] | — | — | isopropanol [5] | 2-E-3 [2] | — |
| 2-25 | 2-A-2 [20] | — | 2-C-2 [2] | isopropanol [5] | 2-E-4 [2] | — |
| 2-26 | 2-A-2 [20] | — | 2-C-2 [2] | isopropanol [5] | 2-E-5 [2] | — |
| Comp. Ex. 2-1 | — | 2-B-1 [2] | — | isopropanol [5] | — | compd. (2-S) [20] |
| 2-2 | — | — | — | — | — | compd. (2-S) [25] |
| 2-3 | — | — | — | isopropanol [5] | — | compd. (2-T) [20] |
| 2-4 | — | 2-B-1 [2] | — | — | — | compd. (2-T) [25] |
| 2-5 | — | — | — | isopropanol [5] | — | compd. (2-U) [20] |
| 2-6 | — | — | — | — | — | compd. (2-U) [25] | note)
*each figure in brackets represents the content (wt %) of each component in the composition, and the balance is composed of water.

TABLE 2-7

| | | Performance | | Storage stability | | | Water absorption properties |
|---|---|---|---|---|---|---|---|
| No. | | soft-ness | elas-ticity | 5° C. | 25° C. | 50° C. | [cm] |
| Ex. | 2-5 | +2 | +2 | good | good | good | 9.2 |
| | 2-6 | +2 | +2 | good | good | good | 9.1 |
| | 2-7 | +1 | +1 | good | good | good | 9.5 |
| | 2-8 | 0 | +1 | good | good | good | 10.0 |
| | 2-9 | +1 | +2 | good | good | good | 10.1 |
| | 2-10 | +2 | +2 | good | good | good | 9.1 |
| | 2-11 | +2 | +2 | good | good | good | 9.6 |
| | 2-12 | +2 | +2 | good | good | good | 9.5 |
| | 2-13 | +1 | +2 | good | good | good | 10.0 |
| | 2-14 | +1 | +1 | good | good | good | 10.2 |
| | 2-15 | +2 | +1 | good | good | good | 9.0 |
| | 2-16 | +2 | +2 | good | good | good | 9.2 |
| | 2-17 | +2 | +2 | good | good | good | 9.4 |
| | 2-18 | +1 | +2 | good | good | good | 10.3 |

TABLE 2-8

| | | Performance | | Storage stability | | | Water absorption properties |
|---|---|---|---|---|---|---|---|
| No. | | soft-ness | elas-ticity | 5° C. | 25° C. | 50° C. | [cm] |
| Ex. | 2-19 | +2 | +2 | good | good | good | 9.2 |
| | 2-20 | +2 | +2 | good | good | good | 9.0 |
| | 2-21 | +2 | +2 | good | good | good | 9.0 |
| | 2-22 | +2 | +2 | good | good | good | 9.4 |
| | 2-23 | +2 | +2 | good | good | good | 9.5 |
| | 2-24 | +2 | +2 | good | good | good | 9.3 |
| | 2-25 | +2 | +2 | good | good | good | 10.1 |
| | 2-26 | +2 | +2 | good | good | good | 9.1 |
| Comp. Ex. | 2-1 | 0 | 0 | thickening | good | thickening | 8.2 |
| | 2-2 | 0 | 0 | gelation | good | thickening | 7.0 |
| | 2-3 | 0 | 0 | thickening | good | thickening | 7.2 |
| | 2-4 | 0 | 0 | thickening | good | thickening | 6.8 |
| | 2-5 | 0 | 0 | thickening | good | thickening | 8.2 |
| | 2-6 | 0 | 0 | thickening | good | thickening | 7.3 |

As apparent from the results given in Tables 2-7 and 2-8, all of the softener compositions according to the present invention caused little change in appearance or fluidity even after the lapse of time, being excellent in storage stability. Further, the cloths treated with them were equivalent or superior to the controls in softness, elasticity and water absorption properties.

The quaternary ammonium salt used are listed in Table 3-1.

TABLE 3-1

| Component (3-B) | Synth. method |
|---|---|
| $CH_3$<br>$\phantom{xx}\backslash_{+}$<br>$CH_3-N-CH_2COOCH_2CH(CH_2)_{17}CH_3.Cl^-$<br>$\phantom{xx}/\phantom{xxxxxxxxxxxx}\|$<br>$CH_3\phantom{xxxxxxxxxxx}(CH_2)_{15}CH_3$<br>(3-B-1) | Ex. 1-1 |
| $CH_3$<br>$\phantom{xx}\backslash_{+}$<br>$CH_3-N-CH_2CH_2CH_2COOCH_2CH(CH_2)_{17}CH_3.Cl^-$<br>$\phantom{xx}/\phantom{xxxxxxxxxxxxxxxxxxxx}\|$<br>$CH_3\phantom{xxxxxxxxxxxxxxxxxxx}(CH_2)_{15}CH_3$<br>(3-B-2) | Ex. 1-2 |
| $CH_3$<br>$\phantom{xx}\backslash_{+}$<br>$CH_3-N-(CH_2)_5COOCH_2CH(CH_2)_{17}CH_3.Cl^-$<br>$\phantom{xx}/\phantom{xxxxxxxxxxxx}\|$<br>$CH_3\phantom{xxxxxxxxxxx}(CH_2)_{15}CH_3$<br>(3-B-3) | Ex. 1-3 |
| $CH_3$<br>$\phantom{xx}\backslash_{+}$<br>$CH_3-N-CH_2COOCH_2CH(CH_2)_{13}CH_3.Cl^-$<br>$\phantom{xx}/\phantom{xxxxxxxxxxxx}\|$<br>$CH_3\phantom{xxxxxxxxxxx}(CH_2)_{11}CH_3$<br>(3-B-4) | Synth. Ex. 1-1 |
| $CH_3$<br>$\phantom{xx}\backslash_{+}$<br>$CH_3-N-CH_2COOCH_2CH(CH_2)_9CH_3.Cl^-$<br>$\phantom{xx}/\phantom{xxxxxxxxxxxx}\|$<br>$CH_3\phantom{xxxxxxxxxxx}(CH_2)_7CH_3$<br>(3-B-5) | Synth. Ex. 1-2 |

Examples 3-1 to 3-41 and Comparative Examples 3-1 to 3-16

Liquid softener compositions were prepared by the use of components (3-A) listed in Tables 3-2 and 3-3, components (3-B) listed in Table 3-1, components (3-C) listed in Table 3-4, components (3-D) listed in Table 3-5, components (3-E) listed in Table 3-6, components (3-F) listed in Table 3-7 and the following surfactants (3-X) and (3-Y) according to the formulations specified in Tables 3-8 to 3-13.

In Comparative Examples, the following compounds (3-S) to (3-U) were used surfactant (3-X): polyoxyethylene (p = 20) lauryl ether surfactant (3-Y): polyoxyethylene (p = 20) stearylamine compound (3-S) 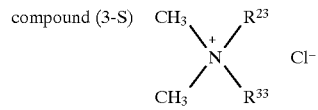

compound (3-T) 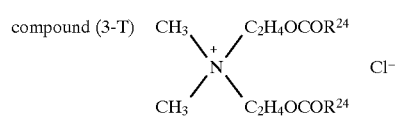

compound (3-U) 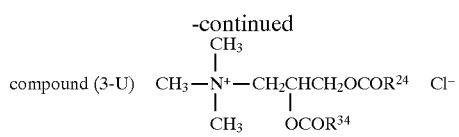

(wherein $R^{23}$ and $R^{33}$ represent alkyl group obtained by replacing the carboxyl group of hardened tallow fatty acid by methylene group; and $R^{24}$ and $R^{34}$ represent alkyl group obtained by freeing hardened tallow fatty acid from carboxyl group).

TABLE 3-2

| | | Component (3-A) | |
|---|---|---|---|
| | Synth. process | Wt. ratio of (3-I)/(3-II)/ (3-III)/(3-IV) | Griffin's HLB |
| 3-A-1 | compound prepd. from methyl ester of hardened palm stearic acid, glycerol and EO*[1] at mol. ratio of 2:1:4 by synth. process (3-ii) | 0.150/0.444/ 0.393/0.013 | 6.69 |
| 3-A-2 | compound prepd. from semihardened tallow*[2], glycerol and EO at mol. ratio of 1:0.2:9.6 by synth. process (3-iv) | 0.045/0.306/ 0.647/0.002 | 7.80 |
| 3-A-3 | compound prepd. from tallow, glycerol and EO at mol. ratio of 1:1:8 by synth. process (3-ii) | 0.301/0.449/ 0.199/0.051 | 7.82 |
| 3-A-4 | compound prepd. from palm stearin, glycerol and EO at mol. ratio of 1:0.5:12 by synth. process (3-ii) | 0.164/0.444/ 0.375/0.017 | 9.09 |
| 3-A-5 | compound prepd. from tallow, glycerol and EO at mol. ratio of 2.5:1:12 by synth. process (3-iii) | 0.048/0.312/ 0.638/0.002 | 9.43 |
| 3-A-6 | compound prepd. from hardened tallow, glycerol and EO at mol. ratio of 1:0.25:15 by synth. process (3-ii) [component (b-1) used in Example of JP-A-57632/1994] | 0.068/0.352/ 0.576/0.004 | 9.63 |
| 3-A-7 | compound prepd. from methyl ester of palm kernel oil fatty acid, glycerol and EO at mol. ratio of 1.7:1:6 by synth. process (3-iv) | 0.255/0.454/ 0.250/0.041 | 9.76 |

TABLE 3-3

| | | Component (3-A) | |
|---|---|---|---|
| | Synth. process | Wt. ratio of (3-I)/(3-II)/ (3-III)/(3-IV) | Griffin's HLB |
| 3-A-8 | compound prepd. from tallow fatty acid, glycerol and EO at mol. ratio of 2:1:10 by synth. process (3-i) | 0.167/0.444/ 0.370/0.019 | 9.78 |
| 3-A-9 | compound prepd. from methyl ester of semihardened palm stearic acid*[3], glycerol and EO at mol. ratio of 1.8:1:10 by synth. process (3-iv) | 0.230/0.454/ 0.282/0.035 | 10.52 |
| 3-A-10 | compound prepd. from semihardened tallow, glycerol and EO at mol. ratio of 1:0.5:18 by synth. process (3-ii) | 0.172/0.444/ 0.364/0.020 | 10.54 |
| 3-A-11 | compound prepd. from methyl ester of palm kernel oil fatty acid, glycerol and EO at mol. ratio of 2:1:10 by synth. process (3-ii) | 0.174/0.444/ 0.360/0.021 | 10.95 |
| 3-A-12 | compound prepd. from hardened palm stearin, glycerol and EO at mol. ratio of 1:0.25:20 by synth. process (3-ii) | 0.072/0.357/ 0.567/0.005 | 11.09 |
| 3-A-13 | compound prepd. from coconut oil fatty acid, glycerol and EO at mol. ratio of 2:1:10 by synth. process | 0.176/0.444/ 0.358/0.022 | 11.18 |

TABLE 3-3-continued

| | Component (3-A) | | |
|---|---|---|---|
| | Synth. process | Wt. ratio of (3-I)/(3-II)/ (3-III)/(3-IV) | Griffin's HLB |
| | (3-iii) | | |
| 3-A-14 | compound prepd. from palm oil fatty acid, glycerol and EO at mol. ratio of 2:1:16 by synth. process (3-iii) | 0.178/0.444/ 0.355/0.022 | 11.79 |
| 3-A-15 | compound prepd. from palm oil, glycerol and EO at mol. ratio of 1:1:24 by synth. process (3-ii) | 0.327/0.423/ 0.173/0.077 | 11.97 | notes)
*1: EO represents ethylene oxide.
*2: semihardened tallow is a 1:1 (by weight) mixture of tallow with hardened tallow
*3: methyl ester of semihardened palm stearic acid is a 1:1 (by weight) mixture of methyl ester of palm stearic acid with methyl ester of hardened palm stearic acid

TABLE 3-4

| | Component (3-C) |
|---|---|
| 3-C-1 | $HO-CH_2-CH(-(CH_2)_{17}CH_3)(CH_2)_{15}CH_3$ |
| 3-C-2 | $HO-CH_2-CH(-(CH_2)_{13}CH_3)(CH_2)_{11}CH_3$ |
| 3-C-3 | $HO-CH_2-CH(-(CH_2)_{11}CH_3)(CH_2)_9CH_3$ |
| 3-C-4 | $HO-CH_2-CH(-(CH_2)_9CH_3)(CH_2)_7CH_3$ |

TABLE 3-5

| | Component (3-D) |
|---|---|
| 3-D-1 | hardened tallow fatty acid |
| | semihardened tallow fatty acid |
| 3-D-2 | [75:25 (by weight) mixture of tallow with hardened tallow] |
| 3-D-3 | palm oil fatty acid |
| 3-D-4 | palm stearic acid |
| 3-D-5 | stearic acid |
| 3-D-6 | oleic acid |
| 3-D-7 | hardened palm oil fatty acid |
| 3-D-8 | palm kernel oil fatty acid |
| 3-D-9 | coconut oil fatty acid |
| 3-D-10 | lauric acid |
| 3-D-11 | tallow fatty acid |
| 3-D-12 | hardened palm stearic acid |

TABLE 3-6

| | Component (3-E) |
|---|---|
| 3-E-1 | ethanol |
| 3-E-2 | isopropanol |

TABLE 3-7

| | Component (3-F) | |
|---|---|---|
| 3-F-1 | adduct of glycerol with EO | (MW 8,900) |
| 3-F-2 | adduct of glycerol with PO/EO (15:85) | (MW 10,000) |
| 3-F-3 | adduct of sorbitol with PO/EO (10:90) | (MW 15,000) |
| 3-F-4 | adduct of tetraethylenepentamine with PO/EO (2:98) | (MW 20,000) |
| 3-F-5 | adduct of polyethyleneimine (MW: 3,000) with PO/EO (5:95) | (MW 300,000) |

The softness, elasticity and water absorption properties of textiles treated with the liquid softener compositions prepared in Examples 3-1 to 3-41 and Comparative Examples 3-1 to 3-16 and the storage stability of the compositions were evaluated by the following methods. The results are given in Tables 3-8 to 3-13.

<Evaluation of softness and elasticity>

Commercially available cotton towel and pieces or acrylic textile and polyester textile were washed five times with a commercially available detergent "Attack" (a product of Kao Corporation, registered trademark) to free them from textile treatment agents. A liquid softener composition prepared above was thrown into a tub in an amount of 0.5% based on the total weight of the cloths to be treated. The cloths washed above were treated in the resulting bath at 25° C. and a bath ratio of 1/10 under agitation for 3 minutes, dried with air in a room and allowed to stand in an air-conditioned room of 200° C. and 65% RH for 24 hours.

The resulting cloths were evaluated for softness and elasticity.

The evaluation was conducted by comparing the cloths with those treated with the softener composition of Comparative Example 3–16 as control according to the following criteria:

softness:
  +2: softer or more elastic than the control
  +1: somewhat softer or somewhat more elastic than the control
  0: equivalent to the control in softness or elasticity
  −1: the control is somewhat softer or somewhat more elastic
  −2: the control is softer or more elastic <Evaluation of water absorption properties [Byreck's method]>

The cloths treated in the same treatment manner as that employed in the evaluation of softness and elasticity were allowed to stand in an air conditioned room of 25° C. and 65% RH for 24 hours. Among the resulting cloths, the cotton towel was evaluated for water absorption properties.

The non-piled area of the cotton towel was cut into a rectangular piece (25 cm×2 cm). Water of 25° C. was provided to the air conditioned room. The piece was soaked in the water up to 2 cm from its lower end in a vertically hung state to make it absorb water. After 15 minutes, the ascent (height) of water was determined.

<Evaluation method of storage stability>

The liquid softener compositions prepared above were stored in a hermetically sealed state at 20° C. for 20 days and examined for appearance and fluidity with the eye. The case wherein no change was observed in the appearance or fluidity is shown by "good", while the case wherein a change was observed therein is shown by the kind of the change.

TABLE 3-8

|  | Component (3-A) | Component (3-B) | Component (3-C) | Component (3-D) | Component (3-E) | Component (3-F) | Other component | Soft-ness | Elastic-ity | Storage stability | absorption properties (cm) |
|---|---|---|---|---|---|---|---|---|---|---|---|
| Ex. 3-1 | 3-A-1 (4) | 3-B-1 (16) | — | — | 3-E-2 (3) | — | — | +2 | +2 | good | 13.0 |
| 3-2 | 3-A-2 (4) | 3-B-1 (16) | — | — | 3-E-2 (3) | — | — | +2 | +2 | good | 13.6 |
| 3-3 | 3-A-3 (4) | 3-B-1 (16) | — | — | 3-E-2 (3) | — | — | +2 | +2 | good | 13.1 |
| 3-4 | 3-A-4 (4) | 3-B-1 (16) | — | — | 3-E-2 (3) | — | — | +2 | +2 | good | 12.6 |
| 3-5 | 3-A-5 (4) | 3-B-1 (16) | — | — | 3-E-2 (3) | — | — | +2 | +2 | good | 12.9 |
| 3-6 | 3-A-6 (4) | 3-B-1 (16) | — | — | 3-E-2 (3) | — | — | +2 | +2 | good | 13.0 |
| 3-7 | 3-A-7 (4) | 3-B-1 (16) | — | — | 3-E-2 (3) | — | — | +2 | +2 | good | 13.5 |
| 3-8 | 3-A-8 (4) | 3-B-1 (16) | — | — | 3-E-2 (3) | — | — | +2 | +2 | good | 12.7 |
| 3-9 | 3-A-9 (4) | 3-B-1 (16) | — | — | 3-E-2 (3) | — | — | +2 | +2 | good | 12.4 |
| 3-10 | 3-A-10 (4) | 3-B-1 (16) | — | — | 3-E-2 (3) | — | — | +2 | +2 | good | 13.5 |
| 3-11 | 3-A-11 (4) | 3-B-1 (16) | — | — | 3-E-2 (3) | — | — | +2 | +2 | good | 13.6 |
| 3-12 | 3-A-12 (4) | 3-B-1 (16) | — | — | 3-E-2 (3) | — | — | +2 | +2 | good | 12.8 |

TABLE 3-9

|  | Component (3-A) | Component (3-B) | Component (3-C) | Component (3-D) | Component (3-E) | Component (3-F) | Other component | Soft-ness | Elastic-ity | Storage stability | Water absorption properties (cm) |
|---|---|---|---|---|---|---|---|---|---|---|---|
| Ex. 3-13 | 3-A-13 (4) | 3-B-1 (16) | — | — | 3-E-2 (3) | — | — | +2 | +2 | good | 12.6 |
| 3-14 | 3-A-14 (4) | 3-B-1 (16) | — | — | 3-E-2 (3) | — | — | +2 | +2 | good | 13.4 |
| 3-15 | 3-A-15 (4) | 3-B-1 (16) | — | — | 3-E-2 (3) | — | — | +2 | +2 | good | 13.4 |
| 3-16 | 3-A-15 (4) | 3-B-1 (16) | 3-C-1 (2) | — | 3-E-1 (3) | — | surfactant (3-X) (2) | +2 | +2 | good | 14.0 |
| 3-17 | 3-A-15 (4) | 3-B-2 (16) | 3-C-1 (2) | — | 3-E-1 (3) | — | surfactant (3-X) (2) | +2 | +2 | good | 13.2 |
| 3-18 | 3-A-15 (4) | 3-B-3 (16) | 3-C-3 (2) | — | 3-E-1 (3) | — | surfactant (3-X) (2) | +2 | +2 | good | 12.8 |
| 3-19 | 3-A-15 (4) | 3-13-4 (16) | 3-C-2 (2) | — | 3-E-1 (3) | — | surfactant (3-X) (2) | +2 | +2 | good | 13.2 |
| 3-20 | 3-A-15 (4) | 3-B-5 (16) | 3-C-4 (2) | — | 3-E-1 (3) | — | surfactant (3-X) (2) | +2 | +2 | good | 12.9 |
| 3-21 | 3-A-4 (5) | 3-B-1 (20) | — | — | 3-E-2 (3) | 3-F-1 (1.5) | surfactant (3-X) (2) | +2 | +2 | good | 12.7 |
| 3-22 | 3-A-4 (5) | 3-B-1 (20) | — | — | 3-E-2 (3) | 3-F-2 (1.5) | surfactant (3-X) (2) | +2 | +2 | good | 12.3 |
| 3-23 | 3-A-4 (5) | 3-B-1 (20) | — | — | 3-E-2 (3) | 3-F-3 (1.5) | surfactant (3-X) (2) | +2 | +2 | good | 12.4 |

TABLE 3-10

|  | Component (3-A) | Component (3-B) | Component (3-C) | Component (3-D) | Component (3-E) | Component (3-F) | Other component | Soft-ness | Elas-ticity | Storage stability | Water absorption properties (cm) |
|---|---|---|---|---|---|---|---|---|---|---|---|
| Ex. 3-24 | 3-A-15 (5) | 3-B-1 (20) | — | — | 3-E-2 (3) | 3-F-4 (1.5) | surfactant (3-X) (2) | +2 | +2 | good | 12.4 |
| 3-25 | 3-A-15 (5) | 3-B-1 (20) | — | — | 3-E-2 (3) | 3-F-5 (1.5) | surfactant (3-X) (2) | +2 | +2 | good | 12.9 |
| 3-26 | 3-A-5 (4) | 3-B-1 (16) | — | 3-D-2 (2) | 3-E-2 (3) | — | — | +2 | +2 | good | 13.5 |
| 3-27 | 3-A-5 (4) | 3-B-1 (16) | — | 3-D-5 (2) | 3-E-2 (3) | — | — | +2 | +2 | good | 13.4 |

TABLE 3-10-continued

|   | Component (3-A) | Component (3-B) | Component (3-C) | Component (3-D) | Component (3-E) | Component (3-F) | Other component | Softness | Elasticity | Storage stability | Water absorption properties (cm) |
|---|---|---|---|---|---|---|---|---|---|---|---|
| 3-28 | 3-A-5 (4) | 3-B-2 (16) | — | 3-D-6 (2) | 3-E-1 (3) | — | surfactant (3-X) (2) | +2 | +2 | good | 13.2 |
| 3-29 | 3-A-10 (4) | 3-B-1 (16) | — | 3-D-7 (2) | 3-E-1 (3) | — | surfactant (3-X) (2) | +2 | +2 | good | 14.0 |
| 3-30 | 3-A-10 (4) | 3-B-1 (16) | — | 3-D-11 (2) | 3-E-2 (3) | — | — | +2 | +2 | good | 13.2 |
| 3-31 | 3-A-10 (4) | 3-B-2 (16) | — | 3-D-1 (2) | 3-E-2 (3) | — | — | +2 | +2 | good | 13.5 |
| 3-32 | 3-A-15 (4) | 3-B-1 (16) | — | 3-D-3 (2) | 3-E-2 (3) | — | surfactant (3-X) (2) | +2 | +2 | good | 12.4 |
| 3-33 | 3-A-15 (4) | 3-B-1 (16) | — | 3-D-4 (2) | 3-E-1 (3) | — | surfactant (3-X) (2) | +2 | +2 | good | 13.2 |
| 3-34 | 3-A-15 (4) | 3-B-1 (16) | — | 3-D-12 (2) | 3-E-2 (3) | — | — | +2 | +2 | good | 12.9 |

TABLE 3-11

|   |   | Component (3-A) | Component (3-B) | Component (3-C) | Component (3-D) | Component (3-E) | Component (3-F) | Other component | Softness | Elasticity | Storage stability | Water absorption properties (cm) |
|---|---|---|---|---|---|---|---|---|---|---|---|---|
| Ex. | 3-35 | 3-A-15 (4) | 3-B-2 (16) | — | 3-D-9 (2) | 3-E-2 (3) | — | — | +2 | +2 | good | 12.4 |
|  | 3-36 | 3-A-15 (4) | 3-B-1 (16) | — | 3-D-8 (2) | 3-E-2 (3) | — | — | +2 | +2 | good | 13.4 |
|  | 3-37 | 3-A-7 (4) | 3-B-1 (16) | — | 3-D-10 (2) | 3-E-2 (3) | — | surfactant (3-X) (2) | +2 | +2 | good | 13.7 |
|  | 3-38 | 3-A-5 (4) | 3-B-1 (16) | — | — | 3-E-2 (3) | 3-F-2 (1) | surfactant (3-X) (1) surfactant (3-Y) (1) | +2 | +2 | good | 13.5 |
|  | 3-39 | 3-A-10 (4) | 3-B-1 (16) | — | — | 3-E-2 (3) | 3-F-4 (1) | surfactant (3-X) (1) surfactant (3-Y) (1) | +2 | +2 | good | 13.6 |
|  | 3-40 | 3-A-9 (4) | 3-B-1 (16) | — | — | 3-E-2 (3) | 3-F-3 (1) | surfactant (3-X) (2) | +2 | +2 | good | 12.5 |
|  | 3-41 | 3-A-15 (4) | 3-B-1 (16) | — | — | 3-E-2 (3) | 3-F-5 (1) | surfactant (3-X) (2) | +2 | +2 | good | 12.3 |

TABLE 3-12

|   |   | Component (3-A) | Component (3-B) | Component (3-C) | Component (3-D) | Component (3-E) | Component (3-F) | Other component | Softness | Elasticity | Storage stability | Water absorption properties (cm) |
|---|---|---|---|---|---|---|---|---|---|---|---|---|
| Comp. Ex. | 3-1 | 3-A-4 (5) | — | — | — | 3-E-2 (3) | — | surfactant (3-X) (2) | −2 | −2 | good | 12.6 |
|  | 3-2 | 3-A-5 (4) | — | — | — | 3-E-2 (3) | — | surfactant (3-X) (2) | −1 | −2 | good | 11.0 |
|  | 3-3 | 3-A-10 (4) | — | — | — | 3-E-2 (3) | — | — | −2 | −2 | good | 11.3 |
|  | 3-4 | 3-A-9 (4) | — | — | — | 3-E-2 (3) | — | — | −2 | −2 | good | 12.6 |
|  | 3-5 | 3-A-15 (4) | — | — | 3-D-6 (2) | 3-E-1 (3) | — | surfactant (3-X) (2) | −1 | −2 | good | 11.5 |
|  | 3-6 | 3-A-5 (4) | — | — | 3-D-7 (2) | 3-E-1 (3) | 3-F-2 (1) | surfactant (3-X) (2) | −2 | −2 | good | 12.5 |
|  | 3-7 | 3-A-15 (4) | — | — | 3-D-11 (2) | 3-E-2 (3) | 3-F-4 (1) | — | −2 | −2 | good | 11.0 |
|  | 3-8 | 3-A-15 (4) | — | 3-C-1 (2) | 3-D-1 (2) | 3-E-2 (3) | 3-F-1 (1) | — | −2 | −2 | good | 12.0 |
|  | 3-9 | 3-A-10 (4) | — | 3-C-3 (2) | 3-D-5 (2) | 3-E-2 (3) | 3-F-3 (1) | surfactant (3-X) (2) | −2 | −2 | good | 12.4 |

TABLE 3-13

| | | Component (A) | Component (B) | Component (C) | Component (D) | Component (E) | Component (F) | Other component | Softness | Elasticity | Storage stability | Water absorption properties (cm) |
|---|---|---|---|---|---|---|---|---|---|---|---|---|
| Comp. Ex. | 3-10 | 3-A-15 (4) | — | — | 3-D-6 (2) | 3-E-2 (3) | — | compd. (3-S) (16) | 0 | 0 | gelation | 6.8 |
| | 3-11 | 3-A-15 (4) | — | — | — | 3-E-2 (3) | — | compd. (3-S) (16) | 0 | 0 | good | 6.7 |
| | 3-12 | — | — | — | — | 3-E-2 (3) | — | compd. (3-T) (16) | 0 | 0 | gelation | 7.3 |
| | 3-13 | 3-A-4 (5) | — | — | — | 3-E-2 (3) | — | compd. (3-T) (16) | 0 | 0 | gelation | 6.8 |
| | 3-14 | — | — | — | — | 3-E-2 (3) | — | compd. (3-U) (16) | 0 | 0 | gelation | 9.3 |
| | 3-15 | 3-A-9 (4) | — | — | — | 3-E-2 (3) | — | compd. (3-U) (16) | 0 | 0 | gelation | 9.2 |
| | 3-16 | — | — | — | — | 3-E-2 (3) | — | compd. (3-S) (16) | 0 | 0 | good | 6.2 | note) In Tables 3–8 to 3–13, the figures in parentheses each represent the content (wt %) of each component in the composition, and the balance is composed of water. The compositions were adjusted to pH3.

It can be understood from the above results that the softener compositions according to the present invention can impart excellent softness, elasticity and water absorption properties and are excellent in storage stability.

Examples 4-1 to 4-23 and Comparative Examples 4-1 to 4-11

Liquid softener compositions were prepared by the use of components (4-A) listed in Table 4-1, components (4-B) listed in Table 4-2, components (4-C) listed in Table 4-3, components (4-D) listed in Table 4-4, components (4-E) listed in Table 4-5, components (4-F) listed in Table 4-6 and other components listed in Table 4-7 according to the formulations specified in Tables 4-8 and 4-10.

TABLE 4-1

| | Component (4-A) | |
|---|---|---|
| | $R^0$ group in the formula (4-I) | No. of alkylene oxide molecules added to diethanolamide |
| 4-A-1 | alkyl group from hardened tallow fatty acid | 0 |
| 4-A-2 | alkyl group from semihardened tallow fatty acid [1:1 (by wt.) mixture of hardened tallow with tallow] | 0 |
| 4-A-3 | alkyl group from palm stearic acid | 0 |
| 4-A-4 | alkyl group from hardened palm stearic acid | ethylene oxide 2 |
| 4-A-5 | alkyl group from coconut oil fatty acid | 0 |
| 4-A-6 | alkyl group from palm kernel oil fatty acid | 0 |
| 4-A-7 | alkyl group from lauric acid | propylene oxide 1 |

TABLE 4-2

Component (4-B)

4-B-1  $CH_3\diagdown\!\!\!\!\!\!\!\!\!\!\!{}^+\!\!\!\!\!\!\!\!\!\!\!\!\!\!\!\!\diagup\!\!\!\!\!\!\!\!\!\!\!\!\!\!\!\!\!\!\!\!\!\!\!CH_3\text{—N—}CH_2COOCH_2CH(CH_2)_{17}CH_3 \cdot Cl^-$
$CH_3 \qquad \qquad \quad (CH_2)_{15}CH_3$ 4-B-2  $CH_3\diagdown\!\!\!\!\!\!\!\!\!\!\!{}^+\!\!\!\!\!\!\!\!\!\!\!\!\!\!\!\!\diagup\!\!\!\!\!\!\!\!\!\!\!\!\!\!\!\!\!\!\!\!\!\!\!CH_3\text{—N—}CH_2CH_2CH_2COOCH_2CH(CH_2)_{17}CH_3 \cdot Cl^-$
$CH_3 \qquad \qquad \quad (CH_2)_{15}CH_3$ 4-B-3  $CH_3\diagdown\!\!\!\!\!\!\!\!\!\!\!{}^+\!\!\!\!\!\!\!\!\!\!\!\!\!\!\!\!\diagup\!\!\!\!\!\!\!\!\!\!\!\!\!\!\!\!\!\!\!\!\!\!\!CH_3\text{—N—}(CH_2)_5COOCH_2CH(CH_2)_{17}CH_3 \cdot Cl^-$
$CH_3 \qquad \qquad \quad (CH_2)_{15}CH_3$ 4-B-4  $CH_3\diagdown\!\!\!\!\!\!\!\!\!\!\!{}^+\!\!\!\!\!\!\!\!\!\!\!\!\!\!\!\!\diagup\!\!\!\!\!\!\!\!\!\!\!\!\!\!\!\!\!\!\!\!\!\!\!CH_3\text{—N—}CH_2COOCH_2CH(CH_2)_{13}CH_3 \cdot Cl^-$
$CH_3 \qquad \qquad \quad (CH_2)_{11}CH_3$ 4-B-5  $CH_3\diagdown\!\!\!\!\!\!\!\!\!\!\!{}^+\!\!\!\!\!\!\!\!\!\!\!\!\!\!\!\!\diagup\!\!\!\!\!\!\!\!\!\!\!\!\!\!\!\!\!\!\!\!\!\!\!CH_3\text{—N—}CH_2COOCH_2CH(CH_2)_9CH_3 \cdot Cl^-$
$CH_3 \qquad \qquad \quad (CH_2)_7CH_3$

TABLE 4-3

| | Component (4-C) |
|---|---|
| 4-C-1 | $HO\text{—}CH_2\text{—}CH\text{—}(CH_2)_{17}CH_3$ <br> $\qquad\qquad\quad\; \vert$ <br> $\qquad\qquad\quad (CH_2)_{15}CH_3$ |
| 4-C-2 | $HO\text{—}CH_2\text{—}CH\text{—}(CH_2)_{13}CH_3$ <br> $\qquad\qquad\quad\; \vert$ <br> $\qquad\qquad\quad (CH_2)_{11}CH_3$ |
| 4-C-3 | $HO\text{—}CH_2\text{—}CH\text{—}(CH_2)_{11}CH_3$ <br> $\qquad\qquad\quad\; \vert$ <br> $\qquad\qquad\quad (CH_2)_9CH_3$ |
| 4-C-4 | $HO\text{—}CH_2\text{—}CH\text{—}(CH_2)_9CH_3$ <br> $\qquad\qquad\quad\; \vert$ <br> $\qquad\qquad\quad (CH_2)_7CH_3$ |

TABLE 4-4

| | Component (4-D) |
|---|---|
| 4-D-1 | tallow fatty acid |
| 4-D-2 | palm stearic acid |
| 4-D-3 | oleic acid |

TABLE 4-5

| | Component (4-E) |
|---|---|
| 4-E-1 | isopropanol |

TABLE 4-6

| | Component (4-F) | |
|---|---|---|
| 4-F-1 | adduct of glycerol with EO | (MW 8,900) |
| 4-F-2 | adduct of glycerol with PO/EO (15:85) | (MW 10,000) |
| 4-F-3 | adduct of sorbitol with PO/EO (10:90) | (MW 15,000) |
| 4-F-4 | adduct of tetraethylenepentamine with PO/EO (2:98) | (MW 20,000) |
| 4-F-5 | adduct of polyethyleneimine (MW: 3,000) with PO/EO (5:95) | (MW 300,000) |

TABLE 4-7

Other component

4-G-1*[1]

$$\text{CH}_3 \diagdown \overset{+}{\underset{\diagdown}{N}} \diagup \text{R}^{23} \quad \text{Cl}^-$$
$$\text{CH}_3 \diagup \phantom{N} \diagdown \text{R}^{33}$$

4-G-2*[2]

$$\text{CH}_3 \diagdown \overset{+}{\underset{\diagdown}{N}} \diagup \text{C}_2\text{H}_4\text{OCOR}^{24} \quad \text{Cl}^-$$
$$\text{CH}_3 \diagup \phantom{N} \diagdown \text{C}_2\text{H}_4\text{OCOR}^{34}$$

4-G-3*[2]

$$\begin{array}{c} \text{CH}_3 \\ | \\ \text{CH}_3 - \text{N}^+ - \text{CH}_2\text{CHCH}_2\text{OCOR}^{24} \\ | \phantom{----} | \\ \text{CH}_3 \phantom{---} \text{OCOR}^{34} \end{array} \text{Cl}^-$$

| 4-G-4 | polyoxyethylene (P = 20) lauryl ether |
| 4-G-5*[3] | adduct of hardened tallow fatty acid diethanolamide with 8 EO molecules |
| 4-G-6 | tallow fatty acid monoethanolamide |
| 4-G-7*[4] | quaternization product of partially hardened tallow fatty acid ester of triethanolamine | notes)
*[1] $R^{23}$ and $R^{33}$ represent alkyl group obtained by replacing the carboxyl group of hardened tallow fatty acid by methyl group.
*[2] $R^{24}$ and $R^{34}$ represent alkyl group obtained by freeing hardened tallow fatty acid from carboxyl group.
*[3] EO represents ethylene oxide.
*[4] a mixture comprising 20% by weight of a compound represented by the following formula (4-G-7-1), 45% by weight of one represented by the following formula (4-G-7-2) and 35% by weight of one represented by the following formula (G-7-3):

$$\text{CH}_3 \diagdown \overset{+}{\underset{\diagdown}{N}} \diagup \text{CH}_2\text{CH}_2\text{OH} \quad \text{CH}_3\text{SO}_4^- \quad (4\text{-G-7-1})$$
$$\text{HOCH}_2\text{CH}_2 \diagup \phantom{N} \diagdown \text{CH}_2\text{CH}_2\text{OCOR}^{31}$$

TABLE 4-7-continued

Other component $$\text{CH}_3 \diagdown \overset{+}{\underset{\diagdown}{N}} \diagup \text{CH}_2\text{CH}_2\text{OCOR}^{31} \quad \text{CH}_3\text{SO}_4^- \quad (4\text{-G-7-2})$$
$$\text{HOCH}_2\text{CH}_2 \diagup \phantom{N} \diagdown \text{CH}_2\text{CH}_2\text{OCOR}^{31}$$

$$\text{CH}_3 \diagdown \overset{+}{\underset{\diagdown}{N}} \diagup \text{CH}_2\text{CH}_2\text{OCOR}^{31} \quad \text{CH}_3\text{SO}_4^- \quad (4\text{-G-7-3})$$
$$\text{R}^{31}\text{COOCH}_2\text{CH}_2 \diagup \phantom{N} \diagdown \text{CH}_2\text{CH}_2\text{OCOR}^{31}$$

(wherein $R^{31}$ represents a mixed group comprising alkyl group resulting from hardened tallow fatty acid and alkyl group resulting from unhardened tallow fatty acid at a weight ratio of 25:75)

The storage stability of the liquid softener compositions prepared in Examples 4-1 to 4-23 and Comparative Examples 4-1 to 4-11 and the softness, elasticity and water absorption properties of textiles treated with the compositions were evaluated by the following methods. The results are given in Tables 4-8 to 4-10.

[Evaluation of softness and elasticity]

Commercially available towel and pieces of acrylic textile and polyester textile were washed five times with a commercially available detergent "Attack" (a product of Kao Corporation, registered trademark) and thereafter freed from the detergent attaching to them. A liquid softener composition prepared above was thrown into a tub in an amount of 0.5% based on the total weight of the cloths to be treated. The above cloths were treated in the resulting bath at 25° C. and a bath ratio of 1/30 under agitation for 3 minutes, dried with air in a room and allowed to stand in an air conditioned room of 20° C. and 65% RH for 24 hours.

The resulting cloths were evaluated for softness and elasticity.

This evaluation was conducted by comparing the cloths with those treated with the softener composition of Comparative Example 4-1 as control according to the following criteria:

softness:
 +2: softer or more elastic than the control
 +1: somewhat softer or somewhat more elastic than the control
 0: equivalent to the control in softness or elasticity
 −1: the control is somewhat softer or somewhat more elastic
 −2: the control is softer or more elastic <Evaluation process of storage stability>

The liquid softener compositions prepared above were each stored in a hermetically sealed state at 20° C. and 40° C. for 20 days and examined for appearance and fluidity with the eye. The case wherein no change was observed in the appearance or fluidity is shown by "good", while the case wherein a change was observed is shown by the kind of the change.

<Evaluation method of water absorption properties [Byreck's method]>

The cloths treated in the same treatment manner as that employed in the evaluation of softness and elasticity were allowed to stand in an air conditioned room of 25° C. and 65% RH for 24 hours. Among the resulting cloths, the cotton towel was evaluated for water absorption properties.

The non-piled area of the towel was cut into a rectangular piece (25 cm×2 cm). Water of 25° C. was provided to the air conditioned room. The piece was soaked in the water up to 2 cm from its lower end in a vertically hung state to make it absorb water. After 15 minutes, the ascent (height) of water was determined.

TABLE 4-8

| | | Component (4-A) | Component (4-B) | Component (4-C) | Component (4-D) | Component (4-E) | Component (4-F) | Other component | Softness | Elasticity | Storage stability 40° C. | Storage stability 20° C. | Water absorption properties (cm) |
|---|---|---|---|---|---|---|---|---|---|---|---|---|---|
| Ex. | 4-1 | 4-A-1 (4) | 4-B-1 (16) | — | — | 4-E-1 (3) | — | 4-C-4 (2) | +2 | +2 | good | good | 12.4 |
| | 4-2 | 4-A-2 (4) | 4-B-1 (16) | — | 4-D-1 (1) | 4-E-1 (3) | — | — | +2 | +2 | good | good | 14.0 |
| | 4-3 | 4-A-3 (4) | 4-B-1 (16) | — | — | 4-E-1 (3) | — | — | +2 | +2 | good | good | 13.5 |
| | 4-4 | 4-A-4 (4) | 4-B-1 (16) | — | — | 4-E-1 (3) | — | 4-G-4 (2) | +2 | +2 | good | good | 12.4 |
| | 4-5 | 4-A-5 (4) | 4-B-1 (16) | — | 4-D-3 (1) | 4-E-1 (3) | — | — | +2 | +2 | good | good | 13.0 |
| | 4-6 | 4-A-6 (4) | 4-B-1 (16) | — | — | 4-E-1 (3) | — | 4-G-4 (2) | +2 | +2 | good | good | 12.6 |
| | 4-7 | 4-A-7 (4) | 4-B-1 (16) | — | — | 4-E-1 (3) | — | 4-G-4 (2) | +2 | +2 | good | good | 13.1 |
| | 4-8 | 4-A-1 (4) | 4-B-1 (16) | 4-C-1 (2) | — | 4-E-1 (3) | — | 4-G-4 (2) | +2 | +2 | good | good | 12.5 |
| | 4-9 | 4-A-2 (4) | 4-B-2 (16) | 4-C-1 (2) | 4-D-2 (1) | 4-E-1 (3) | — | 4-G-4 (2) | +2 | +2 | good | good | 13.5 |
| | 4-10 | 4-A-3 (4) | 4-B-3 (16) | 4-C-3 (2) | 4-D-3 (1) | 4-E-1 (3) | — | 4-G-4 (2) | +2 | +2 | good | good | 14.0 |
| | 4-11 | 4-A-7 (4) | 4-B-4 (16) | 4-C-2 (2) | — | 4-E-1 (3) | — | 4-G-4 (2) | +1 | +2 | good | good | 12.6 |
| | 4-12 | 4-A-5 (4) | 4-B-5 (16) | 4-C-4 (2) | — | 4-E-1 (3) | — | 4-G-4 (2) | +1 | +2 | good | good | 12.8 |

TABLE 4-9

| | | Component (4-A) | Component (4-B) | Component (4-C) | Component (4-D) | Component (4-E) | Component (4-F) | Other component | Softness | Elasticity | Storage stability 40° C. | Storage stability 20° C. | Water absorption properties (cm) |
|---|---|---|---|---|---|---|---|---|---|---|---|---|---|
| Ex. | 4-13 | 4-A-2 (4) | 4-B-1 (16) | — | — | 4-E-1 (3) | 4-F-1 (1) | — | +2 | +2 | good | good | 12.6 |
| | 4-14 | 4-A-3 (4) | 4-B-2 (16) | — | 4-D-2 (1) | 4-E-1 (3) | 4-F-2 (1) | — | +2 | +2 | good | good | 13.4 |
| | 4-15 | 4-A-4 (4) | 4-B-3 (16) | — | — | 4-E-1 (3) | 4-F-4 (1) | — | +2 | +2 | good | good | 13.2 |
| | 4-16 | 4-A-5 (4) | 4-B-1 (16) | — | — | 4-E-1 (3) | 4-F-3 (1) | 4-G-4 (2) | +2 | +2 | good | good | 14.1 |
| | 4-17 | 4-A-1 (4) | 4-B-1 (16) | 4-C-1 (2) | 4-D-1 (1) | 4-E-1 (3) | 4-F-2 (1) | 4-G-4 (2) | +2 | +2 | good | good | 13.6 |
| | 4-18 | 4-A-3 (4) | 4-B-1 (16) | 4-C-1 (2) | — | 4-E-1 (3) | 4-F-4 (1) | 4-G-4 (2) | +2 | +2 | good | good | 12.6 |
| | 4-19 | 4-A-5 (4) | 4-B-4 (16) | — | — | 4-E-1 (3) | 4-F-5 (1) | 4-G-4 (2) | +2 | +2 | good | good | 13.5 |
| | 4-20 | 4-A-5 (4) | 4-B-5 (16) | — | — | 4-E-1 (3) | 4-F-4 (1) | 4-G-4 (2) | +2 | +2 | good | good | 13.1 |
| | 4-21 | 4-A-1 (5) | 4-B-1 (20) | — | — | 4-E-1 (3) | 4-F-4 (1) | 4-G-4 (2) | +2 | +2 | good | good | 12.4 |
| | 4-22 | 4-A-3 (5) | 4-B-1 (20) | — | — | 4-E-1 (3) | 4-F-5 (1) | 4-G-4 (2) | +2 | +2 | good | good | 11.6 |
| | 4-23 | 4-A-4 (5) | 4-B-1 (20) | — | — | 4-E-1 (3) | 4-F-1 (1) | 4-G-4 (2) | +2 | +2 | good | good | 11.8 |

TABLE 4-10

| | | Component (4-A) | Component (4-B) | Component (4-C) | Component (4-D) | Component (4-E) | Component (4-F) | Other component | Softness | Elasticity | Storage stability 40° C. | Storage stability 20° C. | Water absorption properties (cm) |
|---|---|---|---|---|---|---|---|---|---|---|---|---|---|
| Comp. Ex. | 4-1 | 4-A-4 (5) | — | — | — | — | — | 4-G-1 (16) 4-G-4 (2) | 0 | 0 | gelation | good | 6.7 |
| | 4-2 | 4-A-5 (4) | — | — | 4-D-1 (1) | — | 4-F-4 (1) | 4-G-1 (16) | −1 | −1 | gelation | separation | 6.2 |

TABLE 4-10-continued

| | Component (4-A) | Component (4-B) | Component (4-C) | Component (4-D) | Component (4-E) | Component (4-F) | Other component | Soft-ness | Elas-ticity | Storage stability 40° C. | Storage stability 20° C. | Water absorption properties (cm) |
|---|---|---|---|---|---|---|---|---|---|---|---|---|
| 4-3 | 4-A-2 (4) | — | — | 4-D-2 (1) | 4-E-1 (3) | — | 4-G-2 (16) | 0 | −2 | separation | good | 8.2 |
| 4-4 | 4-A-6 (4) | — | 4-C-1 (2) | — | 4-E-1 (3) | 4-F-2 (1) | 4-G-2 (16) 4-G-4 (2) | −1 | −2 | separation | good | 7.3 |
| 4-5 | 4-A-1 (4) | — | — | — | 4-E-1 (3) | 4-F-3 (1) | 4-G-3 (16) 4-G-4 (2) | −1 | −2 | gelation | gelation | 10.5 |
| 4-6 | 4-A-5 (4) | — | — | — | 4-E-1 (3) | — | 4-G-3 (16) 4-G-4 (2) | −2 | −2 | gelation | gelation | 9.3 |
| 4-7 | — | 4-B-1 (16) | — | — | 4-E-1 (3) | — | 4-G-4 (2) 4-G-5 (4) | 0 | 0 | gelation | gelation | 7.3 |
| 4-8 | — | 4-B-1 (16) | — | — | 4-E-1 (3) | — | 4-G-4 (2) 4-G-6 (4) | 0 | 0 | separation | gelation | 6.8 |
| 4-9 | — | 4-B-4 (16) | — | 4-D-2 (3) | 4-E-1 (3) | — | 4-G-6 (4) | −1 | 0 | separation | gelation | 7.6 |
| 4-10 | — | 4-B-5 (16) | — | — | — | — | 4-G-5 (4) | −1 | 0 | gelation | gelation | 8.5 |
| 4-11 | 4-A-1 (4) | — | — | — | — | — | 4-G-7 (16) | −2 | −1 | gelation | gelation | 10.2 | note) In Tables 4-8 to 4-10, the figures in parentheses each represent the content (wt %) of each component in the composition, and the balance is composed of water. The compositions were adjusted to pH3.

It can be understood from the above results that the softener compositions according to the present invention can impart excellent softness, elasticity and water absorption properties and are excellent in storage stability.

Synthesis Example 5-1

Tallow (85.9 g), glycerol (9.2 g) and 85% potassium hydroxide (0.40 g) were charged into an autoclave fitted with a stirrer and a thermometer. The contents were kept at 110° C. and 200 Torr for one hour to conduct dehydration. Thereafter, the system was hermetically sealed. The contents were heated to 1600° C. and reacted for 3 hours. Ethylene oxide (105.6 g) was added into the autoclave in 2 hours. The resulting mixture was aged for one hour and cooled. The catalyst was neutralized by the addition of 0.36 g of acetic acid. Thus, a product of reaction of tallow with glycerol and ethylene oxide was obtained.

Synthesis Examples 5-2 to 5-6

The same procedure as that of Example 5-1 was repeated except for the conditions specified in Table 5-1 to give products of natural fats or oil, grycerol and alkylene oxide.

TABLE 5-1

| | Synth. Ex. | | | | | |
|---|---|---|---|---|---|---|
| | 5-1 | 5-2 | 5-3 | 5-4 | 5-5 | 5-6 |
| Fat or oil | tallow 85.9 g | tallow 85.9 g | tallow 85.9 g | palm oil 82.9 g | palm kernel oil 67.7 g | coconut oil 65.2 g |
| Glycerol | 9.2 g | 41.9 g | 4.6 g | 1.8 g | 18.4 g | 27.6 g |
| 85% KOH | 0.4 g | 0.4 g | 0.4 g | 0.4 g | 0.4 g | 0.4 g |
| Alkylene oxide | EO 105.6 g | EO 240.2 g | EO 44.0 g  PO 46.4 g | EO 10.6 g | EO 154.0 g | PO 290.0 g |
| Reaction temp. | 160° C. | 160° C. | 160° C. | 160° C. | 160° C. | 160° C. | note)
Alkylene oxide: EO represents ethylene oxide and PO propylene oxide
In Synth. Ex. 3, ethylene oxide and propylene oxide were added simultaneously.

Example 5-1

The reaction product (35 g) obtained in Synthesis Example 1, 2-hexadecyleicosyl dimethylaminoacetic acid (130 g) and chloromethane (13 g) were charged into an autoclave fitted with a stirrer and a thermometer. The contents were heated to 90° C. and reacted at that temperature for 6 hours to form a corresponding quaternary ammonium salt.

Examples 5-2 to 5-4

The same procedure as that of Example 5-1 was repeated except for the conditions specified in Table 5-2 to form a corresponding quaternary ammonium salt.

Comparative Examples 5-1 to 5-4

The same procedures as those of Examples 5-1 to 5-4 were repeated except that the reaction products of Synthesis Examples 5-1 to 5-3 were replaced by the same amount of isopropyl alcohol. Thus, quaternary ammonium salts were formed.

In Table 5-2 are given the reaction conditions of Examples 5-1 to 5-4 and Comparative Examples 5-1 to 5-4, the structures of quaternary ammonium salts formed therein, and the results of evaluation of the salts for softening effect and smell.

The quaternary ammonium salts were evaluated for softening effect and smell according to the following method.
<Evaluation method of softening effect and smell>
(1) Preparation of dispersions of quaternary ammonium salts The reaction mixtures of the above Examples and Comparative Examples containing quaternary ammonium salts were each molten and dropped into water under agitation to form dispersions having a quaternary ammonium salt content of 5%.
(2) Method of treatment Commercially available cotton towel (2 kg) was washed five times with hard water of 3.5° D and a commercially available detergent "Attack" (a product of Kao Corporation, registered trademark) by the use of a 30 l washing machine. 25 ml of a dispersion prepared above was thrown into the washing machine tub and the cotton towel washed above was treated in the resulting bath at 25° C. under agitation for one minute.

(3) Evaluation method of softening effect

The cotton towels treated by the above method were dried with air at room temperature and allowed to stand in an air conditioned room of 25° C. and 65% RH for 24 hours. The resulting towels were evaluated for softness. This evaluation was conducted by comparing the towels with that (as control) treated with dimethyldi(hardened tallow alkyl) ammonium chloride which is a conventional softener according to the following criteria:

4: considerably softer than the control

3: softer than the control

2: softer or somewhat softer than the control

1: somewhat softer than the control

0: equivalent to the control in softness (4) Evaluation method of smell

The 5% dispersions prepared above were evaluated for smell by smelling according to the following criteria:

x: foreign odor o: no foreign odor

TABLE 5-2

| | Ex. 5-1 | Comp. Ex. 5-1 | Ex. 5-2 | Comp. Ex. 5-2 | Ex. 5-3 | Comp. Ex. 5-3 | Ex. 5-4 | Comp. Ex. 5-4 |
|---|---|---|---|---|---|---|---|---|
| Tertiary amine compound | $H_3C$—N—$CH_2COOCH_2CHC_{18}H_{37}$ / $H_3C$ / $C_{16}H_{33}$ 130 g | $H_3C$—N—$CH_2COOCH_2CHC_{18}H_{37}$ / $H_3C$ / $C_{16}H_{33}$ | $H_3C$—N—$CH_2COOCH_2CHC_{18}H_{37}$ / $H_3C$ / $C_{16}H_{33}$ 130 g | $H_3C$—N—$CH_2COOCH_2CHC_{18}H_{37}$ / $H_3C$ / $C_{16}H_{33}$ | $H_3C$—N—$CH_3$ / $H_3C$ 17 g | $H_3C$—N—$CH_3$ / $H_3C$ | $H_3C$—N—$C_2H_4OH$ / $H_3C$ 26 g | $H_3C$—N—$C_2H_4OH$ / $H_3C$ |
| Polyhydric alc. ester | reaction product of Synth. Ex. 5-1 35 g | none | reaction product of Synth. Ex. 5-2 50 g | none | reaction product of Synth. Ex. 5-1 30 g | none | reaction product of Synth. Ex. 5-3 40 g | none |
| Quaternizing agent | $CH_3Cl$ 13 g | | $(CH_3)_2SO_4$ 33 g | | $ClCH_2COOCH_2CHC_{14}H_{29}$ / $C_{12}H_{25}$ 125 g | $ClCH_2COOCH_2CHC_{14}H_{29}$ / $C_{12}H_{25}$ 125 g | $ClCH_2COOCH_2CHC_{18}H_{37}$ / $C_{16}H_{33}$ 150 g | $ClCH_2COOCH_2CHC_{18}H_{37}$ / $C_{16}H_{33}$ 150 g |
| Reaction temp. (°C.) | 90 | | 70 | | 60 | 60 | 60 | 60 |
| Reaction time (hr) | 6 | | 5 | | 3 | 3 | 3 | 3 |
| Quaternary ammonium salt formed | $H_3C$—N$^+$—$CH_2COOCH_2CHC_{18}H_{37}$ / $H_3C$ / $H_3C$ / $C_{16}H_{33}$ $Cl^-$ | $H_3C$—N—$CH_2COOCH_2CHC_{18}H_{37}$ / $H_3C$ / $C_{16}H_{33}$ | $H_3C$—N$^+$—$CH_2COOCH_2CHC_{18}H_{37}$ / $H_3C$ / $H_3C$ / $C_{16}H_{33}$ $CH_3SO_4^-$ | $H_3C$—N—$CH_2COOCH_2CHC_{18}H_{37}$ / $H_3C$ / $C_{16}H_{33}$ | $H_3C$—N$^+$—$CH_2COOCH_2CHC_{14}H_{29}$ / $H_3C$ / $H_3C$ / $C_{12}H_{25}$ $Cl^-$ | $H_3C$—N—$CH_2COOCH_2CHC_{14}H_{29}$ / $H_3C$ / $C_{12}H_{25}$ | $HOC_2H_4$—N$^+$—$CH_2COOCH_2CHC_{18}H_{37}$ / $H_3C$ / $H_3C$ / $C_{16}H_{33}$ $Cl^-$ | $H_3C$—N—$CH_2COOCH_2CHC_{18}H_{37}$ / $H_3C$ / $C_{16}H_{33}$ |
| Softness | 4 | 2 | 4 | 2 | 2 | 0 | 3 | 1 |
| Smell | ○ | x | ○ | x | ○ | x | ○ | x |

As apparent from the results given in Table 5-2, the reaction mixtures of Examples are superior to those of Comparative Examples in both softening effect and smell.

Examples 5-5 to 5-7

Quaternary ammonium salts were prepared in the same manner as that of Example 5-1 under the conditions specified in Table 5-3.

In Table 5-3 are given the reaction conditions of Examples 5-5 to 5-7, the structures of quaternary ammonium salts formed therein, and the results of evaluation of the salts for softening effect and smell.

TABLE 5-3

| | Ex. 5-5 | Ex. 5-6 | Ex. 5-7 |
|---|---|---|---|
| Tertiary amine compound | $H_3C\!\!-\!\!N(CH_3)\!\!-\!\!CH_2COOCH_2CHC_{10}H_{21}$ with $C_8H_{17}$ branch<br>130 g | $(CH_3)_3N$<br>17 g | $(CH_3)_3N$<br>17 g |
| Polyhydric alc. ester | reaction product of Synth. Ex. 5-4<br>35 g | reaction product of Synth. Ex. 5-5<br>50 g | reaction product of Synth. Ex. 5-6<br>50 g |
| Quaternizing agent | $CH_3Cl$<br>13 g | $Cl(CH_2)_3COOCH_2CHC_{18}H_{37}$ with $C_{16}H_{33}$ branch<br>160 g | $Cl(CH_2)_5COOCH_2CHC_{18}H_{37}$ with $C_{16}H_{33}$ branch<br>165 g |
| Reaction temp. (°C.) | 90 | 60 | 60 |
| Reaction time (hr) | 6 | 3 | 3 |
| Quaternary ammonium salt formed | $[H_3C\!\!-\!\!N^+(CH_3)(H_3C)\!\!-\!\!CH_2COOCH_2CHC_{10}H_{21}]$ with $C_8H_{17}$ branch, $Cl^-$ | $[H_3C\!\!-\!\!N^+(CH_3)(H_3C)\!\!-\!\!(CH_2)_3COOCH_2CHC_{18}H_{37}]$ with $C_{16}H_{33}$ branch, $Cl^-$ | $[H_3C\!\!-\!\!N^+(CH_3)(H_3C)\!\!-\!\!(CH_2)_5COOCH_2CHC_{18}H_{37}]$ with $C_{16}H_{33}$ branch, $Cl^-$ |
| Softness | 1 | 3 | 3 |
| Smell | ○ | ○ | ○ |

Synthesis Example 6-1

Diethanolamine (172 g) and a 28% methanolic solution (5 g) of $NaOCH_3$ were put in a four-necked flask fitted with a stirrer and a thermometer. The contents were stirred under the conditions of 100° C. and 30 Torr for one hour to distill away the methanol. Purified palm stearin oil (417 g) was added to the residue. The obtained mixture was reacted under the conditions of 100° C. and 30 Torr for 2 hours. The resulting reaction mixture was cooled to 60° C. and aged for 50 hours to give diethanolamide resulting from palm stearin oil.

Synthesis Example 6-2

The diethanolamide (180 g) prepared in Synthesis Example 6-1 was charged into an autoclave and heated to 150° C. Ethylene oxide (66 g) was added into the autoclave in 2 hours. The resulting mixture was aged for one hour to give an adduct of diethanolamide resulting from palm stearin oil with 3 ethylene oxide molecules.

Synthesis Examples 6-3 to 6-6

Diethanolamides were prepared from the raw materials listed in Table 6-1 in the same manner as that of Synthesis Example 6-1 except for the conditions specified in Table 6-1.

TABLE 6-1

| | Synth. Ex. No. | | | | | |
|---|---|---|---|---|---|---|
| | 6-1 | 6-2 | 6-3 | 6-4 | 6-5 | 6-6 |
| Raw material | palm stearin oil<br>417 g | palm stearin oil<br>417 g | hardened palm stearin oil<br>418 g | hardened tallow<br>602 g | palm kernel oil<br>674 g | methyl laurate<br>642 g |
| Diethanolamine | 172 g | 172 g | 156 g | 77 g | 335 g | 330 g |

TABLE 6-1-continued

| | Synth. Ex. No. | | | | | |
|---|---|---|---|---|---|---|
| | 6-1 | 6-2 | 6-3 | 6-4 | 6-5 | 6-6 |
| 28% methanolic soln. of $NaOCH_3$ | 5 g | 5 g | 5 g | 6 g | 10 g | 10 g |
| Reaction temp. | 100° C. | 100° C. | 100° | 120° C. | 120° C. | 110° C. |
| Reaction pressure | 30 torr | 30 torr | 30 torr | 50 torr | 50 torr | 50 torr |
| Reaction time | 2 hr. | 2 hr. | 2 hr. | 2 hr. | 3 hr. | 3 hr. |
| Alkylene oxide | 0 | EO* 3 mol | 0 | 0 | 0 | 0 | note)
*EO represents ethylene oxide

Example 6-1

The reaction product (35 g) prepared in Synthesis Example 1, 2-hexadecyleicosyl dimethylaminoacetate (130 g) and chloromethane (13 g) were charged into an autoclave fitted with a stirrer and a thermometer. The contents were heated to 90° C. and reacted at that temperature for 6 hours to give a corresponding quaternary ammonium salt.

Examples 6-2 to 6-4

The same procedure as that of Example 6-1 was repeated except for the conditions specified in Table 6-2 to give corresponding quaternary ammonium salts.

Comparative Examples 6-1 to 6-4

The same procedures as those of Examples 6-1 to 6-4 were respectively repeated except that the reaction products of Synthesis Examples 6-1 to 6-3 were replaced by the same weight amount of isopropyl alcohol. Thus, reaction mixtures mainly comprising quaternary ammonium salts listed in Table 6-2 were obtained.

In Table 6-2 are given the reaction conditions or Examples 6-1 to 6-4 and Comparative Examples 6-1 to 6-4, the structures of quaternary ammonium salts formed therein and the results of evaluation of the reaction mixtures for softening effect and smell by the following methods.

<Evaluation method of softening effect and smell>

(1) Preparation of dispersions of quaternary ammonium salts

The reaction mixtures obtained in the Examples and Comparative Examples which each contained a quaternary ammonium salt as the main component were each molten and dropped into water under agitation to form dispersions having a quaternary ammonium salt content of 5% by weight.

(2) Method of treatment

Commercially available cotton towel (2 kg) was washed five times with hard water of 3.5° D and a commercially available detergent "Attack" (a product of Kao Corporation, registered trademark) by the use of a 30 l washing machine. 25 ml of a dispersion prepared above was thrown into the washing machine tub and the resulting cotton towel was treated in the resulting bath at 25° C. under agitation for one minute.

(3) Evaluation method of softening effect

The cotton towels treated by the above method were dried with air at room temperature and allowed to stand in an air conditioned room of 25° C. and 65% RH for 24 hours. The resulting towels were evaluated for softness. This evaluation was conducted by comparing the towels with that (as control) treated with dimethyldi(hardened tallow alkyl) ammonium chloride which is a conventional softener according to the following criteria:

3: considerably softer than the control

2: softer than the control

1: somewhat softer than the control

0: equivalent to the control in softness (4) Evaluation method of smell

The 5% by weight dispersions of quaternary ammonium salt prepared above were evaluated for smell by smelling according to the following criteria:

×: alcoholic stench

○: no alcoholic stench

TABLE 6-2

| | Ex. 6-1 | Comp. Ex. 6-1 | Ex. 6-2 | Comp. Ex. 6-2 | Ex. 6-3 | Comp. Ex. 6-3 | Ex. 6-4 | Comp. Ex. 6-4 |
|---|---|---|---|---|---|---|---|---|
| Tertiary amine compound | $H_3C$\\$N-CH_2COOCH_2CHC_{18}H_{37}$/$H_3C$ / $C_{16}H_{33}$ 130 g | $H_3C$\\$N-CH_2COOCH_2CHC_{18}H_{37}$/$H_3C$ / $C_{16}H_{33}$ 130 g | $H_3C$\\$N-CH_2COOCH_2CHC_{18}H_{37}$/$H_3C$ / $C_{16}H_{33}$ 130 g | $H_3C$\\$N-CH_2COOCH_2CHC_{18}H_{37}$/$H_3C$ / $C_{16}H_{33}$ 130 g | $H_3C$\\$N-CH_3$/$H_3C$ 17 g | $H_3C$\\$N-CH_3$/$H_3C$ 17 g | $H_3C$\\$N-C_2H_4OH$/$H_3C$ 26 g | $H_3C$\\$N-C_2H_4OH$/$H_3C$ 26 g |
| Compd. of the general formula (6-II) | reaction product of Synth. Ex. 6-1 35 g | none | reaction product of Synth. Ex. 6-2 50 g | none | reaction product of Synth. Ex. 6-1 30 g | none | reaction product of Synth. Ex. 6-3 40 g | none |
| isopropyl alc. | none | 35 g | none | 50 g | none | 30 g | none | 40 g |
| Quaternizing agent | $CH_3Cl$ 13 g | | $(CH_3)_2SO_4$ 33 g | | $ClCH_2COOCH_2CHC_{14}H_{29}$ / $C_{12}H_{25}$ 125 g | | $ClCH_2COOCH_2CHC_{18}H_{37}$ / $C_{16}H_{33}$ 150 g | |
| Reaction temp. (°C.) | 90 | | 70 | | 60 | | 60 | |
| Reaction time (hr) | 6 | | 5 | | 3 | | 3 | |
| Quaternary ammonium salts formed | $H_3C$\\$H_3C-\overset{+}{N}-CH_2COOCH_2CHC_{18}H_{37}$/$H_3C$ / $C_{16}H_{33}$ / $Cl^-$ | $H_3C$\\$H_3C-\overset{+}{N}-CH_2COOCH_2CHC_{18}H_{37}$/$H_3C$ / $C_{16}H_{33}$ | $H_3C$\\$H_3C-\overset{+}{N}-CH_2COOCH_2CHC_{18}H_{37}$/$H_3C$ / $C_{16}H_{33}$ / $CH_3SO_4^-$ | $H_3C$\\$H_3C-\overset{+}{N}-CH_2COOCH_2CHC_{18}H_{37}$/$H_3C$ / $C_{16}H_{33}$ | $H_3C$\\$H_3C-\overset{+}{N}-CH_2COOCH_2CHC_{14}H_{29}$/$H_3C$ / $C_{12}H_{25}$ / $Cl^-$ | $H_3C$\\$H_3C-\overset{+}{N}-CH_2COOCH_2CHC_{14}H_{29}$/$H_3C$ / $C_{12}H_{25}$ | $HOC_2H_4$\\$H_3C-\overset{+}{N}-CH_2COOCH_2CHC_{18}H_{37}$/$H_3C$ / $C_{16}H_{33}$ / $Cl^-$ | $HOC_2H_4$\\$H_3C-\overset{+}{N}-CH_2COOCH_2CHC_{18}H_{37}$/$H_3C$ / $C_{16}H_{33}$ |
| Softness | 3 | 2 | 3 | 2 | 2 | 0 | 2 | 1 |
| Smell | ○ | x | ○ | x | ○ | x | ○ | x |

As apparent from the results given in Table 6-2, the reaction mixtures of Examples are superior to those of Comparative Examples in both softening effect and smell.

Examples 6-5 to 6-7

The same procedure as that of Example 6-1 was repeated except for the conditions specified in Table 6-3 to give corresponding quaternary ammonium salts.

In Table 6-3 are given the reaction conditions of Examples 6-5 to 6-7, the structures of quaternary ammonium salts formed therein and the results of evaluation of the reaction mixtures for softening effect and smell by the same methods as those employed in Example 6-1.

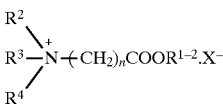

wherein $R^{1-2}$: linear or branched $C_{36}-C_{44}$ alkyl or alkenyl group; and $R^2$, $R^3$, $R^4$, n, $X^-$: each as defined above.

3. A quaternary ammonium salt as set forth in claim 1, which is represented by the formula (1-I-2):

TABLE 6-3

|  | Ex. 6-5 | Ex. 6-6 | Ex. 6-7 |
|---|---|---|---|
| Tertiary amine compound | H₃C\N—CH₂COOCH₂CHC₁₀H₂₁ / H₃C  C₈H₁₇<br>130 g | H₃C\N—CH₃ / H₃C<br>17 g | H₃C\N—CH₃ / H₃C<br>17 g |
| Compd. of the general formula (6-II) | reaction product of Synth. Ex. 6-4<br>35 g | reaction product of Synth. Ex. 6-5<br>50 g | reaction product of Synth. Ex. 6-6<br>50 g |
| Quaternizing agent | CH₃Cl<br>13 g | Cl(CH₂)₃COOCH₂CHC₁₈H₃₇ \| C₁₆H₃₃<br>160 g | Cl(CH₂)₅COOCH₂CHC₁₈H₃₇ \| C₁₆H₃₃<br>165 g |
| Reaction temp. (°C.) | 90 | 60 | 60 |
| Reaction time (hr) | 6 | 3 | 3 |
| Quaternary ammonium | H₃C\⁺\H₃C—N—CH₂COOCH₂CHC₁₀H₂₁ /H₃C  C₈H₁₇  Cl⁻ | H₃C\⁺\H₃C—N—(CH₂)₃COOCH₂CHC₁₈H₃₇ /H₃C  C₁₆H₃₃  Cl⁻ | H₃C\⁺\H₃C—N—(CH₂)₅COOCH₂CHC₁₈H₃₇ /H₃C  C₁₆H₃₃  Cl⁻ |
| Softness | 2 | 3 | 3 |
| Smell | ○ | ○ | ○ |

We claim:

1. A quaternary ammonium salt represented by the formula (7-I-2):

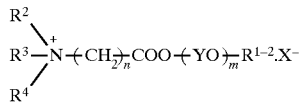

wherein $R^{1-2}$: linear or branched $C_{36}-C_{44}$ alkyl or alkenyl group;

$R^2$, $R^3$, $R^4$: $C_1-C_5$ alkyl or hydroxyalkyl group, wherein $R^2$, $R^3$ and $R^4$ may be the same or different from each other;

Y: linear or branched $C_2-C_4$ alkylene group;

m: an average number of 0 to 20 moles of alkylene oxide;

n: an integer of 1 to 6; and $X^-$: an anion group.

2. A quaternary ammonium salt as set forth in claim 1, which is represented by the formula (1-I-2):

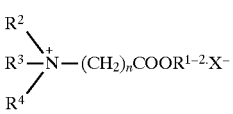

wherein $R^{1-2}$: linear or branched $C_{36}-C_{44}$ alkyl; and $R^2$, $R^3$, $R^4$, n, $X^-$: each as defined above.

4. A quaternary ammonium salt as set forth in claim 1, which is represented by the general formula (1-I-1):

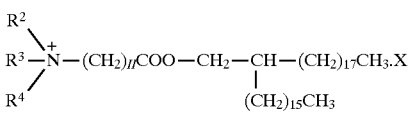

wherein $R^2$, $R^3$, $R^4$, n, $X^-$: each as defined above.

5. A quaternary ammonium salt as set forth in claim 1, wherein m is an average number of 1 to 20.

6. A quaternary ammonium salt as set forth in claim 1, which is represented by the general formula (2-I-1) wherein m is a number of 1 to 20 corresponding to the average number of alkylene oxide molecules added:

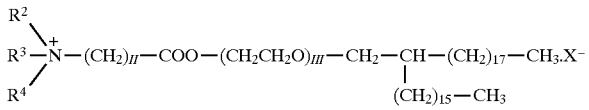

wherein $R^2$, $R^3$, $R^4$, n, m, $X^-$: each as defined above.

7. A liquid softener composition comprising the following component (7-A) and water, wherein component (7-A) is present in the composition in an amount of 3 to 40% by weight:
component (7-A): a quaternary ammonium salt represented by the formula (7-I):

(7-I)

wherein
$R^1$ : branched $C_{20}$–$C_{44}$ alkyl or alkenyl group;
$R_2$, $R_3$, $R_4$: $C_1$–$C_5$ alkyl or hydroxyalkyl group, wherein $R_2$, $R_3$ and $R_4$ may be the same or different from each other;
Y: linear or branched $C_2$–$C_4$ alkylene group;
m: an average number of 0 to 20 moles of alkylene oxide;
n: an integer of 1 to 6; and
$X^-$: an anion group.

8. A composition as set forth in claim 7, wherein m is 0.
9. A composition as set forth in claim 8, wherein $R^1$ is a branched $C_{28}$–$C_{44}$ alkyl group.
10. A composition as set forth in claim 8, wherein the quaternary ammonium salt is represented by the general formula (1-I-1):

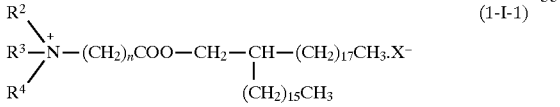

(1-I-1)

wherein $R^2$, $R^3$, $R^4$, n, $X^-$: each as defined above.

11. A composition as set forth in claim 8, which further contains a linear or branched, saturated or unsaturated $C_8$–$C_{44}$ alcohol in an amount of at most 110% by weight based on the weight of the quaternary ammonium salt.

12. A composition as set forth in claim 7, wherein m is an average number of 1 to 20.

13. A composition as set forth in claim 12, wherein $R^1$ group is a group represented by the formula:

wherein p is a number of 9 to 21L and Y is ethylene group.

14. A composition as set forth in claim 12, wherein the quaternary ammonium salt is represented by the general formula (2-1-1):

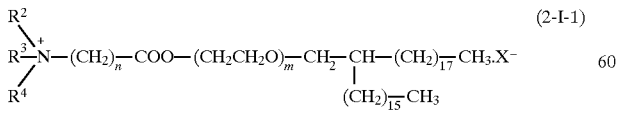

(2-I-1)

wherein $R^2$, $R^3$, $R^4$, n, m, $X^-$: each as defined above.

15. A composition as set forth in claim 12, which further contains a linear or branched, saturated or unsaturated $C_8$–$C_{44}$ alcohol in an amount of at most 110% by weight based on the weight of the quaternary ammonium salt.

16. A liquid softener composition comprising:
(a) a mixture comprising a compound represented by the following formula (3-I);

(3-I)

wherein
$A^1$, $A^2$, $A^3$: RCO group or H atom, wherein R represents linear or branched $C_7$–$C_{23}$ alkyl or alkenyl group, with the proviso that one of $A^1$, $A^2$ and $A^3$ is RCO group and the others thereof are H atom,
Q: $C_2$–$C_3$ alkylene group or a mixture of $C_2$ alkylene group with $C_3$ alkylene group, and
a, b, c: a number of 0 or above, with the proviso that the sum of a, b and c is 1 to 50 on an average,
a compound represented by the following formula (3-II);

(3-II)

wherein
$B^1$, $B^2$, $B^3$: RCO group or H atom, wherein R is as defined above, with the proviso that two of $B^1$, $B^2$ and $B^3$ are RCO group and the other thereof is H atom, and
Q, a, b, c: each as defined above,
a compound represented by the following formula (3-III)

(3-III)

wherein
$D^1$, $D^2$, $D^3$: RCO group wherein R is as defined above, and
Q, a, b, c: each as defined above, and
a compound represented by the following formula (3-IV)

(3-IV)

wherein
Q, a, b, c; are each as defined above, with the provisos that a mixing ratio by weight of the compounds (3-I), (3-II), (3-III) and (3-IV) satisfy the following relationships:
compound (3-I)/the total weight of compounds (3-I), (3-II), (3-III) and (3-IV)=0.040 to 0.527,
compound (3-II)/the total weight of compounds (3-I), (3-II), (3-III) and (3-IV)=0.133 to 0.469,
compound (3-III)/the total weight of compounds (3-I), (3-II), (3-III) and (3-IV)=0.013 to 0.661, and
compound (3-IV)/the total weight of compounds (3-I), (3-II), (3-III) and (3-IV)=0.001 to 0.417; and also with the proviso that the mixture comprising compounds (3-I), (3-II), (3-III) and (3-IV) has a Griffin's HLB value of 5 to 15; and (b) a quaternary ammonium salt represented by the following formula (3-V):

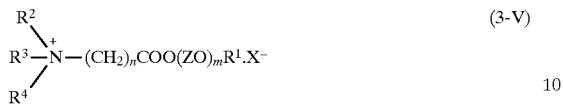

wherein

R$^1$ is a linear or branched C$_{20}$–C$_{44}$ alkyl or alkenyl group;

R$^2$, R$^3$, R$^4$ are each a C$_1$–C$_5$ alkyl or hydroxylalkyl group, wherein R$^2$, R$^3$ and R$^4$ may be the same or different from each other;

Z is a C$_2$–C$_3$ alkylene group or a mixture of a C$_2$ alkylene group with C$_3$ alkylene group;

m is a number of 0 to 20;

n is a number of 1 to 6; and

X$^-$ is an anion group; and in a weight ratio of component (a) to component (b) is 2/1 to 1/9.

17. A composition as set forth in claim 16, wherein R in formulae (3-I) to (3-III) is at least one member selected from the group consisting of an alkyl group resulting from coconut oil fatty acid, an alkyl group resulting from palm kernel oil fatty acid, an alkyl group resulting from palm oil fatty acid, an alkyl group resulting from palm stearic acid, an alkyl group resulting from tallow fatty acid, and an alkyl group resulting from hardened tallow fatty acid.

18. A composition as set forth in claim 16, wherein R in formulae (3-I) to (3-III) is at least one member selected from the group consisting of an alkyl group resulting from tallow fatty acid, an alkyl group resulting from hardened tallow fatty acid, an alkyl group resulting from palm stearic acid, and an alkyl group resulting from hardened palm stearic acid.

19. A composition as set forth in claim 16, wherein the quaternary ammonium salt is represented by the general formula (3-V-1):

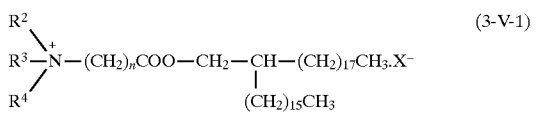

wherein R$^2$, R$^3$, R$^4$, n, X$^-$: each as defined above.

20. A composition as set forth in claim 16, wherein the total amount of the mixture of 3-I, 3-II, 3-III, 3-IV and 3-V is 3 to 40% by weight based on the composition.

21. A composition as set forth in claim 16, which further contains a linear or branched, saturated or unsaturated C$_8$–C$_{44}$ alcohol in an amount of at most 110% by weight based on the quaternary ammonium salt.

22. A liquid softener composition comprising the following components (4-A) and (4-B) at a weight ratio of the component (4-A) to the component (4-B) of 2/1 to 1/9:

component (4-A)

a compound represented by the following general formula (4-I):

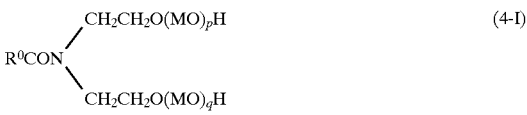

wherein

R$^0$: linear or branched C$_7$–C$_{23}$ alkyl or alkenyl group;

M: C$_2$–C$_3$ alkylene group or a mixture of C$_2$ alkylene group with C$_3$ alkylene group; and p, q: a number of 0 or above, with the proviso that the sum of p and q is 0 to 4 on an average and component (4-B)

a quaternary ammonium salt represented by the following general formula (4-II):

wherein

R$^1$: linear or branched C$_{20}$–C$_{44}$ alkyl or alkenyl group;

R$^2$, R$^3$, R$^4$: C$_1$–C$_5$ alkyl or hydroxyalkyl group, wherein R$^2$, R$^3$ and R$^4$ may be the same or different from each other;

Z: C$_2$–C$_3$ alkylene group or a mixture of C$_2$ alkylene group with C$_3$ alkylene group;

m: a number of 0 to 20;

n: a number of 1 to 6; and

X$^-$: an anion group.

23. A composition as set forth in claim 22, wherein p and q are 0 in the general formula (4-I).

24. A composition as set forth in claim 22, wherein R$^0$ in formulae (4-I) is at least one member selected from the group consisting of an alkyl group resulting from coconut oil fatty acid, an alkyl group resulting from palm kernel oil fatty acid, an alkyl group resulting from palm oil fatty acid, an alkyl group resulting from palm stearic fatty acid, an alkyl group resulting from hardened palm stearic fatty acid, an alkyl group resulting from tallow fatty acid, and an alkyl group resulting from hardened tallow fatty acid.

25. A composition as set forth in claim 22, wherein the component (4-B) is a quaternary ammonium salt represented by the general formula (4-II-1):

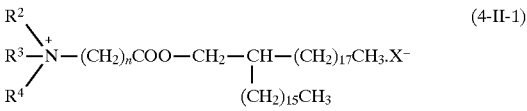

wherein R$^2$, R$^3$, R$^4$, n, X$^-$: each as defined above.

26. A composition as set forth in claim 22, wherein the total amount of the components (4-A) and (4-B) is 3 to 40% by weight based on the composition.

27. A composition as set forth in claim 22, which further comprises a linear or branched, saturated or unsaturated C$_8$–C$_{44}$ alcohol as component (4-C) in an amount of at most 110% by weight based on the component (4-B).

28. A process of preparing a quaternary ammonium salt represented by the general formula (5-I):

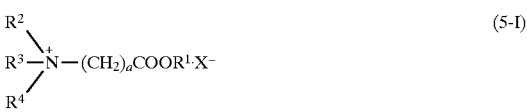

wherein

R$^1$ represents a linear or branched C$_{20}$–C$_{44}$ alkyl or alkenyl group; R$^2$, R$^3$ and R$^4$ are the same or different from each other and represent a $C_1$–$C_5$ alkyl or hydroxyalkyl group;

a is a number of 1 to 6; and $X^-$ represents an anion, which comprises reacting a tertiary amine of the formula $NR^2R^3R^4$ where $R^2$, $R^3$ and $R^4$ are defined above, with a quaternizing agent, in the presence of a polyhydric alcohol ester represented by the general formula (5-II):

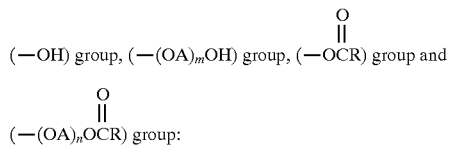  (5-II)

wherein

G: is a residue of a polyhydric alcohol free from alcoholic hydroxyl groups;

(—OH) group, (—(OA)$_m$OH) group, (—OCR) group and (—(OA)$_n$OCR) group:

each bonded to G at a carbon atom to which an alcoholic hydroxy group used to be bonded, wherein A group represents $C_2$–$C_4$ alkylene group, R group represents linear or branched $C_7$–$C_{23}$ alkyl or alkenyl group, and m and n are each an average number of 0 to 100 moles of alkylene oxide, m and n being the same or different from each other;

p, q, r and s: each a number of 0 or above, with the provisos that neither the sum of p and q nor that of r and s is 0.

29. A process as set forth in claim 28, wherein the polyhydric alcohol ester represented by the general formula (5-II) is at least one member selected from the group consisting of the following compounds (a), (b) and (c):

(a) fatty acid esters of pentaerythritol (having at least one hydroxyl group) and adducts thereof with alkylene oxide (wherein the alkylene oxide group has 2 or 3 carbon atoms)

(b) fatty acid esters of glycerol having at least one hydroxyl group, and adducts thereof with an alkylene oxide wherein the alkylene oxide has 2 or 3 carbon atoms, and (c) fatty acid esters of sorbitan having at least one hydroxyl group, and adducts thereof with an alkylene oxide wherein the alkylene oxide has 2 or 3 carbon atoms.

30. A process as set forth in claim 28, wherein the polyhydric alcohol ester represented by the general formula (5-II) is a fatty acid ester of glycerol having at least one hydroxyl group and an adduct thereof with an alkylene oxide wherein the alkylene oxide has 2 or 3 carbon atoms.

31. A process as set forth in claim 28, wherein the polyhydric alcohol ester represented by the general formula (5-II) is a product obtained by reacting a natural fat or oil with glycerol and an alkylene oxide at a molar ratio of the fat or oil to glycerol to the alkylene oxide of 1: (0.1 to 5): (2 to 100).

32. A process as set forth in claim 28, wherein the polyhydric alcohol ester represented by the general formula (5-II) is present in an amount of 1 to 50% by weight based on the total weight of reactants.

33. A process of preparing a quaternary ammonium salt represented by the general formula (6-I):

  (6-I)

wherein $R^1$ represents linear or branched $C_{20}$–$C_{44}$ alkyl or alkenyl group;

$R^2$, $R^3$ and $R^4$ are the same or different from each other and represent a $C_1$–$C_5$ alkyl or hydroxyalkyl group;

a is a number of 1 to 6; and tertiary amine of the formula $NR^2R^3R^4$ where $R^2$, $R^3$ and $R^4$ are defined above, compound represented by the general formula (6-II):

  (6-II)

wherein $R^5$ represents linear or branched $C_7$–$C_{35}$ alkyl or alkenyl group;

$A^1$ and $A^2$ are the same or different from each other and represent a $C_2$–$C_4$ alkylene group; and n and m may be the same or different from each other and represent an average number of alkylene oxide molecules, with the sum of n and m being 0 to 4.

34. A process as set forth in claim 33, wherein $R^5CO$— is a fatty acid residue resulting from a natural fat or oil and n and m are 0.

35. A process as set forth in claim 33, wherein the compound represented by the general formula (6-II) is present in an amount of 1 to 50% by weight based on the total weight of reactants.

* * * * *